(12) United States Patent
Jitsuoka et al.

(10) Patent No.: US 8,420,823 B2
(45) Date of Patent: Apr. 16, 2013

(54) LONG-CHAIN FATTY ACYL ELONGASE INHIBITOR COMPRISING ARYLSULFONYL DERIVATIVE AS ACTIVE INGREDIENT

(75) Inventors: Makoto Jitsuoka, Moriya (JP);
Tsuyoshi Nagase, Tokusima (JP);
Nagaaki Sato, Saitama (JP); Daisuke Tsukahara, Toride (JP)

(73) Assignee: MSD K.K., Tokyo (JP)

( * ) Notice: Subject to any disclaimer, the term of this patent is extended or adjusted under 35 U.S.C. 154(b) by 271 days.

(21) Appl. No.: 12/933,444

(22) PCT Filed: Apr. 17, 2009

(86) PCT No.: PCT/JP2009/057725
§ 371 (c)(1),
(2), (4) Date: Sep. 20, 2010

(87) PCT Pub. No.: WO2009/131065
PCT Pub. Date: Oct. 29, 2009

(65) Prior Publication Data
US 2011/0009622 A1   Jan. 13, 2011

(30) Foreign Application Priority Data
Apr. 24, 2008  (JP) .................................. 2008-113340

(51) Int. Cl.
*A61K 31/4439* (2006.01)
*A61K 31/454* (2006.01)
*A61K 31/4453* (2006.01)
*C07D 401/10* (2006.01)

(52) U.S. Cl.
USPC ........ 546/275.4; 546/112; 546/211; 546/234; 546/278.4; 544/316; 564/162; 514/274; 514/299; 514/326; 514/327; 514/343; 514/618; 514/341

(58) Field of Classification Search ................... 514/274, 514/299, 326, 341, 343, 327, 618; 546/112, 546/211, 234, 278.5, 275.4; 544/316; 564/162
See application file for complete search history.

(56) References Cited

U.S. PATENT DOCUMENTS

| | | | |
|---|---|---|---|
| 5,849,780 A | 12/1998 | Di Malta et al. | |
| 6,815,440 B2 | 11/2004 | Thorwart et al. | |
| 7,417,058 B2 | 8/2008 | Halazy et al. | |
| 2006/0014811 A1 | 1/2006 | Muto et al. | |
| 2009/0036420 A1* | 2/2009 | Galley et al. | ............... 514/210.2 |

FOREIGN PATENT DOCUMENTS

| | | |
|---|---|---|
| CA | 2 129 215 A1 | 1/1995 |
| JP | 07-247269 A | 9/1995 |
| JP | 2000-500145 A | 1/2000 |
| JP | 200500145 | 1/2000 |
| JP | 2002201172 | 7/2002 |
| JP | 2004-523475 A | 8/2004 |
| WO | 03/103655 A1 | 12/2003 |
| WO | 2004/018414 A2 | 3/2004 |
| WO | 2004/018414 A3 | 3/2004 |
| WO | 2007/041366 A1 | 4/2007 |
| WO | 2007/067836 A2 | 6/2007 |
| WO | 2007/067836 A3 | 6/2007 |
| WO | WO 2008011476 A2 * | 1/2008 |
| WO | 2008/022171 A1 | 2/2008 |
| WO | 2009/047798 A2 | 4/2009 |
| WO | 2009/047798 A3 | 4/2009 |
| WO | 2010/083264 A1 | 7/2010 |

OTHER PUBLICATIONS

Lambeng, N "Arylsulfonamides as a new class of cannabinoid CB1 receptor ligands: Identification of a lead and initial SAR studies." Bioorganic & Medicinal Chemistry Letters, 2007, 17(1), 272-277.*
STN-Chemical database RN 420831-45-4 entry Benzamide, N-(2-methoxyphenyl)-3-(1-pyrrolidinylsulfony1)—entered on May 23, 2002.*
"http://web.archive.org/web/20070630171813/http://www.enamine.net/index.php?option=com_content&task=view&id=22 &menuid=51 &PHPSESSID=64a4f248f69d671a413f487bb62c4d90" dated Jun. 30, 2007, accessed Nov. 9, 2011.*
Lee, S.H. et al., "Fatty Acid Synthesis by Elongases in Trypanosomes", Cell, 2006, pp. 691-699, vol. 126.
Matsuzaka, T. et al., "Cloning and characterization of a mammalian fatty acyl-CoA elongase as a lipogenic enzyme regulated by SREBPs", Journal of Lipid Research, 2002, pp. 911-920, vol. 43.
ACS on STN, RN-941047-95-6, Jul. 4, 2007.
ACS on STN, RN 941095-05-2, Jul. 4, 2007.
ACS on STN, RN 328549-28-6, Mar. 25, 2001.

\* cited by examiner

*Primary Examiner* — David K O Dell
(74) *Attorney, Agent, or Firm* — Janet E. Fair; John C. Todaro

(57) ABSTRACT

[Problem] To provide compounds useful as preventives or remedies for circular system disorders, nervous system disorders, metabolic disorders, reproduction system disorders, digestive system disorders, neoplasm, infectious diseases, etc., or as herbicides.
[Means for Solution] A long-chain fatty acyl elongase inhibitor comprising, as the active ingredient thereof, a compound or a pharmaceutically-active salt thereof of a formula (I):

[Chemical Formula 1]

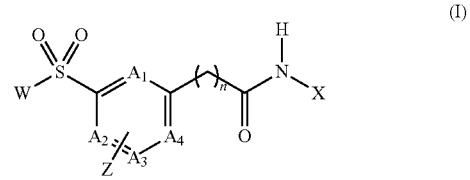

[wherein W represents a hydrogen atom, a $C_{1-6}$ alkyl, etc.; X represents an aryl, a heteroaryl, etc.; n indicates 0 or 1; Z represents a hydrogen atom, a $C_{1-6}$ alkyl, etc.; $A_1$, $A_2$, $A_3$ and $A_4$ each independently represent CH or N].

1 Claim, No Drawings

LONG-CHAIN FATTY ACYL ELONGASE INHIBITOR COMPRISING ARYLSULFONYL DERIVATIVE AS ACTIVE INGREDIENT

CROSS-REFERENCE TO RELATED APPLICATIONS

This application is a U.S. National Phase application under 35 U.S.C. §371 of PCT Application No. PCT/JP2009/057725, filed Apr. 17, 2009, which published as WO 2009/131065 A1 on Oct. 29, 2009, and claims priority under 35 U.S.C. §365(b) from Japanese patent application No. JP2008-113340, filed Apr. 24, 2008.

TECHNICAL FIELD

The present invention is useful in the field of medicine. More precisely, the arylsulfonyl derivative of the invention acts as a long-chain fatty acyl elongase (hereinafter this may be abbreviated as LCE) inhibitor and is useful for preventives or remedies for various circulation system disorders, nervous system disorders, metabolic disorders, reproduction system disorders, digestive system disorders, neoplasm, infectious diseases, etc., or for herbicides.

BACKGROUND ART

Obesity is a condition of having a significantly greater body weight than an average body weight as a result of accumulation of neutral fat in fat cells due to continuous excess energy intake compared with energy consumption (Eiji Itagaki, "STEP series, Metabolism, Endocrinology", Kaiba Shobo, 1st Ed., 1998, p. 105). It is known that the excessively-accumulated fat causes, for example, insulin resistance, diabetes, hypertension, hyperlipidemia, etc., and that a plurality of those factors as combined much increase a risk of onset of atherosclerosis; and the condition is referred to as a metabolic syndrome. Further, it is known that hypertriglyceridemia or obesity increases a risk of, for example, pancreatitis, hepatic dysfunction, cancer such as breast cancer, uterine cancer, ovarian cancer, colon cancer, prostate cancer, etc., menstrual abnormality, arthritis, cholecystitis, gastroesophageal reflux, obesity hypoventilation syndrome (Pickwickian syndrome), sleep apnea syndrome, etc. It is widely known that diabetes often leads to, onset of, for example, angina pectoris, heart failure, stroke, claudication, retinopathy, reduced vision, renal failure, neuropathy, skin ulcer, infection, etc. [The Merck Manual of Medical Information, Domestic 2nd Ed., Merck & Co., 2003].

LCE is an enzyme existing in the endoplasmic reticula of cells, and is a type of an enzyme group that catalyzes the carbon chain elongation reaction of a fatty acid having at least 12 carbon atoms, specifically catalyzing the rate-determining condensation step of the reaction. In mammals, many fatty acids newly synthesized in the living bodies have a chain length of from 16 to 18 carbon atoms. These long-chain fatty acids constitute more than 90% of all the fatty acids existing in cells. These are important components of membranes, and are the essential ingredients of the fatty tissue that is the largest energy storage organ in animals. New fatty acid synthesis occurs most frequently in liver, and through the synthesis, the excessive glucose in a living body is converted into a fatty acid. Glucose is converted into a pyruvic acid salt through glycolysis, and the pyruvic acid salt is converted into a citric acid salt by mitochondria and then transferred to a cytosol. ATP citrate lyase in the cytosol produces an acetyl CoA that is a precursor of fatty acid and cholesterol. The acetyl CoA is carboxylated by an acetyl CoA carboxylate (ACC) to form a malonyl CoA. A multifunctional enzyme, fatty acid synthase (FAS) elongates a fatty acid by two carbons, using malonyl CoA, acetyl CoA and NADPH. In rodents, the main final product of FAS is palmitoyl CoA having 16 carbon atoms, and the carbon chain of the palmitoyl CoA is elongated by 2 carbons by LCE [Journal of Biological Chemistry, 276 (48), 45358-45366, (2001)]. It is known that excessive fatty acid synthesis promotion in living bodies increases neutral fat, etc., and finally causes fat accumulation. For example, WO2005/005665 (Patent Reference 1) shows a direct relationship between LCE and obesity. In addition, there is a report indicating the change in the expression level of mouse FACE (LCE) by eating (Matsuzaka T., et al., J. Lipid Res., 43(6): 911-920 (2002); Non-Patent Reference 1).

It is known that LCE exists also in protozoans and nematodes and participates in cell growth. For example, it is said that, in Trypanosoma protozoans that cause African trypanosomiasis (African sleeping sickness), a long-chain fatty acid is produced in a fatty acid elongation route including LCE, and the intercellular fatty acyl elongation reaction inhibition may have some influence on the proliferation of Trypanosoma protozoans (Lee S. H., et al., Cell, 126: 691-699 (2006); Non-Patent Reference 2).

Any arylsulfonyl derivative having an LCE inhibitory effect is heretofore not known at all. A part of the compounds of the invention, arylsulfonyl derivatives are novel compounds heretofore unknown in the art.

Non-Patent Reference 1: J. Lipid Res., 43(6): 911-920 (2002)
Non-Patent Reference 2: J. Cell, 126: 691-699 (2006)

DISCLOSURE OF THE INVENTION

Problems that the Invention is to Solve

An object of the invention is to provide a compound having an LCE inhibitory effect.

Means for Solving the Problems

The present inventors have assiduously studied and, as a result, have found that a compound having a sulfonyl-substituted 6-membered ring with an aryl, a heteroaryl or the like bonding to the 3-position of the ring via an amide or an urea (hereinafter referred to as "compound of the invention") has an excellent LCE inhibitory effect, and have completed the present invention.

Specifically, the invention provides the following:
(1) A long-chain fatty acyl elongase (LCE) inhibitor comprising, as the active ingredient thereof, a compound of a formula (I) or a pharmaceutically-acceptable salt thereof:

[Chemical Formula 1]

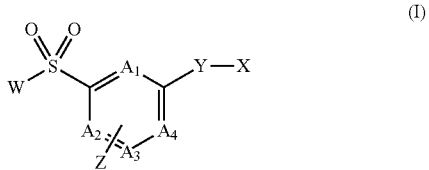

[wherein,
W represents a $C_{1-6}$ alkyl, a $C_{3-8}$ cycloalkyl, an aryl, a heteroaryl, an aralkyl, a heteroaralkyl or —N($R^1$)($R^2$);

$R^1$ and $R^2$ each independently represent a hydrogen atom, a $C_{1-6}$ alkyl, a $C_{3-8}$ cycloalkyl, an aryl, a heteroaryl, an aralkyl or a heteroaralkyl, or $R^1$ and $R^2$, taken together with the nitrogen atom to which they bond, form a nitrogen-containing hetero ring;

the alkyl, the cycloalkyl, the aryl, the heteroaryl, the aralkyl, the heteroaralkyl or the nitrogen-containing hetero ring may be substituted with a substituent selected from a group consisting of a hydroxy, a cyano, a carboxyl, a sulfo, a halogen, a $C_{1-6}$ alkyl, a halo-$C_{1-6}$ alkyl, a $C_{3-8}$ cycloalkyl, a $C_{1-6}$ alkoxy, a halo-$C_{1-6}$ alkoxy, a hydroxy-$C_{1-6}$ alkyl, an amino-$C_{1-6}$ alkyl, a $C_{1-6}$ alkoxy-$C_{1-6}$ alkyl, an amino (the amino may be mono- or di-substituted with a $C_{1-6}$ alkyl, an aryl or a heteroaryl), a carbamoyl (the carbamoyl may be mono- or di-substituted with a $C_{1-6}$ alkyl, an aryl or a heteroaryl), a sulfanyl (the sulfanyl may be mono-substituted with a $C_{1-6}$ alkyl, an aryl or a heteroaryl), a $C_{1-6}$ alkylsulfinyl, an arylsulfinyl, a heteroarylsulfinyl, a $C_{1-6}$ alkylsulfonyl, an arylsulfonyl, a heteroarylsulfonyl, a sulfamoyl (the sulfamoyl may be mono- or di-substituted with a $C_{1-6}$ alkyl, an aryl or a heteroaryl), a $C_{1-6}$ alkylsulfonylamino, an arylsulfonylamino, a heteroarylsulfonylamino, a $C_{1-6}$ alkylcarbonyl, an arylcarbonyl, a heteroarylcarbonyl, a $C_{1-6}$ alkoxycarbonyl, an aryloxycarbonyl, a heteroaryloxycarbonyl, a carbamoylamino (the carbamoylamino may be mono- or di-substituted with a $C_{1-6}$ alkyl, an aryl or a heteroaryl), a $C_{1-6}$ alkoxycarbonylamino, an aryloxycarbonylamino, a heteroaryloxycarbonylamino, a $C_{1-6}$ alkylcarbonylamino, an arylcarbonylamino, a heteroarylcarbonylamino, an aryl, a heteroaryl, an aralkyl, a heteroaralkyl, an aralkyloxy and a heteroaralkyloxy;

X represents an aryl, a heteroaryl, an aralkyl or a heteroaralkyl, and the group may be substituted with a substituent selected from a group consisting of a hydroxy, a cyano, a carboxyl, a sulfo, a halogen, a $C_{1-6}$ alkyl, a halo-$C_{1-6}$ alkyl, a $C_{3-8}$ cycloalkyl, a $C_{1-6}$ alkoxy, a halo-$C_{1-6}$ alkoxy, a hydroxy-$C_{1-6}$ alkyl, an amino-$C_{1-6}$ alkyl, a $C_{1-6}$ alkoxy-$C_{1-6}$ alkyl, an amino (the amino may be mono- or di-substituted with a $C_{1-6}$ alkyl, an aryl or a heteroaryl), a carbamoyl (the carbamoyl may be mono- or di-substituted with a $C_{1-6}$ alkyl, an aryl or a heteroaryl), a sulfanyl (the sulfanyl may be mono-substituted with a $C_{1-6}$ alkyl, an aryl or a heteroaryl), a $C_{1-6}$ alkylsulfinyl, an arylsulfinyl, a heteroarylsulfinyl, a $C_{1-6}$ alkylsulfonyl, an arylsulfonyl, a heteroarylsulfonyl, a sulfamoyl (the sulfamoyl may be mono- or di-substituted with a $C_{1-6}$ alkyl, an aryl or a heteroaryl), a $C_{1-6}$ alkylsulfonylamino, an arylsulfonylamino, a heteroarylsulfonylamino, a $C_{1-6}$ alkylcarbonyl, an arylcarbonyl, a heteroarylcarbonyl, a $C_{1-6}$ alkoxycarbonyl, an aryloxycarbonyl, a heteroaryloxycarbonyl, a carbamoylamino (the carbamoylamino may be mono- or di-substituted with a $C_{1-6}$ alkyl, an aryl or a heteroaryl), a $C_{1-6}$ alkoxycarbonylamino, an aryloxycarbonylamino, a heteroaryloxycarbonylamino, a $C_{1-6}$ alkylcarbonylamino, an arylcarbonylamino, a heteroarylcarbonylamino, an aryl, a heteroaryl, an aralkyl, a heteroaralkyl, an aralkyloxy and a heteroaralkyloxy;

Y represents a formula (II-1), a formula (II-2), a formula (II-3) or a formula (II-4):

[Chemical Formula 2]

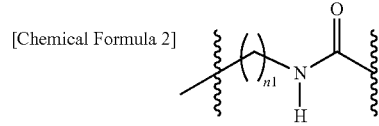
(II-1)

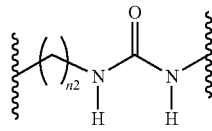
(II-2)

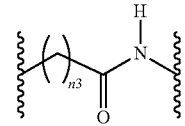
(II-3)

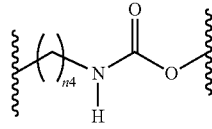
(II-4)

(wherein n1, n2, n3 and n4 each indicate 0 or 1),
wherein the hydrogen atom in formula (II-1) to formula (II-4) may be substituted with a $C_{1-6}$ alkyl, a halo-$C_{1-6}$ alkyl or a $C_{3-8}$ cycloalkyl;

Z represents a hydrogen atom, a hydroxy, a cyano, a carboxyl, a sulfo, a halogen, a $C_{1-6}$ alkyl, a halo-$C_{1-6}$ alkyl, a $C_{3-8}$ cycloalkyl, a $C_{1-6}$ alkoxy, a halo-$C_{1-6}$ alkoxy, a hydroxy-$C_{1-6}$ alkyl, an amino-$C_{1-6}$ alkyl, a $C_{1-6}$ alkoxy-$C_{1-6}$ alkyl, an amino (the amino may be mono- or di-substituted with a $C_{1-6}$ alkyl, an aryl or a heteroaryl), a carbamoyl (the carbamoyl may be mono- or di-substituted with a $C_{1-6}$ alkyl, an aryl or a heteroaryl), a sulfanyl (the sulfanyl may be mono-substituted with a $C_{1-6}$ alkyl, an aryl or a heteroaryl), a $C_{1-6}$ alkylsulfinyl, an arylsulfinyl, a heteroarylsulfinyl, a $C_{1-6}$ alkylsulfonyl, an arylsulfonyl, a heteroarylsulfonyl, a sulfamoyl (the sulfamoyl may be mono- or di-substituted with a $C_{1-6}$ alkyl, an aryl or a heteroaryl), a $C_{1-6}$ alkylsulfonylamino, an arylsulfonylamino, a heteroarylsulfonylamino, a $C_{1-6}$ alkylcarbonyl, an arylcarbonyl, a heteroarylcarbonyl, a $C_{1-6}$ alkoxycarbonyl, an aryloxycarbonyl, a heteroaryloxycarbonyl, a carbamoylamino (the carbamoylamino may be mono- or di-substituted with a $C_{1-6}$ alkyl, an aryl or a heteroaryl), a $C_{1-6}$ alkoxycarbonylamino, an aryloxycarbonylamino, a heteroaryloxycarbonylamino, a $C_{1-6}$ alkylcarbonylamino, an arylcarbonylamino, a heteroarylcarbonylamino, an aryl, a heteroaryl, an aralkyl, a heteroaralkyl, an aralkyloxy or a heteroaralkyloxy; and $A_1$, $A_2$, $A_3$ and $A_4$ each independently represent CH or N, provided that at least three of $A_1$, $A_2$, $A_3$ and $A_4$ are CH].

The invention also provides the following:
(2) A pharmaceutical composition containing the inhibitor of formula (I),
(3) A preventive or a remedy for diabetes, obesity or non-alcoholic fatty liver, comprising, as the active ingredient thereof, the inhibitor of formula (I),
(4) The inhibitor of (1), which is used as a remedial active substance for treatment of long-chain fatty acyl elongase-related disorders,
(5) A compound of a formula (I-1) mentioned below.

In particular, the compound of the invention has an LCE inhibitor effect, and is therefore useful as a preventive and a remedy for LCE-related various disorders, for example, circular system disorders such as hypertension, angina pectoris, heart failure, myocardial infarction, stroke, claudication, diabetic nephropathy, diabetic retinopathy, reduced vision, electrolytic abnormality, atherosclerosis, etc.; central nervous system disorders such as bulimia, diabetic neuropathy, etc.;

metabolic disorders such as metabolic syndrome, obesity, diabetes, insulin resistance, hyperlipidemia, hypercholesterolemia, hypertriglyceridemia, dyslipidemia, non-alcoholic fatty liver, hormone secretion abnormality, gout, fatty liver, etc.; reproduction system disorders such as menstrual abnormality, sexual dysfunction, etc.; digestive system disorders such as hepatic dysfunction, pancreatitis, cholecystitis, gastroesophageal reflux, etc.; respiratory system disorders such as obesity hypoventilation syndrome (Pickwickian syndrome), sleep apnea syndrome, etc.; infectious disorders caused by bacteria, fungi, parasites; malignant neoplasm; inflammatory disorders such as arthritis, skin ulcer, etc., and also as a herbicide.

The meanings of the terms used in this description are described below, and the invention is described in more detail.

"Halogen" means a fluorine atom, a chlorine atom, a bromine atom, an iodine atom.

"$C_{1-6}$ alkyl" means a linear or branched alkyl having from 1 to 6 carbon atoms, including, for example, methyl, ethyl, propyl, isopropyl, butyl, isobutyl, sec-butyl, tert-butyl, pentyl, isopentyl, hexyl, isohexyl, etc.

"Halo-$C_{1-6}$ alkyl" means the above-mentioned $C_{1-6}$ alkyl substituted with one or more, preferably from 1 to 3, the same or different, above-mentioned halogen atoms at the substitutable position thereof, and includes, for example, fluoromethyl, difluoromethyl, trifluoromethyl, 2-fluoroethyl, 1,2-difluoroethyl, chloromethyl, 2-chloroethyl, 1,2-dichloroethyl, bromomethyl, iodomethyl, etc.

"$C_{3-8}$ cycloalkyl" means a cycloalkyl having from 3 to 8 carbon atoms, including, for example, cyclopropyl, cyclobutyl, cyclopentyl, cyclohexyl, etc.

The above-mentioned "alkyl", "haloalkyl" or "cycloalkyl" may be optionally substituted with a substituent selected from a group consisting of a halogen, a cyano, a nitro, an oxo, —$OR^{51}$, —$R^{51}$, —$COR^{51}$, —$CO_2R^{51}$, —$NR^{61}R^{71}$, —$SR^{51}$, —$SOR^{51}$, —$SO_2R^{51}$, —$CONR^{61}R^{71}$, —$NR^{51}COR^{61}$, —$NR^{51}CO_2R^{61}$, —$OCONR^{61}R^{71}$, —$NR^{51}SO_2R^{61}$, —$SO_2NR^{61}R^{71}$ and —$NR^{51}CONR^{61}R^{71}$; and $R^{51}$, $R^{61}$ and $R^{71}$ are the same or different, each representing a hydrogen, a $C_{1-6}$ alkyl, a $C_{3-8}$ cycloalkyl, an aryl, a heterocyclyl or a heteroaryl; or $R^{61}$ and $R^{71}$, taken together with the nitrogen atom to which they bond, may form a heterocyclyl.

"$C_{1-6}$ alkoxy" means a linear or branched alkoxy having from 1 to 6 carbon atoms, including, for example, methoxy, ethoxy, propoxy, isopropoxy, butoxy, sec-butoxy, isobutoxy, tert-butoxy, pentyloxy, isopentyloxy, hexyloxy, isohexyloxy, etc.

"Halo-$C_{1-6}$ alkoxy" means the above-mentioned $C_{1-6}$ alkoxy substituted with one or more, preferably from 1 to 3, the same or different, above-mentioned halogen atoms at the substitutable position thereof, and includes, for example, fluoromethoxy, difluoromethoxy, trifluoromethoxy, 2-fluoroethoxy, 1,2-difluoroethoxy, chloromethoxy, 2-chloroethoxy, 1,2-dichloroethoxy, bromoethoxy, iodomethoxy, etc.

"$C_{1-6}$ alkoxycarbonyl" means a carbonyl with the above-mentioned $C_{1-6}$ alkoxy bonding thereto, and includes, for example, methoxycarbonyl, ethoxycarbonyl, n-propyloxycarbonyl, etc.

"$C_{1-6}$ alkoxycarbonylamino" means an amino group (—$NH_2$) in which one hydrogen atom is substituted with the above-mentioned $C_{1-6}$ alkoxycarbonyl, and includes, for example, methoxycarbonylamino, ethoxycarbonylamino, n-propyloxycarbonylamino, etc.

"$C_{1-6}$ alkylcarbonyl" means a carbonyl with the above-mentioned $C_{1-6}$ alkyl bonding thereto, and includes, for example, acetyl, propionyl, isobutyryl, valeryl, isovaleryl, pivaloyl, etc.

"$C_{1-6}$ alkylcarbonylamino" means an amino group in which one hydrogen atom is substituted with the above-mentioned $C_{1-6}$ alkylcarbonyl, and includes, for example, acetylamino, propionylamino, isobutyrylamino, valerylamino, isovalerylamino, pivaloylamino, etc.

"$C_{1-6}$ alkylsulfonyl" means a sulfonyl with the above-mentioned $C_{1-6}$ alkyl bonding thereto, and includes, for example, methylsulfonyl, ethylsulfonyl, n-propylsulfonyl, etc.

"$C_{1-6}$ alkylsulfonylamino" means an amino group in which one hydrogen atom is substituted with the above-mentioned $C_{1-6}$ alkylsulfonyl, and includes, for example, methylsulfonylamino, ethylsulfonylamino, n-propylsulfonylamino, etc.

"$C_{1-6}$ alkylsulfinyl" means a sulfinyl with the above-mentioned $C_{1-6}$ alkyl bonding thereto, and includes, for example, methylsulfinyl, ethylsulfinyl, n-propylsulfinyl, etc.

"Aryl" includes, for example, phenyl, naphthyl, etc.

"Heteroaryl" means a 5-membered or 6-membered monocyclic heteroaryl having one or more, preferably from 1 to 3, the same or different hetero atoms selected from a group consisting of an oxygen atom, a nitrogen atom and a sulfur atom; or a condensed cyclic heteroaryl formed through condensation of above monocyclic heteroaryl and the above-mentioned aryl, or through condensation of the same or different such monocyclic heteroaryl groups; and it includes, for example, pyrrolyl, furyl, thienyl, imidazolyl, pyrazolyl, thiazolyl, isothiazolyl, oxazolyl, isoxazolyl, triazolyl, tetrazolyl, oxadiazolyl, 1,2,3-thiadiazolyl, 1,2,4-thiadiazolyl, 1,3,4-thiadiazolyl, pyridyl, pyrazinyl, pyrimidinyl, pyridazinyl, 1,2,4-triazinyl, 1,3,5-triazinyl, indolyl, benzofuranyl, benzothienyl, benzimidazolyl, benzoxazolyl, benzisoxazolyl, benzothiazolyl, benzisothiazolyl, indazolyl, purinyl, quinolyl, isoquinolyl, phthalazinyl, naphthyridinyl, quinoxalinyl, quinazolinyl, cinnolinyl, pteridinyl, pyrido[3,2-b]pyridyl.

The above-mentioned "aryl" and "heteroaryl" may be substituted with, for example, a substituent selected from a group consisting of a hydroxy, a cyano, a halogen, a $C_{1-6}$ alkyl, a halo-$C_{1-6}$ alkyl, a $C_{3-8}$ cycloalkyl, a $C_{1-6}$ alkoxy, a halo-$C_{1-6}$ alkoxy, a $C_{3-8}$ cycloalkoxy, an amino, a $C_{1-6}$ alkylamino, a di-$C_{1-6}$ alkylamino, a halo-$C_{1-6}$ alkylamino, a di-halo-$C_{1-6}$ alkylamino, a $C_{3-8}$ cycloalkylamino, a di-$C_{3-8}$ cycloalkylamino, a carbamoyl, a $C_{1-6}$ alkylcarbamoyl, a di-$C_{1-6}$ alkylcarbamoyl, a halo-$C_{1-6}$ alkylcarbamoyl, a di-halo-$C_{1-6}$ alkylcarbamoyl, a $C_{3-8}$ cycloalkylcarbamoyl, a di-$C_{3-8}$ cycloalkylcarbamoyl, a thiol, a $C_{1-6}$ alkylthio, a halo-$C_{1-6}$ alkylthio, a $C_{3-8}$ cycloalkylthio, a $C_{1-6}$ alkylsulfinyl, a halo-$C_{1-6}$ alkylsulfinyl, a $C_{3-8}$ cycloalkylsulfinyl, a $C_{1-6}$ alkylsulfonyl a halo-$C_{1-6}$ alkylsulfonyl, a $C_{3-8}$ cycloalkylsulfonyl, a $C_{1-6}$ alkylcarbonyl, a halo-$C_{1-6}$ alkylthio, a $C_{3-8}$ cycloalkylcarbonyl, a $C_{1-6}$ alkoxycarbonyl, a halo-$C_{1-6}$ alkoxycarbonyl, a $C_{3-8}$ cycloalkoxycarbonyl, a $C_{1-6}$ alkoxycarbonylamino, a halo-$C_{1-6}$ alkoxycarbonylamino, a $C_{3-8}$ cycloalkoxycarbonylamino, a $C_{1-6}$ alkylcarbonylamino, a halo-$C_{1-6}$ alkylcarbonylamino and a $C_{3-8}$ cycloalkylcarbonylamino "Arylcarbonyl" means a group of carbonyl with the above-mentioned aryl bonding thereto.

"Heteroarylcarbonyl" means a group of carbonyl with the above-mentioned heteroaryl bonding thereto.

"Arylcarbonylamino" means an amino group in which one hydrogen atom is substituted with the above-mentioned arylcarbonyl.

"Heteroarylcarbonylamino" means an amino group in which one hydrogen atom is substituted with the above-mentioned heteroarylcarbonyl.

"Aryloxy" means a group of an oxygen atom with the above-mentioned aryl bonding thereto.

"Heteroaryloxy" means a group of an oxygen atom with the above-mentioned heteroaryl bonding thereto.

"Aryloxycarbonyl" means a group of carbonyl with the above-mentioned aryloxy bonding thereto.

"Heteroaryloxycarbonyl" means a group of carbonyl with the above-mentioned heteroaryloxy bonding thereto.

"Aryloxycarbonylamino" means an amino group in which one hydrogen atom is substituted with the above-mentioned aryloxycarbonyl.

"Heteroaryloxycarbonyl" means an amino group in which one hydrogen atom is substituted with the above-mentioned heteroaryloxycarbonyl.

"Arylsulfinyl" means a group of sulfinyl with the above-mentioned aryl bonding thereto.

"Heteroarylsulfinyl" means a group of sulfinyl with the above-mentioned heteroaryl bonding thereto.

"Arylsulfonyl" means a group of sulfonyl with the above-mentioned aryl bonding thereto.

"Heteroarylsulfonyl" means a group of sulfonyl with the above-mentioned heteroaryl bonding thereto.

"Arylsulfonylamino" means an amino group in which one hydrogen atom is substituted with the above-mentioned arylsulfonyl.

"Heteroarylsulfonylamino" means an amino group in which one hydrogen atom is substituted with the above-mentioned heteroarylsulfonyl.

"Aralkyl" means a group of the above-mentioned aryl with the above-mentioned $C_{1-6}$ alkyl bonding thereto, and includes benzyl, 1-phenylethyl, 2-phenylethyl, 1-naphthylmethyl, 2-naphthylmethyl, etc.

"Heteroaralkyl" means a group of the above-mentioned heteroaryl with the above-mentioned $C_{1-6}$ alkyl bonding thereto.

"Aralkyloxy" means a group of an oxygen atom with the above-mentioned aralkyl bonding thereto.

"Heteroaralkyloxy" means a group of an oxygen atom with the above-mentioned heteroaralkyl bonding thereto.

"Heterocyclyl" means a saturated, partially saturated or unsaturated, monocyclic or bicyclic ring containing from 4 to 10 carbon atoms and having 1, 2 or 3 hetero atoms selected from nitrogen, oxygen and sulfur atoms, in which the ring nitrogen atom may be substituted with a group selected from a $C_{1-6}$ alkyl, amino-$C_{1-6}$ alkyl, aryl, aryl-$C_{1-6}$ alkyl and acyl, and the ring carbon atom may be substituted with a $C_{1-6}$ alkyl, an amino-$C_{1-6}$ alkyl, an aryl, an aryl-$C_{1-6}$ alkyl, a heteroaryl, a $C_{1-6}$ alkoxy, a hydroxy or an oxo, and includes, for example, pyrrolidinyl, oxazolidinyl, thiazolidinyl, piperidinyl, morpholinyl, piperazinyl, dioxolanyl and tetrahydropyranyl.

"Salts" of the compounds of the invention mean ordinary, pharmaceutically-acceptable salts. For example, when the compounds have a carboxyl group, then they may form base-addition salts at the carboxyl group; or when the compounds have an amino group or a basic heterocyclic group, they may form acid-addition salts at the basic nitrogen-containing heterocyclic group.

The base-addition salts include, for example, alkali metal salts such as sodium salts, potassium salts; alkaline earth metal salts such as calcium salts, magnesium salts;

ammonium salts; and organic amine salts such as trimethylamine salts, triethylamine salts, dicyclohexylamine salts, ethanolamine salts, diethanolamine salts, triethanolamine salts, procaine salts, N,N'-dibenzylethylenediamine salts.

The acid-addition salts include, for example, inorganic acid salts such as hydrochlorides, sulfates, nitrates, phosphates, perchlorates; organic acid salts such as maleates, fumarates, tartrates, citrates, ascorbates, trifluoroacetates; and sulfonates such as methanesulfonates, isethionates, benzenesulfonates, p-toluenesulfonates.

For illustrating the compounds of the invention more concretely, the symbols used in formula (I) are described in more detail with reference to their preferred examples.

"Substitutable position" is meant to indicate the position of a hydrogen atom chemically substitutable on the carbon, nitrogen, oxygen and/or sulfur atoms of the compound, and the substitution gives a chemically stable compound.

Depending on the type of the substituent therein and on the salt form thereof, the compound of the invention may include stereoisomers and tautomers such as optical isomers, diastereomers and geometric isomers; and the compound of the invention encompasses all such stereoisomers, tautomers and their mixtures.

The invention includes various crystals, amorphous substances, salts, hydrates and solvates of the compounds of the invention.

Further, prodrugs of the compounds of the invention are within the scope of the invention. In general, such prodrugs are functional derivatives of the compounds of the invention that can be readily converted into compounds that are needed by living bodies. Accordingly, in the method of treatment of various diseases in the invention, the term "administration" includes not only the administration of a specific compound but also the administration of a compound which, after administered to patients, can be converted into the specific compound in the living bodies. Conventional methods for selection and production of suitable prodrug derivatives are described, for example, in "Design of Prodrugs", ed. H. Bundgaard, Elsevier, 1985, which is referred to herein and is entirely incorporated herein as a part of the present description. Metabolites of these compounds include active compounds that are produced by putting the compounds of the invention in a biological environment, and are within the scope of the invention.

For concretely illustrating the compounds of the invention, the symbols used in formula (I) are described below with reference to their specific examples.

W represents a $C_{1-6}$ alkyl, a $C_{3-8}$ cycloalkyl, an aryl, a heteroaryl, an aralkyl, a heteroaralkyl or —N($R^1$)($R^2$).

$R^1$ and $R^2$ each independently represent a hydrogen atom, a $C_{1-6}$ alkyl, a $C_{3-8}$ cycloalkyl, an aryl, a heteroaryl, an aralkyl or a heteroaralkyl, or $R^1$ and $R^2$, taken together with the nitrogen atom to which they bond, form a nitrogen-containing hetero ring.

The above-mentioned alkyl, cycloalkyl, aryl, heteroaryl, aralkyl, heteroaralkyl and nitrogen-containing hetero ring may be substituted with a substituent selected from a group consisting of a hydroxy, a cyano, a carboxyl, a sulfo, a halogen, a $C_{1-6}$ alkyl, a halo-$C_{1-6}$ alkyl, a $C_{3-8}$ cycloalkyl, a $C_{1-6}$ alkoxy, a halo-$C_{1-6}$ alkoxy, a hydroxy-$C_{1-6}$ alkyl, an amino-$C_{1-6}$ alkyl, a $C_{1-6}$ alkoxy-$C_{1-6}$ alkyl, an amino (the amino may be mono- or di-substituted with a $C_{1-6}$ alkyl, an aryl or a heteroaryl), a carbamoyl (the carbamoyl may be mono- or di-substituted with a $C_{1-6}$ alkyl, an aryl or a heteroaryl), a sulfanyl (the sulfanyl may be mono-substituted with a $C_{1-6}$ alkyl, an aryl or a heteroaryl), a $C_{1-6}$ alkylsulfinyl, an arylsulfinyl, a heteroarylsulfinyl, a $C_{1-6}$ alkylsulfonyl, an arylsulfonyl, a heteroarylsulfonyl, a sulfamoyl (the sulfamoyl may be mono- or di-substituted with a $C_{1-6}$ alkyl, an aryl or a heteroaryl), a $C_{1-6}$ alkylsulfonylamino, an arylsulfonylamino, a heteroarylsulfonylamino, a $C_{1-6}$ alkylcarbonyl, an arylcarbonyl, a heteroarylcarbonyl, a $C_{1-6}$ alkoxycarbonyl, an aryloxycarbonyl, a heteroaryloxycarbonyl, a carbamoylamino (the carbamoylamino may be mono- or di-substituted with a $C_{1-6}$ alkyl, an aryl or a heteroaryl), a $C_{1-6}$ alkoxycarbonylamino, an aryloxycarbonylamino, a heteroaryloxycarbonylamino, a $C_{1-6}$ alkylcarbonylamino, an arylcarbonylamino, a heteroarylcarbonylamino, an aryl, a heteroaryl, an aralkyl, a heteroaralkyl, an aralkyloxy and a heteroaralkyloxy.

Concretely, examples of W include a $C_{1-6}$ alkyl such as methyl, ethyl, n-propyl, isopropyl, n-butyl, isobutyl, n-pentyl; a $C_{3-8}$ cycloalkyl such as cyclopropyl, cyclobutyl, cyclopentyl, cyclohexyl; an aryl such as phenyl, naphthyl; a heteroaryl such as pyridyl, pyrimidinyl, pyridazinyl; an aralkyl such as benzyl, phenylethyl; a heteroaralkyl such as pyridylmethyl, pyridylethyl, pyrimidylmethyl; —N($R^1$)($R^2$) such as amino, methylamino, ethylamino. Examples of the nitrogen-containing hetero atom formed by $R^1$ and $R^2$, as taken together with the nitrogen atom to which they bond, include a 5- to 7-membered monocyclic ring such as azetidine, pyrrolidine, piperidine, azepane, morpholine; a 5- to 7-membered bicyclic ring such as 2-azabicyclo[2.2.1]heptane, 7-azabicyclo[2.2.1]heptane, 2-azabicyclo[2.2.2]octane, 3-oxo-2,3,6,7-tetrahydroisoxazolo[4,5-c]pyridine, 2-azabicyclo[2.2.1]heptane, 2-azabicyclo[2.2.2]octane, 7-azabicyclo[2.2.1]heptane, 8-azabicyclo[3.2.1]octane, hexahydropyrrolo[1,2-a]pyrazine, octahydro-2H-pyrido[1,2-a]pyrazine, 5-methyl-2,5-diazabicyclo[2.2.1]heptane, 2-oxa-5-azabicyclo[2.2.1]heptane, 1,4,6,7-tetrahydro-5H-pyrazolo[4,3-c]pyridine; a tricyclic ring such as 4-azatricyclo[4.3.1.1$^{3,8}$]undecane.

W is preferably —N($R^1$)($R^2$) such as amino, methylamino, ethylamino, cyclopropylamino; a $C_{1-6}$ alkyl; a $C_{3-8}$ cycloalkyl; an aryl such as phenyl, naphthyl; a heteroaryl such as pyridyl, pyrimidinyl, pyridazinyl; or is —N($R^1$)($R^2$) in which $R^1$ and $R^2$, as taken together with the nitrogen atom to which they bond, form a nitrogen-containing hetero ring. More preferably, W is a $C_{3-8}$ cycloalkyl; an aryl; a heteroaryl; or as a nitrogen-containing hetero ring formed by $R^1$ and $R^2$, as taken together with the nitrogen atom to which they bond, a 5- to 7-membered monocyclic ring such as pyrrolidine, piperidine, azepane, or 5- to 7-membered bicyclic ring such as 2-azabicyclo[2.2.1]heptane, octahydropyrrolo[1,2-a]pyrazine, octahydro-2H-pyrido[1,2-a]pyrazine.

X represents an aryl, a heteroaryl, an aralkyl or a heteroaralkyl, and the group may be substituted with a substituent selected from a group consisting of a hydroxy, a cyano, a carboxyl, a sulfo, a halogen, a $C_{1-6}$ alkyl, a halo-$C_{1-6}$ alkyl, a $C_{3-8}$ cycloalkyl, a $C_{1-6}$ alkoxy, a halo-$C_{1-6}$ alkoxy, a hydroxy-$C_{1-6}$ alkyl, an amino-$C_{1-6}$ alkyl, a $C_{1-6}$ alkoxy-$C_{1-6}$ alkyl, an amino (the amino may be mono- or di-substituted with a $C_{1-6}$ alkyl, an aryl or a heteroaryl), a carbamoyl (the carbamoyl may be mono- or di-substituted with a $C_{1-6}$ alkyl, an aryl or a heteroaryl), a sulfanyl (the sulfanyl may be mono-substituted with a $C_{1-6}$ alkyl, an aryl or a heteroaryl), a $C_{1-6}$ alkylsulfinyl, an arylsulfinyl, a heteroarylsulfinyl, a $C_{1-6}$ alkylsulfonyl, an arylsulfonyl, a heteroarylsulfonyl, a sulfamoyl (the sulfamoyl may be mono- or di-substituted with a $C_{1-6}$ alkyl, an aryl or a heteroaryl), a $C_{1-6}$ alkylsulfonylamino, an arylsulfonylamino, a heteroarylsulfonylamino, a $C_{1-6}$ alkylcarbonyl, an arylcarbonyl, a heteroarylcarbonyl, a $C_{1-6}$ alkoxycarbonyl, an aryloxycarbonyl, a heteroaryloxycarbonyl, a carbamoylamino (the carbamoylamino may be mono- or di-substituted with a $C_{1-6}$ alkyl, an aryl or a heteroaryl), a $C_{1-6}$ alkoxycarbonylamino, an aryloxycarbonylamino, a heteroaryloxycarbonylamino, a $C_{1-6}$ alkylcarbonylamino, an arylcarbonylamino, a heteroarylcarbonylamino, an aryl, a heteroaryl, an aralkyl, a heteroaralkyl, an aralkyloxy and a heteroaralkyloxy.

Concretely, examples of X include an aryl such as phenyl, naphthyl; a heteroaryl such as pyridyl, pyridazinyl, pyrimidinyl, imidazolyl, thiazolyl, thiadiazolyl, oxazolyl, isoxazolyl, pyrrolyl, diazolyl, triazolyl; an aralkyl such as benzyl, naphthylmethyl; a heteroaralkyl such as pyridylmethyl, pyridazinylmethyl, pyrimidinylmethyl.

Preferred examples of X includes groups of a formula (X-1), formula (X-2) or formula (X-3):

[Chemical Formula 3]

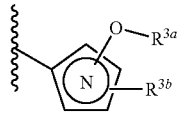

(X-1)

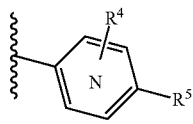

(X-2)

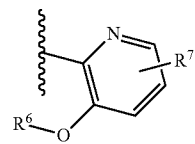

(X-3)

[wherein
$R^{3a}$ represents a hydrogen atom, a $C_{1-6}$ alkyl, a halo-$C_{1-6}$ alkyl, a $C_{3-8}$ cycloalkyl, an aryl, a heteroaryl, an aralkyl or a heteroaralkyl;
$R^{3b}$ represents a hydrogen atom, a halogen, a $C_{1-6}$ alkyl, a halo-$C_{1-6}$ alkyl, a $C_{3-8}$ cycloalkyl, an aryl, a heteroaryl, an aralkyl or a heteroaralkyl, provided that Ria-O— bonds to the carbon atom;
$R^4$ represents a hydrogen atom, a $C_{1-6}$ alkyl, a halo-$C_{1-6}$ alkyl, a $C_{3-8}$ cycloalkyl, an aryl, a heteroaryl, an aralkyl, a heteroaralkyl, a $C_{1-6}$ alkoxy, a halo-$C_{1-6}$ alkoxy, an aryloxy or a heteroaryloxy;
$R^5$ represents an isopropyl or an isopropyloxy;
$R^6$ represents a hydrogen atom or a $C_{1-6}$ alkyl,
$R^7$ represents a hydrogen atom, a $C_{1-6}$ alkyl, a halo-$C_{1-6}$ alkyl, a $C_{3-8}$ cycloalkyl, an aryl, a heteroaryl, an aralkyl, a heteroaralkyl, a $C_{1-6}$ alkoxy, a halo-$C_{1-6}$ alkoxy, an aryloxy, a heteroaryloxy, a heteroaralkyloxy, a $C_{1-6}$ alkylthio, a $C_{1-6}$ alkylsulfanyl, a $C_{1-6}$ alkylsulfonyl, an arylthio, an arylsulfanyl or an arylsulfonyl;

[Chemical Formula 4]

represents a 5-membered nitrogen-containing heteroaryl which may have from 1 to 3 nitrogen atoms, and the nitrogen-containing heteroaryl may contain an oxygen atom or a sulfur atom;

[Chemical Formula 5]

represents a 6-membered nitrogen-containing heteroaryl which may have from 1 to 3 nitrogen atoms].

As preferred examples thereof, $R^{3a}$ and $R^{3b}$ are the same or different, each representing a $C_{1-6}$ alkyl such as methyl, ethyl, n-propyl, n-butyl, n-hexyl; a $C_{3-8}$ cycloalkyl such as cyclopropyl, cyclobutyl, cyclopentyl, cyclohexyl, cycloheptyl, cyclooctyl; an aryl such as phenyl, naphthyl; a heteroaryl.

Preferably, $R^4$ is a hydrogen atom; a $C_{1-6}$ alkyl such as methyl, ethyl, n-propyl, n-butyl, n-hexyl; an aryl such as phenyl, naphthyl; a heteroaryl; a $C_{1-6}$ alkoxy such as methoxy, ethoxy, n-propyloxy, n-butoxy; an aryloxy such as phenoxy, naphthyloxy; or a heteroaryloxy.

$R^5$ is an isopropyl or an isopropyloxy.

Preferred examples of $R^6$ include a hydrogen atom, methyl, ethyl, isopropyl.

Preferred examples of $R^7$ include a hydrogen atom; a halogen such as fluorine, chlorine; a cyano; a $C_{1-6}$ alkyl such as methyl, ethyl, n-propyl, isopropyl, n-butyl; a $C_{1-6}$ alkoxy such as methoxy, ethoxy, n-propyloxy, isopropyloxy, n-butoxy; a $C_{1-6}$ alkoxyalkyl such as methoxymethyl; a halo-$C_{1-6}$ alkyl such as fluoromethyl, trifluoromethyl, chloromethyl; a hydroxy-$C_{1-6}$ alkyl such as hydroxymethyl, hydroxyethyl, 1-hydroxymethylethyl; a $C_{3-8}$ cycloalkyl such as cyclopropyl, cyclobutyl; a halo-$C_{1-6}$ alkoxy such as fluoromethoxy, trifluoromethoxy, chloromethoxy; a $C1-6$ alkylsulfinyl such as thiomethyl, thioethyl; an aryloxy such as phenoxy; an arylsulfinyl such as phenylthio; an arylsulfonyl such as phenylsulfonyl.

Specific examples of formula (X-1) include the following:

[Chemical Formula 6]

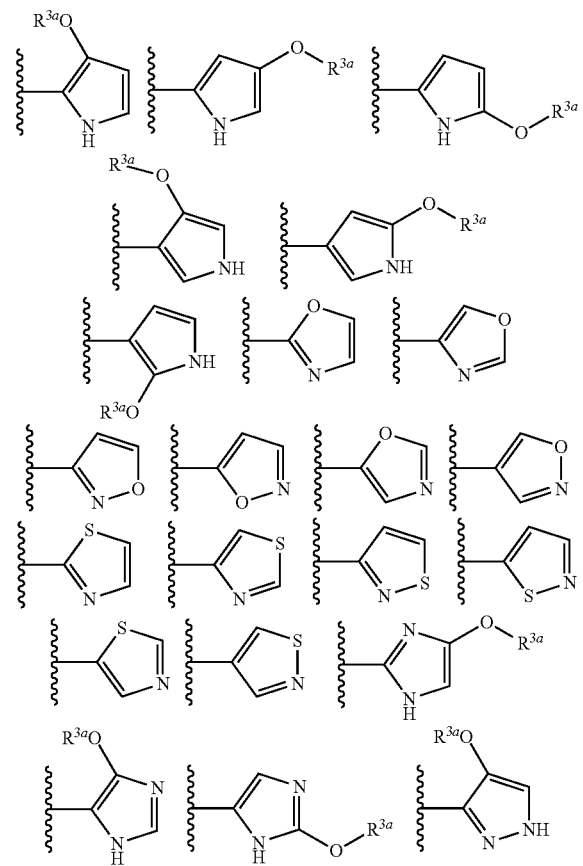

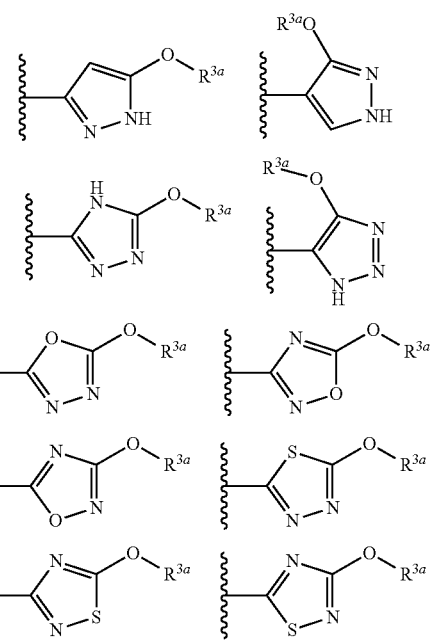

[wherein $R^{3a}$ has the same meaning as above].

Specific examples of formula (X-2) include the following:

[Chemical Formula 7]

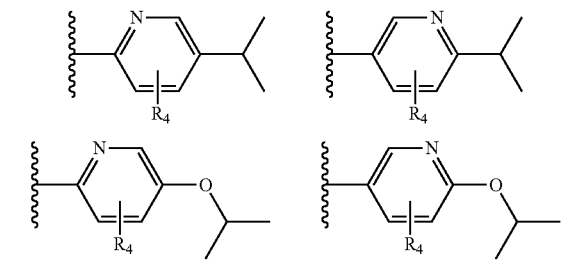

[wherein $R^4$ has the same meaning as above].

Specific examples of formula (X-3) include the following:

[Chemical Formula 8]

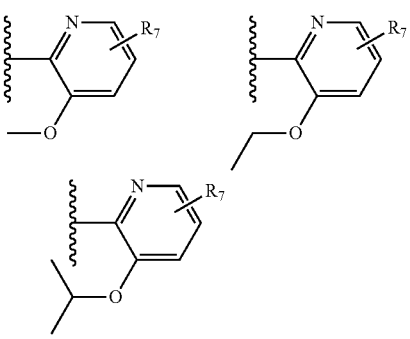

[wherein $R^7$ has the same meaning as above].

Y represents a formula (II-1), a formula (II-2), a formula (II-3) or a formula (II-4):

[Chemical Formula 9]

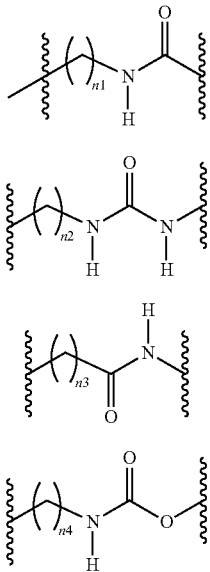

(II-1)

(II-2)

(II-3)

(II-4)

(wherein n1, n2, n3 and n4 each indicate 0 or 1).

The hydrogen atom in formula (II-1) to formula (II-4) may be substituted with a $C_{1-6}$ alkyl, a halo-$C_{1-6}$ alkyl or a $C_{3-8}$ cycloalkyl.

Y is preferably formula (II-2) or formula (II-3).

When Y is formula (II-2), X is preferably an aryl or a heteroaryl.

Z represents a hydrogen atom, a hydroxy, a cyano, a carboxyl, a sulfo, a halogen, a $C_{1-6}$ alkyl, a halo-$C_{1-6}$ alkyl, a $C_{3-8}$ cycloalkyl, a $C_{1-6}$ alkoxy, a halo-$C_{1-6}$ alkoxy, a hydroxy-$C_{1-6}$ alkyl, an amino-$C_{1-6}$ alkyl, a $C_{1-6}$ alkoxy-$C_{1-6}$ alkyl, an amino (the amino may be mono- or di-substituted with a $C_{1-6}$ alkyl, an aryl or a heteroaryl), a carbamoyl (the carbamoyl may be mono- or di-substituted with a $C_{1-6}$ alkyl, an aryl or a heteroaryl), a sulfanyl (the sulfanyl may be mono-substituted with a $C_{1-6}$ alkyl, an aryl or a heteroaryl), a $C_{1-6}$ alkylsulfinyl, an arylsulfinyl, a heteroarylsulfinyl, a $C_{1-6}$ alkylsulfonyl, an arylsulfonyl, a heteroarylsulfonyl, a sulfamoyl (the sulfamoyl may be mono- or di-substituted with a $C_{1-6}$ alkyl, an aryl or a heteroaryl), a $C_{1-6}$ alkylsulfonylamino, an arylsulfonylamino, a heteroarylsulfonylamino, a $C_{1-6}$ alkylcarbonyl, an arylcarbonyl, a heteroarylcarbonyl, a $C_{1-6}$ alkoxycarbonyl, an aryloxycarbonyl, a heteroaryloxycarbonyl, a carbamoylamino (the carbamoylamino may be mono- or di-substituted with a $C_{1-6}$ alkyl, an aryl or a heteroaryl), a $C_{1-6}$ alkoxycarbonylamino, an aryloxycarbonylamino, a heteroaryloxycarbonylamino, a $C_{1-6}$ alkylcarbonylamino, an arylcarbonylamino, a heteroarylcarbonylamino, an aryl, a heteroaryl, an aralkyl, a heteroaralkyl, an aralkyloxy or a heteroaralkyloxy.

Concretely, examples of Z include a hydrogen atom; a halogen such as fluorine, chlorine; a $C_{1-6}$ alkyl such as methyl, ethyl, n-propyl; a $C_{1-6}$ alkoxy such as methoxy, ethoxy; a $C_{1-6}$ alkylamino such as methylamino, ethylamino; a di-$C_{1-6}$ alkylamino such as dimethylamino, diethylamino; a $C_{1-6}$ alkylsulfonyl such as methylsulfonyl, ethylsulfonyl; a $C_{1-6}$ alkylsulfanyl such as methylsulfanyl, ethylsulfanyl; a $C_{1-6}$ alkylcarbonyl such as methylcarbonyl, ethylcarbonyl; a sulfamoyl; a di-$C_{1-6}$ alkylsulfamoyl such as dimethylsulfamoyl.

Z is preferably a hydrogen atom, chlorine, methyl, ethyl, methoxy or ethoxy, more preferably a hydrogen atom.

Regarding the bonding position thereof, Z preferably bonds to $A_4$.

$A_1$, $A_2$, $A_3$ and $A_4$ each independently represent CH or N, provided that at least three are CH.

Concretely, preferred examples of $A_1$, $A_2$, $A_3$ and $A_4$ include the following:

$A_1$, $A_2$ and $A_3$ are CH, and $A_4$ is N;
$A_1$, $A_2$ and $A_4$ are CH, and $A_3$ is N;
$A_1$, $A_3$ and $A_4$ are CH, and $A_2$ is N;
$A_2$, $A_3$ and $A_4$ are CH, and $A_j$ is N;
$A_1$, $A_2$, $A_3$ and $A_4$ are all CH.

More preferably, $A_1$, $A_2$, $A_3$ and $A_4$ are all CH.

Preferably, compounds of formula (I) are those of a formula (I-1):

[Chemical Formula 10]

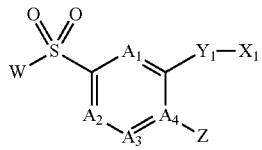

(I-1)

[wherein
$Y_1$ represents formula (II-2) or formula (II-3);
$X_1$ represents formula (X-1), formula (X-2) or formula (X-3);
W, Z, $A_1$, $A_2$, $A_3$ and $A_4$ have the same meanings as above].

Preferred examples of compounds of formula (I) include the following:

3-(2-azabicyclo [2.2.1]hept-2-ylsulfonyl)-N-(4-isopropoxyphenyl)benzamide,

3-{[3-(1H-benzimidazol-2-yl)piperidin-1-yl]sulfonyl}-N-(4-isopropoxyphenyl)benzamide, 3-{[3-(1,3-benzoxazol-2-yl)piperidin-1-yl]sulfonyl}-N-(4-isopropoxyphenyl)benzamide, 1-[(3-{[(4-isopropylphenyl)amino]carbonyl}phenyl)sulfonyl]piperidine-3-carboxamide, 3-{[3-(hydroxymethyl)piperidin-1-yl]sulfonyl}-N-(4-isopropylphenyl)benzamide, 3-(2-azabicyclo [2.2.1]hept-2-ylsulfonyl)-N-(3-methoxypyridin-2-yl)benzamide, 3-{[3-(1H-benzimidazol-2-yl)piperidin-1-yl]sulfonyl}-N-(3-methoxypyridin-2-yl)benzamide, N-benzyl-1-[(3-{[(3-methoxypyridin-2-yl)amino]carbonyl}phenyl)sulfonyl]piperidine-carboxamide, 3-isopropoxy-5-{[3-(morpholin-4-ylsulfonyl)benzoyl]amino}-1H-pyrazole hydrochloride, 3-isopropoxy-5-({3-[(2-methylpyrrolidin-1-yl)sulfonyl]benzoyl]amino)-1H-pyrazole hydrochloride, 5-[(3-{[3-(hydroxymethyl)piperidin-1-yl]sulfonyl}benzoyl)amino]-3-isopropoxy-1H-pyrazole hydrochloride, 5-({3-[(3-hydroxypiperidin-1-yl)sulfonyl]benzoyl}amino)-3-isopropoxy-1H-pyrazole hydrochloride, 5-({3-[(4-fluoropiperidin-1-yl)sulfonyl]benzoyl}amino)-3-isopropoxy-1H-pyrazole hydrochloride, 5-({3-[(4,4-difluoropiperidin-1-yl)sulfonyl]benzoyl}amino)-3-isopropoxy-1H-pyrazole hydrochloride, 3-isopropoxy-5-{[3-(piperidin-1-ylsulfonyl)benzoyl]amino}-1H-pyrazole hydrochloride, N-(3-isopropoxy-1H-pyrazol-5-yl)-3-(pyrrolidin-1-ylsulfonyl)benzamide, N-(4-isopropylphenyl)-3-(piperidin-1-ylsulfonyl)benzamide, N-(2-methoxyphenyl)-3-(piperidin-1-ylsulfonyl)benzamide, N-(4-isopropoxyphenyl)-3-(piperidin-1-ylsulfonyl)benzamide, N-(3-methoxypyridin-2-yl)-3-(piperidin-1-ylsulfonyl)benzamide, N-(6-isopropoxypyridin-3-yl)-3-(piperidin-1-ylsulfonyl)benzamide, N-(3-cyclopropyl-1H-pyrazol-5-yl)-3-(piperidin-1-ylsulfonyl)benzamide, N-(3-isopropoxy-1H-pyrazol-5-yl)-3-(pyridin-2-ylsulfonyl)benzamide, N-(3-ethoxy-1H-pyrazol-5-yl)-3-(pyridin-2-ylsulfonyl)benzamide, N-(3-propoxy-1H-pyrazol-5-yl)-3-(pyridin-2-ylsulfonyl)benzamide, N-(3-butoxy-1H-pyrazol-5-yl)-3-(pyridin-2-ylsulfonyl)benzamide, N-(cyclohexylsulfonyl)-N-(4-isopropoxyphenyl)benzamide, N-(4-isopropylphenyl)-2-methoxy-5-(piperidin-1-ylsulfonyl)benzamide, 4-isopropoxy-N-[3-(piperidin-1-ylsulfonyl)benzyl]benzamide, and N-(4-isopropylphenyl)-2-[3-(piperidin-1-ylsulfonyl)phenyl]acetamide.

Production Method for Compound of Formula (I)

The compounds of the invention can be produced, for example, according to the production methods mentioned below or according to the methods shown in Examples. However, the production methods for the compounds of the invention are not limited to these examples.

Production Method 1:

The compounds of formula (I) can be produced according to the following method.

[Chemical Formula 11]

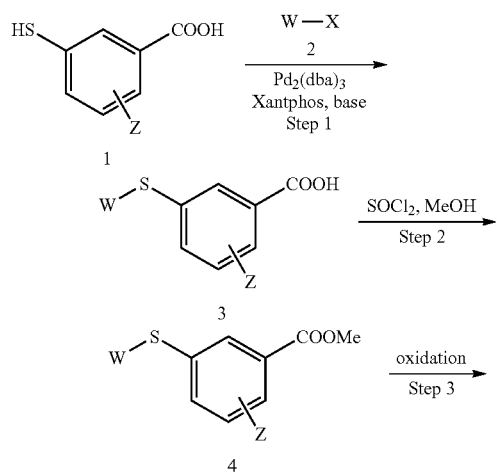

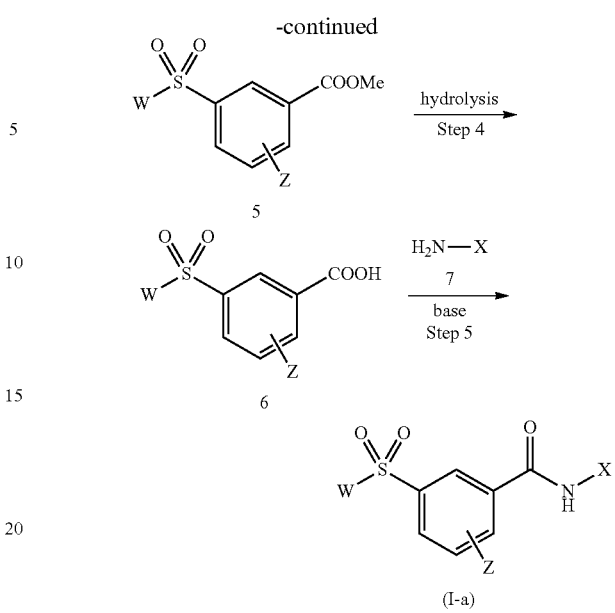

[In the formulae, each symbols have the same meanings as above.]

Step 1:

A compound 1 is reacted with a compound 2 in an organic solvent in the presence of a base, a tris(dibenzylideneacetone)dipalladium(0) (hereinafter referred to as "Pd$_2$(dba)$_3$") and (9,9-dimethyl-9H-xanthene-4,5-diyl)bis(diphenylphosphine) (hereinunder referred to as "Xantphos"), thereby giving a compound 3.

The base includes N,N-diisopropylethylamine, triethylamine, potassium carbonate, cesium carbonate, etc., preferably N,N-diisopropylethylamine. The amount of the base to be used may be from 1 to 10 mols pre mol of the compound 1, preferably from 1 to 3 mols.

The amount of the compound 2 to be used may be from 1 to 5 mols per mol of the compound 1; the amount of Pd$_2$(dba)$_3$ to be used may be from 0.1 to 1.0 mol per mol of the compound 1; and the amount of Xantphos to be used may be from 0.2 to 2.0 mols per mol of the compound 1.

The reaction solvent includes tetrahydrofuran (hereinafter referred to as "THF"), 1,4-dioxane (hereinafter referred to as "dioxane"), etc.

The reaction temperature may be from 20 to 150° C., and in general, the reaction may complete within 1 to 24 hours.

Step 2:

The compound 3 is reacted with thionyl chloride in methanol to give a compound 4.

The amount of thionyl chloride to be used may be from an equimolar amount to a large excessive molar amount relative to the compound 3, preferably from 1 to 5 mols.

The reaction temperature may be from room temperature to 60° C., preferably from 0 to 100° C., and in general, the reaction may complete within 1 to 24 hours.

The step 2 may be achived by known methyl-esterification method with diazomethane.

Step 3:

The compound 4 is oxidized to give a compound 5.

The oxidation method is not specifically defined, in which, for example, m-chloroperbenzoic acid, potassium permanganate may be used.

In case where m-chloroperbenzoic acid is used, the reaction may be achieved in a solvent such as methylene chloride, chloroform.

The amount of m-chloroperbenzoic acid to be used may be from 2 to 10 mols per mol of the compound 4, and in general, the reaction may be achieved at room temperature to for 1 to 24 hours.

On the other hand, when potassium permanganate is used, the reaction may be achieved in a mixed solvent of acetone/water. Acetic acid may be added to the reaction system.

The amount of potassium permanganate to be used may be from 2 to 6 mols per mol of the compound 4, and in general, the reaction may be achieved at room temperature for 1 to 24 hours.

The amount of acetic acid to be used may be from 1 to 10 mols per mol of the compound 4.

The reaction temperature may be from 20 to 80° C., preferably from 20 to 50° C., and in general, the reaction may complete within 1 to 24 hours.

Step 4:

The ester of compound 5 is hydrolyzed to give a compound 6. The hydrolysis is not specifically defined. For example, using an equimolar amount to an excessive molar amount of an alkali such as sodium hydroxide or potassium hydroxide, and the ester may be hydrolyzed in a lower alcohol such as methanol, ethanol.

The reaction temperature in hydrolysis may be from 0 to 100° C., preferably from 20 to 50° C., and in general, the reaction may complete within 1 to 24 hours.

Step 5:

The compound 6 is amidated with a compound 7 in the presence of a base to give a compound of formula (I-a).

The amidation may be achieved by an ordinary known method, for example, a method of reacting the compound 6 and the compound 7 in the presence of a condensing agent, or a method of activating the carboxyl acid moiety of the compound 6 in an ordinary manner to give a reactive derivative and then amidating the derivative with the compound 2. (For both methods, referred to is "Basis and Experiments of Peptide Synthesis" (Nobuo Izumiya, Maruzen, 1983).)

For example, the method of using a condensing agent is as follows.

Briefly, the compound 6 and the compound 7 are condensed in the presence of a base, using a condensing agent, thereby giving the compound of formula (I-a).

The base includes N,N-diisopropylethylamine, triethylamine, potassium carbonate, cesium carbonate, etc., preferably N,N-diisopropylethylamine. The amount of the base to be used may be from 1 to 10 mols per mol of the compound 6, preferably from 1 to 3 mols.

The amount of the compound 7 to be used may be from 1 to 3 mols per mol of the compound 6.

The condensing agent includes dicyclohexylcarbodiimide, 1-ethyl-3-(3-dimethylaminopropyl)-carbodiimide, etc.; and its amount may be from 1 to 3 mols per mol of the compound 1.

For promoting the reaction, hydroxybenzotriazole (hereinafter referred to as "HOBT") may be added to the reaction system. The amount of HOBT to be used may be from 1 to 3 mols per mol of the compound 1.

The reaction solvent includes THF, dioxane, N,N-dimethylformamide (hereinafter referred to as "DMF"), dimethyl sulfoxide (hereinafter referred to as "DMSO"), dichloromethane and their mixed solvents.

The reaction temperature may be from 20 to 100° C., preferably from 20 to 50° C., and in general, the reaction may complete within 1 to 24 hours.

The compound of formula (I-a) produced according to the above-mentioned method may be readily isolated and purified in an ordinary separation method. The method includes, for example, solvent extraction, recrystallization, column chromatography, preparative thin-layer chromatography and the like (the same shall apply hereinunder).

The compound 1 includes 3-mercaptobenzoic acid, 3-mercapto-2-methoxybenzoic acid, etc.; the compound 2 includes 2-iodopyridine, 2-bromopyridine, 2-iodopyrazine, etc.; the compound 7 includes 5-isopropoxypyridine-2-amine, 4-isopropylaniline, 1-(4-aminophenyl)ethanone, etc.

Production Method 2:

Production method 2 is a production method for compounds of formula (I-b).

[Chemical Formula 12]

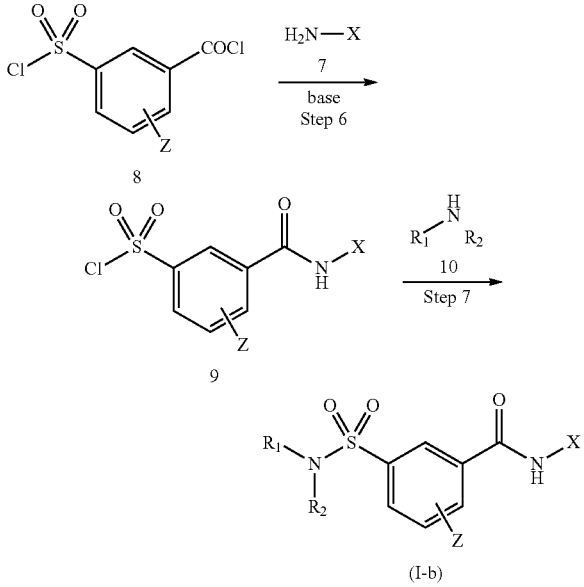

[In the formulae, each symbols have the same meanings as above.]

Step 6:

A compound 8 is amidated with a compound 7 in the presence of a base in a solvent to give a compound 9.

The base includes N,N-diisopropylethylamine, triethylamine, potassium carbonate, cesium carbonate, etc., preferably N,N-diisopropylethylamine. The amount of the base to be used may be from 1 to 10 mols per mol of the compound 8, preferably from 1 to 3 mols.

The amount of the compound 7 to be used may be from 1 to 5 mols per mol of the compound 8, preferably from 1 to 2 mols.

The organic solvent includes methylene chloride, carbon tetrachloride, THF, dioxane, DMF, DMSO, etc.

The reaction temperature may be from 0 to 80° C., preferably from 0 to 20° C., and in general, the reaction may complete within 1 to 24 hours.

The compound 7 includes 4-isopropoxyaniline, 4-isopropylaniline, 2-methoxyaniline, 4-methoxyaniline, 3-methoxypyridine-2-amine, 2-amino-5-isopropoxypyridine, etc.

Step 7:

According to the step 5, the compound 9 is condensed with a compound 10 in an organic solvent to give a compound of formula (I-b).

The amount of the compound 10 to be used may be from 1 to 5 mols per mol of the compound 9, preferably from 1 to 2 mols.

The organic solvent includes methylene chloride, carbon tetrachloride, THF, dioxane, DMF, DMSO, etc.

The reaction temperature may be from 0 to 80° C., preferably from 0 to 20° C., and in general, the reaction may complete within 1 to 24 hours.

The compound 10 includes (1R,4R)-2-oxa-5-azabicyclo[2.2.1]heptane, 2-azabicyclo[2.2.1]heptane, 4,5,6,7-tetrahydro-1H-pyrazolo[4,3-c]pyridine, 4-azatricyclo[4.3.1.1$^{3,8}$]undecane, 2-piperidin-3-yl-1H-benzimidazole, etc.

Production Method 3:

[Chemical Formula 13]

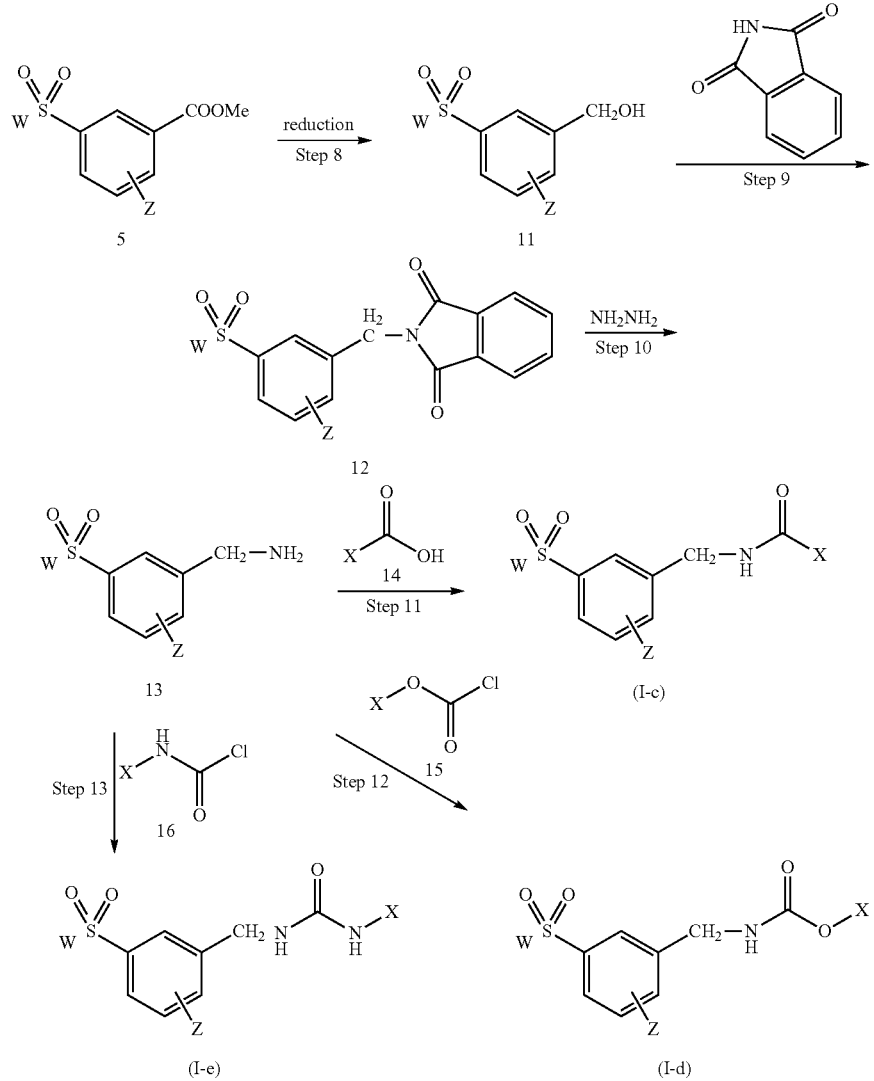

[In the formulae, each symbols have the same meanings as above.]

Step 8:

The compound 5 is reduced with a reducing agent to give a compound 11. The reduction may be achieved in any known conventional method for ester reduction, using a reducing agent such as lithiumaluminium hydride.

For example, in case where lithiumaluminium hydride is used, 1 mol of the compound 5 is reduced with from 1 to 5 mols of lithiumaluminium hydride in a reaction solvent of THF or the like, at room temperature for 1 to 6 hours to give the compound 11.

Step 9:

The compound 11 is condensed with phthalimide through Mitsunobu reaction to give a compound 12.

Specifically, in the presence of an azo compound such as dialkyl azodicarboxylate, 1,1'-(azodicarbonyl)diamide or the like and an organic phosphorus compound such as triaryl phosphine or trialkyl phosphine in a reaction solvent, the compound 11 is condensed with phthalimide to give the compound 12.

The azo compound includes dimethyl azodicarboxylate, diethyl azodicarboxylate, diisopropyl azodicarboxylate, 1,1'-(azodicarbonyl)dipiperidide, etc.; the triaryl phosphine includes triphenyl phosphine, tritolyl phosphine, etc.; the trialkyl phosphine includes triethyl phosphine, tributyl phosphine, etc. Above all, preferred is a combination of diisopropyl azodicarboxylate and triphenyl phosphine; or a combination of 1,1'-(azodicarbonyl)dipiperidide and tributyl phosphine.

The amount of phthalimide to be used may be from 1 to 10 mols per mol of the compound 11, preferably from 1 to 1.5 mols.

The amount of the azo compound and the organic phosphorus compound to be used may be from 1 to 3 mols, preferably from 1 to 1.5 mols of the azo compound per mol of the compound 11; and from 1 to 3 mols, preferably from 1 to 1.5 mols of the organic phosphorus compound per mol of phthalimide.

The reaction solvent includes carbon halides such as methylene chloride, chloroform, dichloroethane, carbon tetrachloride; aliphatic hydrocarbons such as n-heptane, n-hexane; aromatic hydrocarbons such as benzene, toluene, xylene; ethers such as diethyl ether, THF, dioxane, ethylene glycol dimethyl ether; esters such as methyl acetate, ethyl acetate; acetonitrile, N-methylpyrrolidone (hereinafter referred to as "NMP"), DMF, DMSO; or their mixed solvents, etc.

The reaction temperature may be from 0 to 100° C., preferably from 0 to 50° C., and in general, the reaction may complete within 2 to 24 hours.

Step 10:

The compound 12 is treated with hydrazine in a reaction solvent to give a compound 13.

The amount of hydrazine to be used may be from 1 to 10 mols per mol of the compound 12, preferably from 2 to 5 mols.

The reaction solvent includes methanol, ethanol, n-propanol, etc.

The reaction temperature may be from 0 to 80° C., preferably from 0 to 50° C., and in general, the reaction may complete within 1 to 24 hours.

Step 11:

The compound 13 is reacted with a compound 14 according to the step 5 to give a compound of formula (I-c).

Step 12:

The compound 13 is reacted with a compound 15 according to the step 6 to give a compound of formula (I-d).

Step 13:

The compound 13 is reacted with a compound 16 according to the step 6 to give a compound of formula (I-e).

In the above reaction, when the reactants have an amino group, a carboxyl group or the like not participating in the reaction, then the amino group or the carboxyl group may be suitably protected with a protective group for the amino group or a protective group for the carboxyl group, and the protective group may be removed after the reaction.

"Amino-protective group" includes an aralkyl such as benzyl, p-methoxybenzyl, trityl; a $C_{1-6}$ alkanoyl such as formyl, acetyl, propionyl, butyryl, pivaloyl; benzoyl; an arylalkanoyl such as phenylacetyl, phenoxyacetyl; a $C_{1-6}$ alkoxycarbonyl such as methoxycarbonyl, ethoxycarbonyl, tert-butoxycarbonyl; an aralkyloxycarbonyl such as benzyloxycarbonyl, p-nitrobenzyloxycarbonyl; a $C_{1-6}$ alkylsilyl such as trimethylsilyl, tert-butyldimethylsilyl; and especially preferred are acetyl, pivaloyl, benzoyl, ethoxycarbonyl and tert-butoxycarbonyl.

"Carboxyl-protective group" includes a $C_{1-6}$ alkyl such as methyl, ethyl, propyl, isopropyl, tert-butyl; a $C_{1-6}$ haloalkyl such as 2,2,2-trichloroethyl; a $C_{1-6}$ alkenyl such as 2-propenyl; an aralkyl such as benzyl, p-methoxybenzyl, p-nitrobenzyl, benzhydryl, trityl; and especially preferred are methyl, ethyl, tert-butyl, 2-propenyl, benzyl, p-methoxybenzyl, benzhydryl.

The protective group may be introduced and removed according to the methods described in the above-mentioned reference, "Protective Groups in Organic Synthesis" or according to methods similar thereto.

The thus-produced compound of formula (I-a), (I-b), (I-c), (I-d) or (I-e) may be readily isolated and purified in an ordinary separation method. The method includes, for example, solvent extraction, recrystallization, column chromatography, preparative thin-layer chromatography and the like.

The compounds may be converted into their pharmaceutically-acceptable salts in an ordinary manner; and on the contrary, the salts may also be converted into free compounds in an ordinary manner.

The compounds of the invention can be administered orally or parenterally, and after formulated into preparations suitable to such administration modes, the compounds can be used as preventives or remedies, for example, for circular system disorders such as hypertension, angina pectoris, heart failure, myocardial infarction, stroke, claudication, diabetic nephropathy, diabetic retinopathy, reduced vision, electrolytic abnormality, atherosclerosis, etc.; central nervous system disorders such as bulimia, diabetic neuropathy, etc.; metabolic disorders such as metabolic syndrome, obesity, diabetes, insulin resistance, hyperlipidemia, hypercholesterolemia, hypertriglyceridemia, dyslipidemia, non-alcoholic fatty liver, hormone secretion abnormality, gout, fatty liver, etc.; reproduction system disorders such as menstrual abnormality, sexual dysfunction, etc.; digestive system disorders such as hepatic dysfunction, pancreatitis, cholecystitis, gastroesophageal reflux, etc.; respiratory system disorders such as obesity hypoventilation syndrome (Pickwickian syndrome), sleep apnea syndrome, etc.; infectious disorders caused by bacteria, fungi, parasites; malignant neoplasm; inflammatory disorders such as arthritis, skin ulcer, etc.

Another aspect of the invention is to provide a therapeutical method or a preventive method for disorders, diseases or conditions caused by LCE dysmodulation, which comprises administering a therapeutically or preventively effective amount of a compound of the invention to in need thereof Still another aspect of the invention is to a therapeutical method or a preventive method for metabolic syndrome, fatty liver, hyperlipidemia, dyslipidemia, non-alcoholic fatty liver, obesity, diabetes, bulimia, malignant neoplasm or infectious disorders, which comprises administering a therapeutically or preventively effective amount of a compound of the invention to in need thereof.

Still another aspect of the invention is to provide a therapeutical method or a preventive method for diabetes, which comprises administering a therapeutically or preventively effective amount of a compound of the invention to in need thereof Still another aspect of the invention is to provide a therapeutical method or a preventive method for obesity, which comprises administering a therapeutically or preventively effective amount of a compound of the invention to in need thereof.

Still another aspect of the invention is to provide a therapeutical method or a preventive method for obesity-related disorders selected from overeating, bulimia, hypertension, plasma insulin increase, insulin resistance, hyperlipidemia, endometrial cancer, breast cancer, prostate cancer, colon cancer, renal cancer, osteoarthritis, obstructive sleep apnea syndrome, heart disease, abnormal hear beat rhythm, cardiac arrhythmia, myocardial infarction, congestive heart failure, coronary artery heart disease, sudden death, stroke, polycystic ovary, craniopharyngoima, metabolic syndrome, insulin resistance syndromes, sexual function and reproduction function failure, infertility, hypogonadism, hirsutism, obesity-related gastroesophageal reflux, obesity hypoventilation syndrome (Pickwickian syndrome), inflammations, systemic vasculitis, atherosclerosis, hypercholesterolemia, hyperuricemia, low back pain, inflammations, systemic vasculitis, atherosclerosis, hypercholesterolemia, hyperuricemia, low back pain, gallbladder disease, gout, constipation, irritable bowel syndrome, hear hypertrophy and left ventricular dilatation, which method comprises administering a therapeutically or preventively effective amount of a compound of the invention to in need thereof.

Still another aspect of the invention is to provide a therapeutical method or a preventive method for hyperlipidemia or dyslipidemia, which comprises administering a therapeutically or preventively effective amount of a compound of the invention to in need thereof.

Still another aspect of the invention is to provide a method of calorie intake, which comprises administering a therapeutically or preventively effective amount of a compound of the invention to in need thereof.

Still another aspect of the invention is to provide a method of reducing food intake, which comprises administering a therapeutically or preventively effective amount of a compound of the invention to in need thereof Still another aspect of the invention is to provide a method of increasing a satiety, which comprises administering a therapeutically or preventively effective amount of a compound of the invention to in need thereof Still another aspect of the invention is to provide a method of appetite reduction, which comprises administering a therapeutically or preventively effective amount of a compound of the invention to in need thereof The invention also relates to a therapeutical method or a preventive method for obesity, which comprises administering a compound of the invention as combined with a therapeutically or preventively effective amount of any other drug known useful for therapy or prevention for the condition.

The invention also relates to a therapeutical method or a preventive method for diabetes, which comprises administering a compound of the invention as combined with a therapeutically or preventively effective amount of any other drug known useful for therapy or prevention for the condition.

The invention also relates to a therapeutical method or a preventive method for hyperlipidemia or dyslipidemia, which comprises administering a compound (1) or a pharmaceutically-acceptable salt thereof of the invention as combined with a therapeutically or preventively effective amount of any other drug known useful for therapy or prevention for the condition.

Still another aspect of the invention is to provide a pharmaceutical composition containing a compound of the invention and a pharmaceutically-acceptable carrier.

Still another aspect of the invention relates to a compound of the invention for use as medicines.

Still another aspect of the invention relates to use of a compound of the invention for production of medicaments useful for remedy, prevention or inhibition of LCE-caused disorders for in need thereof.

Still another aspect of the invention relates to use of a compound of the invention for production of medicaments useful for remedy or prevention for metabolic syndrome, hyperlipidemia, dyslipidemia, non-alcoholic fatty liver, obesity, diabetes, bulimia, malignant neoplasm or infectious disorders for in need thereof.

Still another aspect of the invention relates to use of a compound of the invention for production of medicaments useful for remedy or prevention for obesity for in need thereof Still another aspect of the invention relates to use of a compound of the invention for production of medicaments useful for remedy or prevention for diabetes for in need thereof Still another aspect of the invention relates to use of a compound of the invention for production of medicaments useful for remedy or prevention for hyperlipidemia or dyslipidemia for in need thereof.

Still another aspect of the invention relates to use of a therapeutically effective amount of a compound of the invention and a therapeutically-effective amount of a drug or a pharmaceutically-acceptable salt thereof selected from a group consisting of insulin resistance relievers, insulin analogues, sulfonylureas, α-glucosidase inhibitors, dipeptidylpeptidase 4 (DPP-4 or DP-IV) inhibitors, glucagon-like peptide 1 (GLP-1) agonists, HMG-CoA reductase inhibitors, serotonin-like substances, β3-adrenalin receptor agonists, neuropeptide Y1 antagonists, neuropeptide Y2 agonists, neuropeptide Y5 antagonists, pancreatic lipase inhibitors, cannabinoid CB1 receptor antagonists or inverse agonists, melanine concentration hormone receptor agonists, melanocortin 4 receptor agonists, bombesin receptor sub-type 3 agonists, ghrelin antagonists, PYY, $PYY_{3-36}$ and NK-1 antagonists, which is for use for production of medicaments useful for therapy, control and prevention for obesity, diabetes, diabetes-related disorders or obesity-related disorders for in need thereof Still another aspect of the invention relates to use of a therapeutically effective amount of a compound of the invention and a therapeutically-effective amount of a drug or a pharmaceutically-acceptable salt thereof selected from a group consisting of insulin resistance relievers, insulin analogues, sulfonylureas, α-glucosidase inhibitors, dipeptidylpeptidase 4 (DPP-4 or DP-IV) inhibitors, glucagon-like peptide 1 (GLP-1) agonists, HMG-CoA reductase inhibitors, serotonin-like substances, β3-adrenalin receptor agonists, neuropeptide Y1 antagonists, neuropeptide Y2 agonists, neuropeptide Y5 antagonists, pancreatic lipase inhibitors, cannabinoid CB1 receptor antagonists or inverse agonists, melanine concentration hormone receptor agonists, melanocortin 4 receptor agonists, bombesin receptor sub-type 3 agonists, ghrelin antagonists, PYY, $PYY_{3-36}$ and NK-1 antagonists, which is for use for production of medicaments useful for therapy, or prevention for obesity, diabetes, diabetes-related disorders or obesity-related disorders and wherein an effective amount of the compound of the invention and an effective amount of the above-mentioned medicine are used at the same time or at different times.

Still another aspect of the invention relates to a product as a mixture of a therapeutically effective amount of a compound of the invention and a therapeutically-effective amount of a drug or a pharmaceutically-acceptable salt thereof selected from a group consisting of insulin resistance relievers, insulin analogues, sulfonylureas, α-glucosidase inhibitors, dipeptidylpeptidase 4 (DPP-4 or DP-IV) inhibitors, glucagon-like peptide 1 (GLP-1) agonists, HMG-CoA reductase inhibitors, serotonin-like substances, β3-adrenalin receptor agonists, neuropeptide Y1 antagonists, neuropeptide Y2 agonists, neuropeptide Y5 antagonists, pancreatic lipase inhibitors, cannabinoid CB1 receptor antagonists or inverse agonists, melanine concentration hormone receptor agonists, melanocortin 4 receptor agonists, bombesin receptor sub-type 3 agonists, ghrelin antagonists, PYY, $PYY_{3-36}$ and NK-1 antagonists, which is for simultaneous, separate or continuous use thereof for obesity, diabetes, diabetes-related disorders or obesity-related disorders.

Still another aspect of the invention relates to use of a therapeutically effective amount of a compound of the invention and a therapeutically-effective amount of a drug or a pharmaceutically-acceptable salt thereof selected from a group consisting of simvastatin, mevastatin, ezetimibe, atorvastatin, sitagliptin, metformin, sibutramine, orlistat, Qnexa (trade name) and phentermine, which is for use for production of medicaments useful for remedy, control or prevention for obesity, diabetes, diabetes-related disorders or obesity-related disorders for in need thereof.

In clinical use of the compounds of the invention, pharmaceutically-acceptable additives may be added thereto, and after formulated into preparations suitable to their administration modes, the preparations can be administered. As the additives, usable are various additives generally used in the field of pharmaceutical preparations. For example, they include gelatin, lactose, white sugar, titanium oxide, starch, crystalline cellulose, methylated cellulose, hydroxypropylmethyl cellulose, carboxymethyl cellulose, corn starch, microcrystalline wax, white vaseline, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, palmitoleic acid, light silicic anhydride, talc, vegetable oil, benzyl alcohol, gum arabic, propylene glycol, polyalkylene glycol, cyclodextrin, hydroxypropylcyclodextrin, etc.

The preparations to be formulated as a mixture with the additive include, for example, solid preparations such as tablets, capsules, granules, powders, suppositories; and liquid preparations such as syrups, elixirs, injections. These can be prepared according to ordinary methods in the filed of pharmaceutical preparations. The liquid preparations may be in such a form that is dissolved or suspended in water or in any other suitable medium before use. Especially for injections, the preparation may be dissolved or suspended, if desired, in a physiological saline or glucose solution, and a buffer and a preservative may be added thereto.

The compounds of the invention are effective for animals and plants including humans and other mammals that require treatment with the compound. The mammals are preferably humans and may be men or women. Example of mammals other than humans include, for example, companion animals such as dogs, cats. The compounds of the invention are effective for obesity and obesity-related disorders of those dogs, cats, etc. Ordinary physicians, veterinarians and clinicians may readily determine the necessity of treatment with a compound of the invention.

In the case of using the compound of the invention for, e.g., a clinical purpose, the dose and administration frequency may vary depending on the sex, age, body weight, conditions of the patient, the type and range of the required treatment using the compound, and so on. In oral administration, the dose of the compound may be from 0.01 to 100 mg/kg of adult/day (preferably from 0.03 to 1 mg/kg of adult/day) and the administration frequency is preferably from one to several times. In parenteral administration, the dose may be from 0.001 to 10 mg/kg of adult/day (preferably from 0.001 to 0.1 mg/kg of adult/day, more preferably from 0.01 to 0.1 mg/kg of adult/day) and the administration frequency is preferably from one to several times.

For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient, since the dose is to be adjusted depending on the conditions of the patient to be treated. The compounds may be administered on a regimen of 1 to 4 times per day, preferably once or twice per day.

In the case of using the compounds of the invention for treating or preventing obesity and/or diabetes and/or hyperlipemia and/or dyslipidemia and/or non-alcoholic fatty liver or other diseases, satisfactory results can be generally obtained by administering the compounds of the invention in a daily dosage of from about 0.1 mg to about 100 mg per kilogram of animal body weight, preferably in a single daily dose or in divided doses two to six times a day, or as sustained release preparations. In the case of many large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic effects.

Ordinary physicians, veterinarians and clinicians may readily determine and apply an effective dose necessary for treating, preventing, inhibiting, retarding or suppressing the development of diseases.

The preparation may contain a compound of the invention in a ratio of from 1.0 to 100% by weight, preferably from 1.0 to 60% by weight of all the ingredients constituting it. The preparation may also contain any other therapeutically-effective compound.

The compounds of the invention may be used as combined with any other agent useful for treatment of diseases, for example, circular system disorders such as hypertension, angina pectoris, heart failure, myocardial infarction, stroke, claudication, diabetic nephropathy, diabetic retinopathy, reduced vision, electrolytic abnormality, atherosclerosis, etc.; central nervous system disorders such as bulimia, diabetic neuropathy, etc.; metabolic disorders such as metabolic syndrome, obesity, diabetes, insulin resistance, hyperlipidemia, hypercholesterolemia, hypertriglyceridemia, dyslipidemia, non-alcoholic fatty liver, hormone secretion abnormality, gout, fatty liver, etc.; reproduction system disorders such as menstrual abnormality, sexual dysfunction, etc.; digestive system disorders such as hepatic dysfunction, pancreatitis, cholecystitis, gastroesophageal reflux, etc.; respiratory system disorders such as obesity hypoventilation syndrome (Pickwickian syndrome), sleep apnea syndrome, etc.; infectious disorders caused by bacteria, fungi, parasites; malignant neoplasm; inflammatory disorders such as arthritis, skin ulcer, etc. The individual ingredients of those combinations may be administered at different times or at the same time during the period of treatment, as divided preparations or as a single preparation. Accordingly, the invention should be interpreted to encompass all administration modes at the same time or at different times, and the administration in the invention should be interpreted so. The scope of the combination of the compound of the invention and the other agent useful for the above-mentioned diseases encompasses, in principle, any and every combination with any and every pharmaceutical preparation useful for the above-mentioned diseases.

The above-mentioned combination includes not only a composition of the invention containing only one other active substance but also a combination containing 2 or more other active substances. There are many examples of the combinations of the composition of the invention with one or more active substances selected from the remedial medicines for the above-mentioned diseases. For example, for the purpose of treatment, control and prevention for metabolic syndrome, the composition of the invention may be combined effectively with 1 or more active substances selected from remedies for hyperlipidemia, remedies for lipid lowering agents and antidiabetes. In particular, a composition containing an anti-obesity remedy or an anti-hypertension remedy in addition to an anti-diabetes remedy and/or a remedy for hyperlipidemia or a remedy for lipid lowering agents exhibits a synergistic effect for treatment, control or prevention of metabolic syndrome.

The drugs that may be combined with the composition of the invention include, for example, ACAT inhibitors, α-blockers, aldose reductase inhibitors, α-amylase inhibitors, angiotensin converting enzyme inhibitors, angiotensin receptor antagonists, anion exchange resins, anorectics, antioxidants, antiplatelet drugs, β-blockers, biguanide agents, calcium antagonists, CB1 receptor inverse agonists/antagonists, CETP inhibitors, cholesterol absorption inhibitors, DGAT inhibitors, DP-IV inhibitors, diuretics, eicosapentaenoic acid, endothelin inhibitors, FLAP inhibitors, FXR modulators, ghrelin antagonists, GLP-1 agonists, GLP-1 secretory agents, glucagon antagonists, glucokinase activators, glucocorticoid receptor ligands, α-glucosidase inhibitors, GPAT inhibitors, histamine H3 receptor ligands, HMG-CoA reductase inhibitors, HSD inhibitors, insulin and its analogues, kinase inhibitors such as VEGF inhibitors/PDFG inhibitors, reptin, lipase inhibitors, 5-LO inhibitors, LXR ligands, melanocortin agonists, MCH antagonists, MTTP inhibitors, olexin antagonists, opioid antagonists, neuropeptide Y antagonists, nicotinic acid agonists, PPAR ligands, PTP-1B inhibitors, SCD-1 inhibitors, serotonin transporter inhibitors, SGLT inhibitors, SUR ligands, thyroid hormone agonists, UCP activators, VPAC receptor agonists, etc.

Advantages of the Invention

The compounds of the invention have an excellent LCE-inhibitory effect, and are useful as remedies for LCE-related various diseases, for example, circular system disorders, nervous system disorders, metabolic disorders, reproduction system disorders, digestive system disorders, neoplasm, infectious diseases, etc., or as herbicides.

BEST MODE FOR CARRYING OUT THE INVENTION

The invention is described more concretely with reference to Reference Examples and Examples given below, by which, however, the invention should not be limited at all.

EXAMPLES

In thin-layer chromatography, Silica Gel$_{60}$F$_{254}$ (Merck) was used for the plate, and a UV detector was used for detection. Wakogel™ C-300 or C-200 (Wako Pure Chemical Industries), FLASH+Cartridge (Biotage) or Chromatorex (Fuji Silysia Chemical) was used for column silica gel. In MS spectrometry, used was ZQ2000 (Waters). In NMR spectrometry, dimethylsulfoxide was used as the internal standard in a heavy dimethylsulfoxide solution; a spectrometer of JNM-AL 400 (JEOL), Mercury 400 (400 MHz; Varian) or Inova 400 (400 MHz; Varian) was used; and all δ values are shown by ppm.

The meanings of the abbreviations in NMR analysis are mentioned below.
s: singlet
d: doublet
dd: double doublet
t: triplet
dt: double triplet
q: quartet
m: multiplet
br: broad
J: coupling constant
Hz: hertz
DMSO-d$_6$: heavy dimethylsulfoxide Example 1

N-(4-isopropoxyphenyl)-3-[(1R,4R)-2-oxa-5-azabicyclo[2.2.1]hept-5-ylsulfonyl]benzamide (1R,4R)-2-oxa-5-azabicyclo[2.2.1]heptane monohydrochloride (76.6 mg) and triethylamine (0.16 mL) were added in that order to a THF (3.0 mL) solution of the compound (80.0 mg) obtained in Reference Example 1, and stirred overnight at room temperature. Ethyl acetate was added to the reaction liquid, then washed three times with water, and dried with sodium sulfate. Sodium sulfate was removed through filtration, and the solvent was evaporated off under reduced pressure. The residue was purified through silica gel column chromatography (NH Biotage column, ethyl acetate/hexane=from 0% to 80%, gradient) to give the entitled compound (80.0 mg, 85%) as a white crystal.

$^1$H-NMR (CDCl$_3$) δ: 1.23-1.39 (7H, m), 1.66-1.78 (1H, m), 3.19 (1H, d, J=9.8 Hz), 3.38 (1H, d, J=9.8 Hz), 3.65 (1H, d, J=7.8 Hz), 3.82 (1H, d, J=7.8 Hz), 4.41-4.59 (3H, m), 6.88 (2H, d, J=8.8 Hz), 7.54 (2H, d, J=8.8 Hz), 7.63 (1H, t, J=7.8 Hz), 7.95 (1H, d, J=7.8 Hz), 8.13 (1H, d, J=7.8 Hz), 8.26 (1H, s), 8.29 (1H, s)

Example 2

3-(2-Azabicyclo[2.2.1]hept-2-ylsulfonyl)-N-(4-isopropoxyphenyl)benzamide

The entitled compound was produced according to the method of Example 1 but using the compound obtained in Reference Example 1 and 2-azabicyclo[2.2.1]heptane as the starting materials.

$^1$H-NMR (CDCl$_3$) δ: 0.95-1.04 (1H, m), 1.18-1.27 (1H, m), 1.34 (6H, d, J=6.3 Hz), 1.53-1.66 (3H, m), 1.69-1.78 (1H, m), 2.49 (1H, s), 3.01-3.13 (2H, m), 4.22 (1H, s), 4.49-4.57 (1H, m), 6.90 (2H, d, J=8.8 Hz), 7.56 (2H, d, J=8.8 Hz), 7.64 (1H, t, J=7.8 Hz), 7.97 (1H, d, J=7.8 Hz), 8.03 (1H, s), 8.14 (1H, d, J=7.8 Hz), 8.26 (1H, s)

Example 3

N-(4-isopropoxyphenyl)-3-(1,4,6,7-tetrahydro-5H-pyrazolo[4,3-c]pyridin-5-ylsulfonyl)benzamide trifluoroacetate The entitled compound was produced according to the method of Example 1 but using the compound obtained in Reference Example 1 and 4,5,6,7-tetrahydro-1H-pyrazolo[4,3-c]pyridine as the starting materials.

$^1$H-NMR (CDCl$_3$) δ: 1.35 (6H, d, J=5.9 Hz), 2.80-2.87 (2H, m), 3.50-3.56 (2H, m), 4.31 (2H, s), 4.50-4.58 (1H, m), 6.92 (2H, d, J=8.8 Hz), 7.35 (1H, s), 7.53 (2H, d, J=8.8 Hz), 7.63-7.69 (1H, m), 7.76-7.80 (1H, m), 7.96-8.01 (1H, m), 8.08-8.12 (1H, m), 8.22-8.25 (1H, m)

Example 4

3-(4-Azatricyclo[4.3.1.1³,⁸]undec-4-ylsulfonyl)-N-(4-isopropoxyphenyl)benzamide

The entitled compound was produced according to the method of Example 1 but using the compound obtained in Reference Example 1 and 4-azatricyclo[4.3.1.1³,⁸]undecane as the starting materials.

¹H-NMR (CDCl₃) δ: 1.34 (6H, d, J=6.3 Hz), 1.39-1.63 (7H, m), 1.76-1.96 (6H, m), 2.21-2.29 (1H, m), 3.41-3.47 (2H, m), 4.40-4.46 (1H, m), 4.49-4.58 (1H, m), 6.91 (2H, d, J=8.8 Hz), 7.55 (2H, d, J=8.8 Hz), 7.64 (1H, t, J=7.8 Hz), 7.92-8.00 (2H, m), 8.11 (1H, d, J=7.8 Hz), 8.26 (1H, s)

Example 5

3-{[3-(1H-benzimidazol-2-yl)piperidin-1-yl]sulfonyl}-N-(4-isopropoxyphenyl)benzamide The entitled compound was produced according to the method of Example 1 but using the compound obtained in Reference Example 1 and 2-piperidin-3-yl-1H-benzimidazole as the starting materials.

¹H-NMR (CDCl₃) δ: 1.28 (6H, d, J=5.9 Hz), 1.36-1.50 (1H, m), 1.60-1.78 (2H, m), 2.00-2.10 (1H, m), 2.27-2.39 (1H, m), 2.83-2.94 (1H, m), 3.34-3.48 (2H, m), 3.89-3.98 (1H, m), 4.40-4.48 (1H, m), 6.76 (2H, d, J=8.8 Hz), 7.31-7.37 (2H, m), 7.41 (1H, t, J=8.0 Hz), 7.50 (2H, d, J=8.8 Hz), 7.53-7.58 (2H, m), 7.61 (1H, d, J=8.0 Hz), 7.99 (1H, d, J=8.0 Hz), 8.09 (1H, s)

Example 6

3-{[(dicyclopropylmethyl)amino]sulfonyl}-N-(4-isopropoxyphenyl)benzamide

The entitled compound was produced according to the method of Example 1 but using the compound obtained in Reference Example 1 and 1,1-dicyclopropylmethaneamine as the starting materials.

¹H-NMR (CDCl₃) δ: 0.06-0.16 (2H, m), 0.21-0.33 (4H, m), 0.41-0.50 (2H, m), 0.75-0.86 (2H, m), 1.34 (6H, d, J=5.9 Hz), 4.49-4.56 (1H, m), 4.99 (1H, d, J=7.0 Hz), 6.89 (2H, d, J=9.0 Hz), 7.54 (2H, d, J=9.0 Hz), 7.60 (1H, t, J=7.8 Hz), 8.00-8.05 (2H, m), 8.10 (1H, d, J=7.8 Hz), 8.37-8.39 (1H, m)

Example 7

3-{[3-(1,3-benzoxazol-2-yl)piperidin-1-yl]sulfonyl}-N-(4-isopropoxyphenyl)benzamide The entitled compound was produced according to the method of Example 1 but using the compound obtained in Reference Example 1 and 2-piperidin-3-yl-1,3-benzoxazole as the starting materials.

¹H-NMR (CDCl₃) δ: 1.34 (6H, d, J=6.3 Hz), 1.63-1.76 (1H, m), 1.76-1.90 (1H, m), 1.91-2.00 (1H, m), 2.25-2.33 (1H, m), 2.46-2.57 (1H, m), 2.75-2.84 (1H, m), 3.24-3.35 (1H, m), 3.78-3.88 (1H, m), 4.16-4.24 (1H, m), 4.49-4.58 (1H, m), 6.91 (2H, d, J=7.8 Hz), 7.29-7.35 (2H, m), 7.47-7.57 (3H, m), 7.62-7.71 (2H, m), 7.79-7.85 (1H, m), 7.93-7.98 (1H, m), 8.11-8.17 (1H, m), 8.22 (1H, s)

Example 8

N-(4-isopropoxyphenyl)-3-{[(1S,4S)-5-methyl-2,5-diazabicyclo[2.2.1]hept-2-yl]sulfonyl}benzamide trifluoroacetate The entitled compound was produced according to the method of Example 1 but using the compound obtained in Reference Example 1 and (1S,4S)-2-methyl-2,5-diazabicyclo[2.2.1]heptane as the starting materials.

¹H-NMR (CDCl₃) δ: 1.17-4.32 (8H, m), 1.33 (6H, d, J=6.3 Hz), 2.83 (3H, s), 4.46-4.56 (1H, m), 6.82-6.91 (2H, m), 7.48-7.69 (3H, m), 7.92-8.00 (1H, m), 8.12-8.19 (1H, m), 8.31 (1H, s)

Example 9

N-(4-isopropoxyphenyl)-3-{[2-(phenoxymethyl)morpholin-4-yl]sulfonyl}benzamide

The entitled compound was produced according to the method of Example 1 but using the compound obtained in Reference Example 1 and 2-(phenoxymethyl)morpholine as the starting materials.

¹H-NMR (CDCl₃) δ: 1.34 (6H, d, J=6.3 Hz), 2.33-2.41 (1H, m), 2.48-2.58 (1H, m), 3.57-3.64 (1H, m), 3.70-3.84 (2H, m), 3.87-4.03 (4H, m), 4.49-4.57 (1H, m), 6.84-6.92 (4H, m), 6.93-6.98 (1H, m), 7.24-7.30 (2H, m), 7.53 (2H, d, J=8.6 Hz), 7.69 (1H, t, J=7.8 Hz), 7.87-7.94 (2H, m), 8.16 (1H, d, J=7.8 Hz), 8.20 (1H, s)

Example 10

N-(4-isopropoxyphenyl)-3-[(1S,4S)-2-oxa-5-azabicyclo[2.2.1]hept-5-ylsulfonyl]benzamide The entitled compound was produced according to the method of Example 1 but using the compound obtained in Reference Example 1 and (1S,4S)-2-oxa-5-azabicyclo[2.2.1]heptane as the starting materials.

¹H-NMR (CDCl₃) δ: 1.34 (6H, d, J=6.3 Hz), 1.62-1.69 (1H, m), 1.71-1.77 (1H, m), 3.19-3.25 (1H, m), 3.41 (1H, d, J=9.8 Hz), 3.68 (1H, dd, J=7.8, 1.6 Hz), 3.85 (1H, d, J=7.8 Hz), 4.47-4.57 (3H, m), 6.90 (2H, d, J=9.0 Hz), 7.54 (2H, d, J=9.0 Hz), 7.66 (1H, t, J=7.8 Hz), 7.98 (1H, d, J=7.8 Hz), 8.01 (1H, s), 8.14 (1H, d, J=7.8 Hz), 8.29 (1H, s)

Example 11

N-(4-isopropoxyphenyl)-3-{[3-(4-methyl-4H-1,2,4-triazol-3-yl)piperidin-1-yl]sulfonyl}benzamide trifluoroacetate The entitled compound was produced according to the method of Example 1 but using the compound obtained in Reference Example 1 and 3-(4-methyl-4H-1,2,4-triazol-3-yl)piperidine as the starting materials.

¹H-NMR (CDCl₃) δ: 1.33 (6H, d, J=6.3 Hz), 1.52-1.65 (1H, m), 1.68-1.82 (1H, m), 1.83-1.92 (1H, m), 1.95-2.04 (1H, m), 2.33-2.42 (1H, m), 2.73 (1H, t, J=11.3 Hz), 2.98-3.09 (1H, m), 3.70 (3H, s), 3.81-3.89 (1H, m), 3.92-4.00 (1H, m), 4.47-4.55 (1H, m), 6.86 (2H, d, J=8.8 Hz), 7.53 (2H, d, J=8.8 Hz), 7.61 (1H, t, J=7.8 Hz), 7.84 (1H, d, J=7.8 Hz), 8.12 (1H, d, J=7.8 Hz), 8.16-8.21 (2H, m), 8.73 (1H, s)

Example 12

3-(Octahydropyrrolo[1,2-a]pyrazin-2(1H)-ylsulfonyl)-N-(4-isopropoxyphenyl)benzamide trifluoroacetate The entitled compound was produced according to the method of Example 1 but using the compound obtained in Reference Example 1 and octahydropyrrolo[1,2-a]pyrazine as the starting materials.

¹H-NMR (CDCl₃) δ: 1.33 (6H, d, J=6.3 Hz), 1.83-2.31 (4H, m), 2.51-4.24 (9H, m), 4.47-4.57 (1H, m), 6.88 (2H, d, J=8.8 Hz), 7.58 (2H, d, J=8.8 Hz), 7.65 (1H, t, J=7.8 Hz), 7.89 (1H, d, J=7.8 Hz), 8.02-8.13 (2H, m), 9.27 (1H, s)

Example 13

N-(4-Isopropoxyphenyl)-3-(octahydro-2H-pyrido[1,2-a]pyrazin-2-ylsulfonyl)benzamide trifluoroacetate The entitled compound was produced according to the method of Example 1 but using the compound obtained in Reference Example 1 and octahydro-2H-pyrido[1,2-a]pyrazine as the starting materials.

¹H-NMR (CDCl₃) δ: 1.33 (6H, d, J=5.9 Hz), 1.42-2.05 (6H, m), 2.62-2.73 (1H, m), 2.92-3.06 (2H, m), 3.13-3.27 (2H, m), 3.39-3.49 (2H, m), 3.76-3.86 (2H, m), 4.47-4.55 (1H, m), 6.87 (2H, d, J=8.8 Hz), 7.58-7.65 (3H, m), 7.88 (1H, d, J=7.8 Hz), 8.03-8.08 (2H, m), 9.35 (1H, s)

Example 14

N-(4-Isopropoxyphenyl)-3-{[3-(morpholin-4-ylmethyl)piperidin-1-yl]sulfonyl}benzamide trifluoroacetate The entitled compound was produced according to the method of Example 1 but using the compound obtained in Reference Example 1 and 4-(piperidin-3-ylmethyl)morpholine as the starting materials.

¹H-NMR (CDCl₃) δ: 1.12-1.80 (8H, m), 1.33 (6H, d, J=6.3 Hz), 2.17-2.30 (1H, m), 2.60-2.82 (3H, m), 3.06-3.14 (1H, m), 3.47-3.56 (1H, m), 3.66-3.76 (1H, m), 3.92-4.04 (4H, m), 4.47-4.56 (1H, m), 6.88 (2H, d, J=9.0 Hz), 7.58-7.68 (3H, m), 7.87 (1H, d, J=7.8 Hz), 8.25 (1H, d, J=7.8 Hz), 8.37 (1H, s), 9.23 (1H, s)

Example 15

3-[(4-Fluoropiperidin-1-yl)sulfonyl]-N-(4-isopropoxyphenyl)benzamide

The entitled compound was produced according to the method of Example 1 but using the compound obtained in Reference Example 1 and 4-fluoropiperidine as the starting materials.

¹H-NMR (CDCl₃) δ: 1.34 (6H, d, J=6.3 Hz), 1.81-2.03 (4H, m), 2.84-2.98 (2H, m), 3.34-3.44 (2H, m), 4.49-4.58 (1H, m), 4.66-4.85 (1H, m), 6.91 (2H, d, J=9.0 Hz), 7.54 (2H, d, J=9.0 Hz), 7.68 (1H, t, J=7.8 Hz), 7.85-7.95 (2H, m), 8.13 (1H, d, J=7.8 Hz), 8.20 (1H, s)

Example 16

3-(2-Azabicyclo[2.2.2]oct-2-ylsulfonyl)-N-(4-isopropoxyphenyl)benzamide

The entitled compound was produced according to the method of Example 1 but using the compound obtained in Reference Example 1 and 2-azabicyclo[2.2.2]octane as the starting materials.

¹H-NMR (CDCl₃) δ: 1.34 (6H, d, J=6.3 Hz), 1.44-1.91 (9H, m), 3.32 (2H, s), 3.87 (1H, s), 4.49-4.58 (1H, m), 6.91 (2H, d, J=9.0 Hz), 7.55 (2H, d, J=9.0 Hz), 7.64 (1H, t, J=7.8 Hz), 7.94-8.02 (2H, m), 8.12 (1H, d, J=7.8 Hz), 8.27 (1H, s)

Example 17

3-[(4,4-Difluoropiperidin-1-yl)sulfonyl]-N-(4-isopropoxyphenyl)benzamide

The entitled compound was produced according to the method of Example 1 but using the compound obtained in Reference Example 1 and 4,4-difluoropiperidine as the starting materials.

¹H-NMR (CDCl₃) δ: 1.34 (6H, d, J=6.3 Hz), 2.00-2.14 (4H, m), 3.17-3.28 (4H, m), 4.48-4.59 (1H, m), 6.91 (2H, d, J=9.0 Hz), 7.53 (2H, d, J=9.0 Hz), 7.68 (1H, t, J=7.8 Hz), 7.85-7.96 (2H, m), 8.13 (1H, d, J=7.8 Hz), 8.22 (1H, s)

Example 18

N-(4-isopropoxyphenyl)-3-[(3-methoxypiperidin-1-yl)sulfonyl]benzamide

The entitled compound was produced according to the method of Example 1 but using the compound obtained in Reference Example 1 and 3-methoxypiperidine as the starting materials.

¹H-NMR (CDCl₃) δ: 1.22-1.38 (1H, m), 1.34 (6H, d, J=5.9 Hz), 1.45-1.65 (1H, m), 1.74-1.92 (2H, m), 2.52-2.71 (2H, m), 3.28-3.41 (2H, m), 3.36 (3H, s), 3.51-3.61 (1H, m), 4.47-4.60 (1H, m), 6.91 (2H, d, J=9.0 Hz), 7.54 (2H, d, J=9.0 Hz), 7.66 (1H, t, J=7.8 Hz), 7.88-7.99 (2H, m), 8.11-8.17 (1H, m), 8.21 (1H, s)

Example 19

3-[(3,3-Difluoropiperidin-1-yl)sulfonyl]-N-(4-isopropoxyphenyl)benzamide

The entitled compound was produced according to the method of Example 1 but using the compound obtained in Reference Example 1 and 3,3-difluoropiperidine as the starting materials.

¹H-NMR (CDCl₃) δ: 1.34 (6H, d, J=6.3 Hz), 1.73-1.82 (2H, m), 1.83-1.97 (2H, m), 3.11-3.19 (2H, m), 3.31-3.41 (2H, m), 4.48-4.58 (1H, m), 6.90 (2H, d, J=9.0 Hz), 7.53 (2H, d, J=9.0 Hz), 7.67 (1H, t, J=7.8 Hz), 7.90-7.98 (2H, m), 8.14 (1H, d, J=7.8 Hz), 8.21 (1H, s)

Example 20

N-(4-isopropoxyphenyl)-3-{[3-(pyridin-3-ylmethoxy)piperidin-1-yl]sulfonyl}benzamide trifluoroacetate The entitled compound was produced according to the method of Example 1 but using the compound obtained in Reference Example 1 and 3-[(piperidin-3-yloxy)methyl]pyridine as the starting materials.

¹H-NMR (CDCl₃) δ: 1.33 (6H, d, J=5.9 Hz), 1.46-1.64 (2H, m), 1.77-1.93 (2H, m), 2.86-3.00 (2H, m), 3.16-3.25 (1H, m), 3.35-3.43 (1H, m), 3.57-3.66 (1H, m), 4.47-4.57 (1H, m), 4.62 (1H, d, J=12.9 Hz), 4.70 (1H, d, J=12.9 Hz), 6.87 (2H, d, J=8.6 Hz), 7.55 (2H, d, J=8.6 Hz), 7.60-7.67 (2H, m), 7.84-7.91 (1H, m), 8.07-8.15 (2H, m), 8.24 (1H, s), 8.52 (1H, s), 8.57-8.62 (1H, m), 8.66 (1H, s)

Example 21

N-(4-isopropoxyphenyl)-3-{[3-(pyridin-2-yl-methoxy)piperidin-1-yl]sulfonyl}benzamide trifluoroacetate The entitled compound was produced according to the method of Example 1 but using the compound obtained in Reference Example 1 and 2-[(piperidin-3-yloxy)methyl]pyridine as the starting materials.

$^1$H-NMR (CDCl$_3$) δ: 1.33 (6H, d, J=5.9 Hz), 1.49-1.63 (2H, m), 1.78-1.93 (2H, m), 2.88-3.01 (2H, m), 3.13-3.22 (1H, m), 3.33-3.41 (1H, m), 3.62-3.70 (1H, m), 4.47-4.56 (1H, m), 4.85 (2H, s), 6.88 (2H, d, J=9.0 Hz), 7.49-7.66 (4H, m), 7.74-7.78 (1H, m), 7.86-7.91 (1H, m), 8.06-8.12 (1H, m), 8.12-8.18 (1H, m), 8.26 (1H, s), 8.57 (1H, s), 8.64-8.69 (1H, m)

Example 22

N-(4-isopropoxyphenyl)-3-[(3-oxo-2,3,6,7-tetrahydroisoxazolo[4,5-c]pyridin-5(4H)-yl)sulfonyl]benzamide The entitled compound was produced according to the method of Example 1 but using the compound obtained in Reference Example 1 and 4,5,6,7-tetrahydroisoxazolo[4,5-c]pyridin-3(2H)-one as the starting materials.

$^1$H-NMR (DMSO-d$_6$) δ: 1.25 (6H, d, J=6.3 Hz), 2.64-2.74 (2H, m), 3.42-3.50 (2H, m), 3.98 (2H, s), 4.52-4.62 (1H, m), 6.91 (2H, d, J=8.8 Hz), 7.63 (2H, d, J=8.8 Hz), 7.78 (1H, t, J=7.8 Hz), 8.01 (1H, d, J=7.8 Hz), 8.26 (1H, d, J=7.8 Hz), 8.34 (1H, s), 10.38 (1H, s), 11.46 (1H, s)

Example 23

N-(4-isopropoxyphenyl)-3-{[(2S)-2-methylpyrrolidin-1-yl]sulfonyl}benzamide

The entitled compound was produced according to the method of Example 1 but using the compound obtained in Reference Example 1 and (2S)-2-methylpyrrolidine as the starting materials.

$^1$H-NMR (CDCl$_3$) δ: 1.30 (3H, d, J=6.3 Hz), 1.34 (6H, d, J=6.3 Hz), 1.46-1.62 (2H, m), 1.65-1.77 (1H, m), 1.79-1.92 (1H, m), 3.10-3.21 (1H, m), 3.40-3.51 (1H, m), 3.69-3.81 (1H, m), 4.47-4.58 (1H, m), 6.90 (2H, d, J=8.6 Hz), 7.55 (2H, d, J=8.6 Hz), 7.64 (1H, t, J=7.8 Hz), 7.94-8.04 (2H, m), 8.12 (1H, d, J=7.8 Hz), 8.26 (1H, s)

Example 24

N-(4-isopropoxyphenyl)-3-{[(2R)-2-methylpyrrolidin-1-yl]sulfonyl}benzamide

The entitled compound was produced according to the method of Example 1 but using the compound obtained in Reference Example 1 and (2R)-2-methylpyrrolidine as the starting materials.

$^1$H-NMR (CDCl$_3$) δ: 1.30 (3H, d, J=6.3 Hz), 1.34 (6H, d, J=6.3 Hz), 1.46-1.62 (2H, m), 1.65-1.77 (1H, m), 1.79-1.92 (1H, m), 3.10-3.21 (1H, m), 3.40-3.51 (1H, m), 3.69-3.81 (1H, m), 4.47-4.58 (1H, m), 6.90 (2H, d, J=8.6 Hz), 7.55 (2H, d, J=8.6 Hz), 7.64 (1H, t, J=7.8 Hz), 7.94-8.04 (2H, m), 8.12 (1H, d, J=7.8 Hz), 8.26 (1H, s)

Example 25

3-({[2-(1H-benzimidazol-2-yl)propyl]amino}sulfonyl)-N-(4-isopropoxyphenyl)benzamide The entitled compound was produced according to the method of Example 1 but using the compound obtained in Reference Example 1 and 2-(1H-benzimidazol-2-yl)propan-1-amine as the starting materials.

$^1$H-NMR (CDCl$_3$) δ: 1.25-1.33 (9H, m), 3.16-3.37 (3H, m), 4.43-4.55 (1H, m), 6.23 (1H, s), 6.80-6.88 (2H, m), 7.10-7.21 (2H, m), 7.35-7.46 (3H, m), 7.52 (2H, d, J=7.8 Hz), 7.75-7.85 (1H, m), 7.99 (1H, d, J=7.8 Hz), 8.26 (1H, s), 8.64-8.84 (1H, m)

Example 26

3-{[(2R,5R)-2,5-dimethylpyrrolidin-1-yl]sulfonyl}-N-(4-isopropylphenyl)benzamide Triethylamine (0.050 mL) and the compound (50 mg) obtained in Reference Example 2 were added in that order to a chloroform (1.0 mL) solution of (2R,5R)-2,5-dimethylpyrrolidine (50 mg), and stirred at room temperature for 1 hour. The reaction liquid was concentrated, and purified through reversed-phase HPLC (0.1% TFA acetonitrile/H$_2$O)=from 10% to 95%, gradient) to give the entitled compound (59 mg, 100%) as a white crystal.

$^1$H-NMR (CDCl$_3$) δ: 1.17 (6H, d, J=6.3 Hz), 1.22 (6H, d, J=7.0 Hz), 1.45-1.60 (2H, m), 2.02-2.16 (2H, m), 2.82-2.95 (1H, m), 3.98-4.09 (2H, m), 7.18-7.26 (2H, m), 7.54 (2H, d, J=8.2 Hz), 7.55-7.65 (1H, m), 7.91 (1H, s), 7.94-8.01 (1H, m), 8.03 (1H, d, J=7.4 Hz), 8.25 (1H, s)

Example 27

3-(Azepan-1-ylsulfonyl)-N-(4-isopropylphenyl)benzamide

The entitled compound was produced according to the method of Example 26 but using the compound obtained in Reference Example 2 and hexamethyleneamine as the starting materials.

$^1$H-NMR (CDCl$_3$) δ: 1.26 (6H, d, J=6.8 Hz), 1.54-1.78 (8H, m), 2.86-2.98 (1H, m), 3.30 (4H, t, J=5.9 Hz), 7.25 (2H, d, J=7.8 Hz), 7.57 (2H, d, J=8.3 Hz), 7.64 (1H, t, J=7.8 Hz), 7.92 (1H, s), 7.95 (1H, d, J=7.8 Hz), 8.10 (1H, d, J=7.3 Hz), 8.22 (1H, s)

Example 28

N-(4-isopropylphenyl)-3-(pyrrolidin-1-ylsulfonyl)benzamide

The entitled compound was produced according to the method of Example 26 but using the compound obtained in Reference Example 2 and pyrrolidine as the starting materials.

$^1$H-NMR (CDCl$_3$) δ: 1.22 (6H, d, J=7.0 Hz), 1.74 (4H, t, J=6.6 Hz), 2.82-2.96 (1H, m), 3.22 (4H, t, J=6.6 Hz), 7.21 (2H, d, J=8.6 Hz), 7.55 (2H, d, J=8.6 Hz), 7.63 (1H, t, J=7.8 Hz), 7.94 (1H, d, J=7.8 Hz), 8.07 (1H, s), 8.11 (1H, d, J=7.8 Hz), 8.23 (1H, s)

Example 29

N-(4-isopropylphenyl)-3-(morpholin-4-ylsulfonyl)benzamide

The entitled compound was produced according to the method of Example 26 but using the compound obtained in Reference Example 2 and morpholine as the starting materials.

$^1$H-NMR (CDCl$_3$) δ: 1.22 (6H, d, J=7.0 Hz), 2.81-2.94 (1H, m), 2.99 (4H, t, J=4.7 Hz), 3.70 (4H, t, J=4.7 Hz), 7.22 (2H, d, J=8.2 Hz), 7.53 (2H, d, J=8.2 Hz), 7.66 (1H, t, J=7.8 Hz), 7.87 (1H, d, J=7.8 Hz), 7.93 (1H, s), 8.12 (1H, d, J=7.8 Hz), 8.17 (1H, s)

Example 30

N-(4-isopropylphenyl)-3-[(2-methylpiperidin-1-yl)sulfonyl]benzamide

The entitled compound was produced according to the method of Example 26 but using the compound obtained in Reference Example 2 and 2-methylpiperidine as the starting materials.

$^1$H-NMR (CDCl$_3$) δ: 1.08 (3H, d, J=7.0 Hz), 1.26 (6H, d, J=7.0 Hz), 1.29-1.60 (6H, m), 2.85-2.96 (1H, m), 3.01 (1H, td, J=13.0, 2.6 Hz), 3.69-3.78 (1H, m), 4.21-4.31 (1H, m), 7.23-7.28 (2H, m), 7.58 (2H, d, J=8.6 Hz), 7.63 (1H, t, J=7.8 Hz), 7.93-8.01 (2H, m), 8.09 (1H, d, J=7.8 Hz), 8.26 (1H, s)

Example 31

3-{[(2R,6S)-2,6-dimethylpiperidin-1-yl]sulfonyl}-N-(4-isopropylphenyl)benzamide

The entitled compound was produced according to the method of Example 26 but using the compound obtained in Reference Example 2 and (2R,6S)-2,6-dimethylpiperidine as the starting materials.

$^1$H-NMR (CDCl$_3$) δ: 1.17-1.78 (6H, m), 1.22 (6H, d, J=6.6 Hz), 1.33 (6H, d, J=7.0 Hz), 2.81-2.95 (1H, m), 4.11-4.22 (2H, m), 7.19-7.26 (2H, m), 7.53 (2H, d, J=8.6 Hz), 7.59 (1H, t, J=7.8 Hz), 7.84 (1H, s), 7.92-7.97 (1H, m), 8.05 (1H, d, J=7.8 Hz), 8.23 (1H, s)

Example 32

3-[(3-Hydroxypiperidin-1-yl)sulfonyl]-N-(4-isopropylphenyl)benzamide

The entitled compound was produced according to the method of Example 26 but using the compound obtained in Reference Example 2 and 3-hydroxypiperidine as the starting materials.

$^1$H-NMR (CDCl$_3$) δ: 1.22 (6H, d, J=7.0 Hz), 1.32-1.45 (1H, m), 1.48-1.63 (1H, m), 1.65-1.88 (2H, m), 2.72-2.96 (3H, m), 3.06-3.16 (1H, m), 3.30 (1H, dd, J=11.3, 2.7 Hz), 3.78-3.88 (1H, m), 7.20 (2H, d, J=8.2 Hz), 7.53 (2H, d, J=8.6 Hz), 7.63 (1H, t, J=7.8 Hz), 7.87 (1H, d, J=7.8 Hz), 8.05 (1H, s), 8.11 (1H, d, J=7.8 Hz), 8.18 (1H, s)

Example 33

(3R)-3-fluoropyrrolidin-1-yl]sulfonyl]-N-(4-isopropylphenyl)benzamide

The entitled compound was produced according to the method of Example 26 but using the compound obtained in Reference Example 2 and (3R)-3-fluoropyrrolidine as the starting materials.

$^1$H-NMR (CDCl$_3$) δ: 1.22 (6H, d, J=6.6 Hz), 1.82-2.04 (1H, m), 2.06-2.22 (1H, m), 2.81-2.94 (1H, m), 3.22-3.33 (1H, m), 3.40-3.66 (3H, m), 5.13 (1H, dt, J=52.5, 3.4 Hz), 7.18-7.24 (2H, m), 7.53 (2H, d, J=8.2 Hz), 7.64 (1H, t, J=7.8 Hz), 7.92-7.99 (2H, m), 8.11 (1H, d, J=7.8 Hz), 8.23 (1H, s)

Example 34

1-[(3-{[(4-Isopropylphenyl)amino]carbonyl]phenyl)sulfonyl}piperidine-3-carboxamide The entitled compound was produced according to the method of Example 26 but using the compound obtained in Reference Example 2 and (3R)-3-fluoropyrrolidine as the starting materials.

$^1$H-NMR (DMSO-d$_6$) δ: 1.19-1.30 (1H, m), 1.19 (6H, d, J=6.6 Hz), 1.39-1.53 (1H, m), 1.66-1.82 (2H, m), 2.14-2.29 (2H, m), 2.30-2.43 (1H, m), 2.81-2.92 (1H, m), 3.56-3.71 (2H, m), 6.92 (1H, s), 7.23 (2H, d, J=8.6 Hz), 7.41 (1H, s), 7.66 (2H, d, J=8.6 Hz), 7.81 (1H, t, J=7.8 Hz), 7.93 (1H, d, J=7.8 Hz), 8.22-8.32 (2H, m), 10.45 (1H, s)

Example 35

1-[(3-{[(4-Isopropylphenyl)amino]carbonyl]phenyl)sulfonyl}piperidine-4-carboxamide The entitled compound was produced according to the method of Example 26 but using the compound obtained in Reference Example 2 and piperidine-3-carboxamide as the starting materials.

$^1$H-NMR (DMSO-d$_6$) δ: 1.19 (6H, d, J=6.6 Hz), 1.45-1.60 (2H, m), 1.69-1.83 (2H, m), 1.99-2.11 (1H, m), 2.27-2.39 (2H, m), 2.81-2.92 (1H, m), 3.54-3.66 (2H, m), 6.79 (1H, s), 7.19 (1H, s), 7.23 (2H, d, J=8.6 Hz), 7.66 (2H, d, J=8.6 Hz), 7.80 (1H, t, J=7.8 Hz), 7.93 (1H, d, J=7.8 Hz), 8.23-8.30 (2H, m), 10.45 (1H, s)

Example 36

3-{[(3R)-3-hydroxypiperidin-1-yl]sulfonyl}-N-(4-isopropylphenyl)benzamide

The entitled compound was produced according to the method of Example 26 but using the compound obtained in Reference Example 2 and (R)-3-hydroxypiperidine hydrochloride as the starting materials.

$^1$H-NMR (CDCl$_3$) δ: 1.22 (6H, d, J=7.0 Hz), 1.31-1.46 (1H, m), 1.48-1.89 (3H, m), 2.70-2.93 (3H, m), 3.06-3.16 (1H, m), 3.30 (1H, dd, J=11.7, 3.1 Hz), 3.77-3.87 (1H, m), 7.18-7.23 (2H, m), 7.53 (2H, d, J=8.2 Hz), 7.63 (1H, t, J=7.8 Hz), 7.87 (1H, d, J=7.8 Hz), 8.02 (1H, s), 8.10 (1H, d, J=7.8 Hz), 8.18 (1H, s)

Example 37

3-{[3-(hydroxymethyl)piperidin-1-yl]sulfonyl}-N-(4-isopropylphenyl)benzamide

The entitled compound was produced according to the method of Example 26 but using the compound obtained in Reference Example 2 and piperidin-3-ylmethanol as the starting materials.

$^1$H-NMR (CDCl$_3$) δ: 0.94-1.10 (1H, m), 1.22 (6H, d, J=7.0 Hz), 1.48-1.87 (4H, m), 2.27-2.38 (1H, m), 2.40-2.54 (1H, m), 2.82-2.94 (1H, m), 3.43 (1H, dd, J=10.9, 7.8 Hz), 3.48-

3.59 (2H, m), 3.62-3.72 (1H, m), 7.21 (2H, d, J=8.6 Hz), 7.54 (2H, d, J=8.6 Hz), 7.63 (1H, t, J=7.8 Hz), 7.88 (1H, d, J=7.8 Hz), 8.06-8.21 (3H, m)

Example 38

3-[(Cyclohexylamino)sulfonyl]-N-(4-isopropylphenyl)benzamide

The entitled compound was produced according to the method of Example 26 but using the compound obtained in Reference Example 2 and cyclohexneamine as the starting materials.

$^1$H-NMR (CDCl$_3$) δ: 1.00-1.25 (4H, m), 1.22 (6H, d, J=6.6 Hz), 1.41-1.54 (2H, m), 1.54-1.65 (2H, m), 1.65-1.77 (2H, m), 2.81-2.94 (1H, m), 3.05-3.21 (1H, m), 4.71 (1H, d, J=7.8 Hz), 7.17-7.25 (2H, m), 7.53 (2H, d, J=8.2 Hz), 7.60 (1H, t, J=7.8 Hz), 7.95-8.05 (2H, m), 8.08 (1H, d, J=8.2 Hz), 8.32 (1H, s)

Example 39

3-(Anilinosulfonyl)-N-(4-isopropylphenyl)benzamide

The entitled compound was produced according to the method of Example 26 but using the compound obtained in Reference Example 2 and aniline as the starting materials.

$^1$H-NMR (CDCl$_3$) δ: 1.21 (6H, d, J=6.6 Hz), 2.80-2.92 (1H, m), 7.04-7.15 (4H, m), 7.15-7.27 (4H, m), 7.44-7.52 (3H, m), 7.80 (1H, d, J=7.8 Hz), 7.89 (1H, s), 8.03 (1H, d, J=7.8 Hz), 8.25 (1H, s)

Example 40

N-(4-Isopropylphenyl)-3-{[(2R)-2-(methoxymethyl)pyrrolidin-1-yl]sulfonyl}benzamide The entitled compound was produced according to the method of Example 26 but using the compound obtained in Reference Example 2 and (2R)-2-(methoxymethyl)pyrrolidine as the starting materials.

$^1$H-NMR (CDCl$_3$) δ: 1.22 (6H, d, J=7.0 Hz), 1.50-1.65 (2H, m), 1.75-1.90 (2H, m), 2.76-2.97 (2H, m), 3.07-3.18 (1H, m), 3.31-3.36 (1H, m), 3.32 (1H, s), 3.37-3.45 (1H, m), 3.56 (1H, dd, J=9.6, 3.7 Hz), 3.70-3.80 (1H, m), 7.18-7.25 (2H, m), 7.54 (2H, d, J=8.2 Hz), 7.62 (1H, t, J=7.8 Hz), 7.96 (1H, d, J=7.8 Hz), 8.03 (1H, s), 8.11 (1H, d, J=7.8 Hz), 8.25 (1H, s)

Example 41

3-{[(3R)-3-hydroxypiperidin-1-yl]sulfonyl}-N-(2-methoxyphenyl)benzamide

The entitled compound was produced according to the method of Example 1 but using the compound obtained in Reference Example 3 and (R)-3-hydroxypiperidine hydrochloride as the starting materials.

$^1$H-NMR (CDCl$_3$) δ: 1.39-1.49 (1H, m), 1.57-1.70 (1H, m), 1.72-1.82 (1H, m), 1.82-1.94 (1H, m), 2.80 (1H, dd, J=11.2, 7.3 Hz), 2.84-2.93 (1H, m), 3.10-3.23 (2H, m), 3.38 (1H, dd, J=11.2, 3.4 Hz), 3.85-3.93 (1H, m), 3.94 (3H, s), 6.95 (1H, dd, J=8.0, 1.2 Hz), 7.04 (1H, td, J=7.8, 1.0 Hz), 7.13 (1H, td, J=7.8, 1.5 Hz), 7.69 (1H, t, J=7.8 Hz), 7.95 (1H, dt, J=8.1, 1.3 Hz), 8.12 (1H, dt, J=7.8, 1.5 Hz), 8.25 (1H, t, J=1.7 Hz), 8.43-8.50 (1H, m), 8.54 (1H, s)

Example 42

3-{[3-(hydroxymethyl)piperidin-1-yl]sulfonyl}-N-(2-methoxyphenyl)benzamide

The entitled compound was produced according to the method of Example 1 but using the compound obtained in Reference Example 3 and piperidin-3-ylmethanol as the starting materials.

$^1$H-NMR (CDCl$_3$) δ: 0.98-1.13 (1H, m), 1.54-1.97 (4H, m), 2.30-2.39 (1H, m), 2.51 (1H, td, J=10.9, 2.9 Hz), 2.66 (1H, s), 3.46-3.75 (4H, m), 3.94 (3H, s), 6.95 (1H, dd, J=8.0, 1.2 Hz), 7.04 (1H, td, J=7.8, 1.5 Hz), 7.13 (1H, td, J=7.8, 2.0 Hz), 7.69 (1H, t, J=7.8 Hz), 7.94 (1H, dt, J=8.0, 1.5 Hz), 8.10 (1H, dt, J=7.6, 1.5 Hz), 8.24 (1H, t, J=1.5 Hz), 8.42-8.50 (1H, m), 8.55 (1H, s)

Example 43

1-[(3-{[(2-methoxyphenyl)amino]carbonyl]phenyl)sulfonyl}piperidine-3-carboxamide The entitled compound was produced according to the method of Example 1 but using the compound obtained in Reference Example 3 and piperidine-3-carboxamide as the starting materials.

$^1$H-NMR (DMSO-d$_6$) δ: 1.18-1.32 (1H, m), 1.39-1.55 (1H, m), 1.66-1.81 (2H, m), 2.15-2.31 (2H, m), 2.31-2.44 (1H, m), 3.57-3.72 (2H, m), 3.83 (3H, d, J=12.2 Hz), 6.90-7.01 (2H, m), 7.08-7.13 (1H, m), 7.18-7.25 (1H, m), 7.42 (1H, s), 7.65 (1H, d, J=6.8 Hz), 7.80 (1H, t, J=7.6 Hz), 7.91-7.96 (1H, m), 8.21-8.33 (2H, m), 9.88 (1H, s)

Example 44

5-{[(3-{[(4-methoxyphenyl)amino]carbonyl}phenyl)sulfonyl]amino}pentanoic acid (Step 1) Production of 3-{[(5-hydroxypentyl)amino]sulfonyl}-N-(4-methoxyphenyl)benzamide The intended compound was produced according to the method of Example 1 but using the compound obtained in Reference Example 4 and 5-aminopentan-1-ol as the starting materials.

(Step 2) Production of 5-{[(3-{[(4-methoxyphenyl)amino]carbonyl}phenyl)sulfonyl]amino}pentanoic acid With stirring, Jones reagent (mixed solution of chromic acid (280 mg), sulfuric acid (0.25 mL) and water (0.50 mL)) were dropwise added at room temperature to an acetone (10 mL) solution of the compound (500 mg) obtained in the step 1. After stirred overnight at room temperature, an excessive amount of methanol was added to it. After this was stirred at room temperature for 10 minutes, the solvent was evaporated off under reduced pressure. The residue was diluted with ethyl acetate, washed with water and saturated brine, and the organic layer was dried with anhydrous magnesium sulfate. The drying agent was removed through filtration, and the solvent was evaporated off under reduced pressure. The resulting residue was purified through silica gel column chromatography (chloroform/methanol=9/1) to give the entitled compound (58 mg, 11%) as a pale violet solid.

$^1$H-NMR (DMSO-d$_6$) δ: 1.35-1.50 (4H, m), 2.15 (2H, t, J=7.1 Hz), 2.75 (2H, q, J=6.3 Hz), 3.75 (3H, s), 6.95 (2H, d,

J=9.3 Hz), 7.67 (2H, d, J=8.8 Hz), 7.72-7.75 (1H, br m), 7.75 (1H, t, J=7.8 Hz), 7.97 (1H, d, J=8.8 Hz), 8.19 (1H, d, J=7.8 Hz), 8.33 (1H, s), 10.41 (1H, s)

Example 45

3-[(Tert-butylamino)sulfonyl]-N-(4-methoxyphenyl)benzamide

The entitled compound was produced according to the method of Example 1 but using the compound obtained in Reference Example 4 and 2-methylpropane-2-amine as the starting materials.

$^1$H-NMR (DMSO-$d_6$) δ: 1.11 (9H, s), 3.75 (3H, s), 6.95 (2H, d, J=9.3 Hz), 7.66-7.69 (3H, m), 7.73 (1H, t, J=7.8 Hz), 8.02 (1H, d, J=7.8 Hz), 8.16 (1H, d, J=7.8 Hz), 8.37 (1H, s), 10.37 (1H, s)

Example 46

N-(4-methoxyphenyl)-3-(piperidin-1-ylsulfonyl)benzamide

The entitled compound was produced according to the method of Example 1 but using the compound obtained in Reference Example 4 and piperidine as the starting materials.

$^1$H-NMR (CDCl$_3$) δ: 1.38-1.47 (2H, m), 1.57-1.69 (4H, m), 2.95-3.06 (4H, m), 3.83 (3H, s), 6.92 (2H, d, J=8.8 Hz), 7.57 (2H, d, J=8.8 Hz), 7.66 (1H, t, J=7.8 Hz), 7.90 (1H, d, J=7.8 Hz), 7.95 (1H, s), 8.14 (1H, d, J=7.8 Hz), 8.18 (1H, s).

Example 47

N-(3-methoxypyridin-2-yl)-3-(morpholin-4-ylsulfonyl)benzamide

Triethylamine (0.13 mL) and morpholine (41.2 mg) were added in that order to a THF (2.0 mL) solution of the compound (50.0 mg) obtained in Reference Example 5, and stirred overnight at room temperature. The reaction liquid was evaporated under reduced pressure, and the residue was purified through reversed-phase HPLC (0.1% TFA acetonitrile/H$_2$O=from 10% to 90%, gradient) to give the entitled compound (32 mg, 90%) as a white solid.

$^1$H-NMR (CDCl$_3$) δ: 3.03 (4H, t, J=4.6 Hz), 3.75 (4H, t, J=4.6 Hz), 3.94 (3H, s), 7.13 (1H, dd, J=8.3, 4.9 Hz), 7.23-7.28 (1H, m), 7.71 (1H, t, J=7.8 Hz), 7.93 (1H, d, J=7.8 Hz), 8.11 (1H, d, J=4.9 Hz), 8.19 (1H, d, J=7.8 Hz), 8.26 (1H, s)

Example 48

N-(3-methoxypyridin-2-yl)-3-{[(2S)-2-methylpyrrolidin-1-yl]sulfonyl}benzamide The entitled compound was produced according to the method of Example 47 but using the compound obtained in Reference Example 5 and (2S)-2-methylpyrrolidine as the starting materials.

$^1$H-NMR (CDCl$_3$) δ: 1.33 (3H, d, J=6.5 Hz), 1.47-1.63 (2H, m), 1.68-1.78 (1H, m), 1.82-1.93 (1H, m), 3.14-3.22 (1H, m), 3.44-3.52 (1H, m), 3.71-3.80 (1H, m), 3.94 (3H, s), 7.14 (1H, dd, J=8.2, 4.9 Hz), 7.23-7.28 (1H, m), 7.68 (1H, t, J=7.7 Hz), 8.01-8.05 (1H, m), 8.10-8.14 (1H, m), 8.15-8.20 (1H, m), 8.30-8.33 (1H, m)

Example 49

3-(2-Azabicyclo[2.2.1]hept-2-ylsulfonyl)-N-(3-methoxypyridin-2-yl)benzamide The entitled compound was produced according to the method of Example 47 but using the compound obtained in Reference Example 5 and 2-azabicyclo[2.2.1]heptane as the starting materials.

$^1$H-NMR (CDCl$_3$) δ: 0.77-1.85 (6H, m), 2.47 (1H, s), 3.01-3.12 (2H, m), 3.91 (3H, s), 4.20 (1H, s), 7.09-7.14 (1H, m), 7.21-7.27 (1H, m), 7.64 (1H, t, J=7.8 Hz), 7.99 (1H, d, J=7.8 Hz), 8.09 (1H, d, J=4.7 Hz), 8.15 (1H, d, J=7.8 Hz), 8.27 (1H, s)

Example 50

3-{[3-(1H-benzimidazol-2-yl)piperidin-1-yl]sulfonyl}-N-(3-methoxypyridin-2-yl)benzamide The entitled compound was produced according to the method of Example 47 but using the compound obtained in Reference Example 5 and 2-piperidin-3-yl-1H-benzimidazole as the starting materials.

$^1$H-NMR (CDCl$_3$) δ: 1.63-1.84 (2H, m), 1.92-2.10 (2H, m), 2.80-2.91 (1H, m), 3.11-3.20 (1H, m), 3.25-3.34 (1H, m), 3.41-3.51 (1H, m), 3.69-3.78 (1H, m), 3.88 (3H, s), 7.11 (1H, dd, J=7.8, 4.9 Hz), 7.19-7.28 (3H, m), 7.54-7.60 (2H, m), 7.65 (1H, t, J=7.8 Hz), 7.89-7.93 (1H, m), 8.03-8.07 (1H, m), 8.12-8.17 (1H, m), 8.26-8.29 (1H, m)

Example 51

3-(2-Azabicyclo[2.2.2]oct-2-ylsulfonyl)-N-(3-methoxypyridin-2-yl)benzamide

The entitled compound was produced according to the method of Example 47 but using the compound obtained in Reference Example 5 and 2-azabicyclo[2.2.2]octane as the starting materials.

$^1$H-NMR (CDCl$_3$) δ: 1.47-1.92 (9H, m), 3.31-3.38 (2H, m), 3.88 (1H, s), 3.94 (3H, s), 7.14 (1H, dd, J=8.3, 4.9 Hz), 7.23-7.28 (1H, m), 7.66 (1H, t, J=7.8 Hz), 8.03 (1H, d, J=7.8 Hz), 8.13 (1H, d, J=4.9 Hz), 8.16 (1H, d, J=7.8 Hz), 8.33 (1H, s)

Example 52

3-(7-Azabicyclo[2.2.1]hept-7-ylsulfonyl)-N-(3-methoxypyridin-2-yl)benzamide The entitled compound was produced according to the method of Example 47 but using the compound obtained in Reference Example 5 and 7-azabicyclo[2.2.1]heptane as the starting materials.

$^1$H-NMR (CDCl$_3$) δ: 1.39-1.46 (4H, m), 1.77-1.85 (4H, m), 3.94 (3H, s), 4.20-4.26 (2H, m), 7.14 (1H, dd, J=8.3, 4.9 Hz), 7.23-7.28 (1H, m), 7.64 (1H, t, J=7.8 Hz), 8.08-8.19 (3H, m), 8.40 (1H, t, J=1.7 Hz)

Example 53

N-(3-methoxypyridin-2-yl)-3-[(1R,4R)-2-oxa-5-azabicyclo[2.2.1]hept-5-ylsulfonyl]benzamide The entitled compound was produced according to the method of Example 47 but using the compound obtained in Reference Example 5 and (1R,4R)-2-oxa-5-azabicyclo[2.2.1]heptane monohydrochloride as the starting materials.

$^1$H-NMR (CDCl$_3$) δ: 1.35 (1H, d, J=10.7 Hz), 1.75 (1H, d, J=10.2 Hz), 3.22 (1H, d, J=9.8 Hz), 3.42 (1H, d, J=9.8 Hz), 3.67-3.73 (1H, m), 3.89 (1H, d, J=7.8 Hz), 3.93 (3H, s), 4.52 (2H, d, J=11.7 Hz), 7.13 (1H, dd, J=7.8, 4.9 Hz), 7.24 (1H, d, J=7.8 Hz), 7.68 (1H, t, J=7.8 Hz), 8.03 (1H, d, J=7.8 Hz), 8.11 (1H, d, J=4.9 Hz), 8.17 (1H, d, J=7.8 Hz), 8.34 (1H, s), 8.57 (1H, s)

Example 54

3-(8-Azabicyclo[3.2.1]oct-8-ylsulfonyl)-N-(3-methoxypyridin-2-yl)benzamide

The entitled compound was produced according to the method of Example 47 but using the compound obtained in Reference Example 5 and 8-azabicyclo[3.2.1]octane as the starting materials.

$^1$H-NMR (CDCl$_3$) δ: 1.45-1.68 (8H, m), 1.76-1.89 (2H, m), 3.93 (3H, s), 4.24 (2H, s), 7.11 (1H, dd, J=8.3, 4.9 Hz), 7.23 (1H, dd, J=8.3, 1.5 Hz), 7.63 (1H, t, J=7.8 Hz), 8.03-8.08 (1H, m), 8.10-8.17 (2H, m), 8.35 (1H, s), 8.49 (1H, s)

Example 55

Ethyl 1-[(3-{[(3-methoxypyridin-2-yl)amino]carbonyl}phenyl)sulfonyl]piperidine-3-carboxylate (Step 1) Production of 3-{[3-(ethoxycarbonyl)piperidin-1-yl]sulfonyl}benzoic acid The intended compound (7.12 g, 92%) was produced as a colorless solid according to the method of Reference Example 1 but using 3-(chlorosulfonyl)benzoic acid (5.00 g) and ethyl piperidine-3-carboxylate (7.04 mL) as the starting materials.

(Step 2) Production of ethyl 1-[(3-{[(3-methoxypyridin-2-yl)amino]carbonyl}phenyl)sulfonyl]piperidine-3-carboxylate The intended compound (3.66 g, 70%) was produced as a colorless oil according to the method of Example 92 but using the compound (4.00 g) obtained in the step 1 and 2-amino-3-methoxypyridine (1.45 g) as the starting materials.

$^1$H-NMR (CDCl$_3$) δ: 1.25 (3H, t, J=7.1 Hz), 1.35-1.50 (1H, m), 1.59-1.73 (1H, m), 1.76-1.87 (1H, m), 1.94-2.03 (1H, m), 2.44 (1H, td, J=11.3, 3.3 Hz), 2.56-2.68 (2H, m), 3.55-3.66 (1H, m), 3.78-3.88 (1H, m), 3.93 (3H, s), 4.14 (2H, q, J=7.2 Hz), 7.12 (1H, dd, J=8.3, 4.9 Hz), 7.24 (1H, dd, J=8.3, 1.5 Hz), 7.69 (1H, t, J=7.8 Hz), 7.94 (1H, dt, J=7.8, 1.5 Hz), 8.09-8.13 (1H, m), 8.18 (1H, d, J=7.8 Hz), 8.25 (1H, s), 8.59 (1H, s)

Example 56

1-[(3-{[(3-Methoxypyridin-2-yl)amino]carbonyl}phenyl)sulfonyl]piperidine-3-carboxylic acid The compound (50 mg) obtained in Example 55 was dissolved in methanol (1.0 mL), then aqueous 2 M sodium hydroxide solution (0.056 mL) was added thereto and stirred at room temperature for 17 hours. The reaction liquid was concentrated and then purified through reversed-phase HPLC (0.1% TFA acetonitrile/H$_2$O=from 10% to 95%, gradient) to give the entitled compound (6 mg, 13%) as a colorless oil.

$^1$H-NMR (DMSO-d$_6$) δ: 1.12-1.54 (3H, m), 1.59-1.81 (2H, m), 2.38-2.69 (2H, m), 3.23-3.37 (1H, m), 3.43-3.54 (1H, m), 3.76 (3H, s), 7.31 (1H, dd, J=8.3, 4.9 Hz), 7.50-7.55 (1H, m), 7.76 (1H, t, J=8.0 Hz), 7.88-7.94 (1H, m), 7.99 (1H, dd, J=4.9, 1.5 Hz), 8.20-8.28 (2H, m), 10.61 (1H, s)

Example 57

1-[(3-{[(3-methoxypyridin-2-yl)amino]carbonyl}phenyl)sulfonyl]piperidine-3-carboxamide The compound (50 mg) obtained in Example 56 was dissolved in DMF (1.0 mL), then N,N-diisopropylethylamine (0.030 mL), ammonium chloride (8 mg), 1-hydroxybenzotriazole hydrate (22 mg) and N-(3-dimethylaminopropyl)-N'-ethylcarbodiimide hydrochloride (27 mg) were added thereto in that order, and stirred at room temperature for 3 days. Water was added to the reaction liquid, and extracted four times with ethyl acetate. The organic layers were combined, washed with saturated brine, and dried with sodium sulfate. The drying agent was removed through filtration, and the solvent was evaporated off under reduced pressure. The residue was purified through silica gel column chromatography (methanol/chloroform=from 0% to 20%, gradient) to give the entitled compound (37 mg, 74%) as a colorless solid.

$^1$H-NMR (CDCl$_3$) δ: 1.56-1.73 (2H, m), 1.74-1.89 (2H, m), 2.45-2.57 (1H, m), 2.62-2.73 (1H, m), 2.79-2.91 (1H, m), 3.50 (1H, d, J=11.5 Hz), 3.60-3.69 (1H, m), 3.94 (3H, s), 5.54 (1H, s), 5.97 (1H, s), 7.13 (1H, dd, J=8.0, 4.9 Hz), 7.22-7.27 (1H, m), 7.69 (1H, t, J=7.8 Hz), 7.94 (1H, d, J=8.0 Hz), 8.11 (1H, d, J=4.4 Hz), 8.17 (1H, d, J=8.0 Hz), 8.27 (1H, s), 8.63 (1H, s)

Example 58

1-[(3-{[(5-Isopropoxypyridin-2-yl)amino]carbonyl}phenyl)sulfonyl]piperidine-3-carboxamide The entitled compound was produced according to the method of Example 47 but using the compound obtained in Reference Example 6 and piperidine-3-carboxamide.

$^1$H-NMR (DMSO-d$_6$) δ: 1.18-1.26 (8H, m), 1.28 (6H, d, J=5.9 Hz), 1.38-1.52 (1H, m), 1.68-1.82 (2H, m), 2.15-2.43 (3H, m), 3.57-3.73 (2H, m), 4.63-4.69 (1H, m), 6.92 (1H, s), 7.41 (1H, s), 7.49 (1H, dd, J=9.3, 2.9 Hz), 7.78 (1H, t, J=7.9 Hz), 7.89-7.95 (1H, m), 8.05-8.11 (2H, m), 8.28-8.35 (2H, m), 11.07 (1H, s)

Examples 59, 59'

(3S)-1-[(3-{[(5-isopropoxypyridin-2-yl)amino]carbonyl}phenyl)sulfonyl]piperidine-3-carboxamide, and (3R)-1-[(3-{[(5-isopropoxypyridin-2-yl)amino]carbonyl}phenyl)sulfonyl]piperidine-3-carboxamide The compound (10 mg) obtained in Example 58 was separated through preparative HPLC (Chiralpak AD) (hexane/ethanol=70/30).

The former eluate ((3S)-1-[(3-{[(5-isopropoxypyridin-2-yl)amino]carbonyl}phenyl)sulfonyl]piperidine-3-carboxamide) was obtained as a colorless solid (5.0 mg) (Example 59). The latter eluate ((3R)-1-[(3-{[(5-isopropoxypyridin-2-

Example 60

1-[(3-{[(3-methoxypyridin-2-yl)amino]carbonyl}phenyl)sulfonyl]-N-methylpiperidine-3-carboxamide The entitled compound was produced according to the method of Example 57 but using the compound obtained in Example 56 and methylamine as the starting materials.
$^1$H-NMR (CDCl$_3$) δ: 1.55-1.84 (4H, m), 2.43-2.54 (1H, m), 2.81 (3H, d, J=4.4 Hz), 2.81-2.90 (1H, m), 2.93-3.02 (1H, m), 3.42-3.52 (1H, m), 3.54-3.64 (1H, m), 4.04 (3H, s), 6.28 (1H, s), 7.50 (1H, dd, J=8.0, 5.4 Hz), 7.66-7.75 (2H, m), 7.97-8.05 (2H, m), 8.26 (1H, d, J=8.0 Hz), 8.36 (1H, s)

Example 61

N-benzyl-1-[(3-{[(3-methoxypyridin-2-yl)amino]carbonyl}phenyl)sulfonyl]piperidine-3-carboxamide The entitled compound was produced according to the method of Example 57 but using the compound obtained in Example 56 and benzylamine as the starting materials.
$^1$H-NMR (CDCl$_3$) δ: 1.56-1.90 (4H, m), 2.45-2.56 (1H, m), 2.68-2.80 (1H, m), 2.94 (1H, dd, J=11.7, 9.8 Hz), 3.47-3.60 (1H, m), 3.65-3.77 (1H, m), 4.02 (3H, s), 4.35-4.51 (2H, m), 6.31-6.43 (1H, m), 7.21-7.36 (6H, m), 7.43-7.50 (1H, m), 7.65 (1H, d, J=8.3 Hz), 7.71 (1H, t, J=7.8 Hz), 7.96-8.02 (2H, m), 8.25 (1H, d, J=7.8 Hz), 8.35 (1H, s)

Example 62

Benzyl 1-[(3-{[(3-methoxypyridin-2-yl)amino]carbonyl}phenyl)sulfonyl]piperidine-3-carboxylate The entitled compound was produced according to the method of Example 47 but using the compound obtained in Reference Example 5 and benzyl piperidine-3-carboxylate as the starting materials.
$^1$H-NMR (CDCl$_3$) δ: 1.37-1.53 (1H, m), 1.57-1.73 (1H, m), 1.75-1.89 (1H, m), 1.93-2.06 (1H, m), 2.38-2.54 (1H, m), 2.58-2.77 (2H, m), 3.54-3.68 (1H, m), 3.81-3.90 (1H, m), 3.93 (3H, s), 5.10 (1H, d, J=12.2 Hz), 5.14 (1H, d, J=12.2 Hz), 7.12 (1H, dd, J=8.3, 4.9 Hz), 7.23 (1H, dd, J=8.3, 1.5 Hz), 7.29-7.41 (5H, m), 7.63-7.74 (1H, m), 7.92-7.97 (1H, m), 8.12 (1H, dd, J=4.9, 1.5 Hz), 8.15-8.20 (1H, m), 8.22-8.25 (1H, m), 8.48 (1H, s)

Example 63

3-Isopropoxy-5-{[3-(morpholin-4-ylsulfonyl)benzoyl]amino}-1H-pyrazole hydrochloride The compound (100 mg) obtained in Reference Example 7 was dissolved in THF (2.0 mL), and morpholine (0.10 mL) was added thereto and stirred at room temperature for 18 hours. Ethyl acetate was added to the reaction liquid, then washed with water and saturated brine in that order, and dried with sodium sulfate. The drying agent was removed through filtration, and the solvent was evaporated off under reduced pressure. The residue was purified through silica gel column chromatography (ethyl acetate/hexane=from 0% to 100%, gradient) to give a colorless solid (63 mg). The obtained solid (61 mg) was dissolved in ethyl acetate (2.0 mL), then 4 M hydrochloric acid/ethyl acetate solution (2.0 mL) was added thereto and stirred at room temperature for 18 hours. The formed solid was collected through filtration to give the entitled compound (50 mg, 59%) as a colorless solid.
$^1$H-NMR (DMSO-d$_6$) δ: 1.28 (6H, d, J=6.1 Hz), 2.90 (4H, t, J=4.6 Hz), 3.63 (4H, t, J=4.6 Hz), 4.52-4.66 (1H, m), 5.82 (1H, s), 6.43 (1H, br s), 7.81 (1H, t, J=7.8 Hz), 7.93 (1H, dt, J=8.0, 1.3 Hz), 8.25-8.35 (2H, m), 11.24 (1H, s)

Example 64

3-Isopropoxy-5-({3-[(2-methylpyrrolidin-1-yl)sulfonyl]benzoyl}amino)-1H-pyrazole hydrochloride The entitled compound was produced according to the method of Example 63 but using the compound obtained in Reference Example 7 and 2-methylpyrrolidine as the starting materials.
$^1$H-NMR (DMSO-d$_6$) δ: 1.23 (6H, d, J=6.3 Hz), 1.28 (3H, d, J=6.1 Hz), 1.34-1.49 (2H, m), 1.51-1.65 (1H, m), 1.69-1.85 (1H, m), 3.14 (1H, dt, J=12.8, 5.2 Hz), 3.30-3.40 (1H, m), 3.63-3.75 (1H, m), 4.51-4.66 (1H, m), 5.81 (1H, s), 6.07 (1H, br s), 7.77 (1H, t, J=7.9 Hz), 8.02 (1H, d, J=7.9 Hz), 8.27 (1H, d, J=7.9 Hz), 8.35 (1H, s), 11.22 (1H, s)

Example 65

5-[(3-{[3-(hydroxymethyl)piperidin-1-yl]sulfonyl}benzoyl)amino]-3-isopropoxy-1H-pyrazole hydrochloride The entitled compound was produced according to the method of Example 63 but using the compound obtained in Reference Example 7 and piperidin-3-ylmethanol as the starting materials.
$^1$H-NMR (DMSO-d$_6$) δ: 0.81-0.95 (1H, m), 1.28 (6H, d, J=6.1 Hz), 1.38-1.74 (4H, m), 1.94-2.04 (1H, m), 2.18-2.29 (1H, m), 3.14 (1H, dd, J=10.7, 7.8 Hz), 3.30 (1H, dd, J=10.7, 4.9 Hz), 3.50-3.60 (1H, m), 3.62-3.72 (1H, m), 4.52-4.65 (1H, m), 5.31 (1H, br s), 5.81 (1H, s), 7.79 (1H, t, J=8.0 Hz), 7.88-7.94 (1H, m), 8.24-8.32 (2H, m), 11.20 (1H, s)

Example 66

5-({3-[(3-Hydroxypiperidin-1-yl)sulfonyl}benzoyl]amino)-3-isopropoxy-1H-pyrazole hydrochloride The entitled compound was produced according to the method of Example 63 but using the compound obtained in Reference Example 7 and 3-hydroxypiperidine hydrochloride as the starting materials.
$^1$H-NMR (DMSO-d$_6$) δ: 0.99-1.26 (1H, m), 1.28 (6H, d, J=6.1 Hz), 1.38-1.61 (2H, m), 1.61-1.80 (2H, m), 2.87-3.07 (2H, m), 3.13-3.23 (1H, m), 4.53-4.64 (1H, m), 4.69-4.78 (1H, m), 5.81 (1H, s), 7.79 (1H, t, J=8.0 Hz), 7.89-7.96 (1H, m), 8.25-8.33 (2H, m), 11.17 (1H, s)

Example 67

5-({3-[(4-fluoropiperidin-1-yl)sulfonyl]benzoyl}amino)-3-isopropoxy-1H-pyrazole hydrochloride The entitled compound was produced according to the method of Example 63 but using the compound obtained in Reference Example 7 and 4-fluoropiperidine hydrobromide as the starting materials.

¹H-NMR (DMSO-d₆) δ: 1.28 (6H, d, J=6.1 Hz), 1.69-2.00 (4H, m), 2.89-2.99 (2H, m), 3.04-3.15 (2H, m), 4.53-4.64 (1H, m), 4.64-4.84 (1H, m), 5.82 (1H, s), 6.09 (1H, br s), 7.80 (1H, t, J=8.0 Hz), 7.93-7.98 (1H, m), 8.26-8.32 (2H, m), 11.22 (1H, s)

Example 68

5-({3-[(4,4-difluoropiperidin-1-yl)sulfonyl]benzoyl}amino)-3-isopropoxy-1H-pyrazole hydrochloride The entitled compound was produced according to the method of Example 63 but using the compound obtained in Reference Example 7 and 4,4-difluoropiperidine hydrobromide as the starting materials.

¹H-NMR (DMSO-d₆) δ: 1.28 (6H, d, J=6.1 Hz), 1.99-2.14 (4H, m), 3.12 (4H, t, J=5.6 Hz), 4.54-4.64 (1H, m), 5.83 (1H, s), 6.75 (1H, br s), 7.81 (1H, t, J=7.8 Hz), 7.98 (1H, dt, J=7.8, 1.5 Hz), 8.27-8.34 (2H, m), 11.25 (1H, s)

Example 69

3-Isopropoxy-5-{[3-(piperidin-1-ylsulfonyl)benzoyl}amino]-1H-pyrazole hydrochloride The entitled compound was produced according to the method of Example 63 but using the compound obtained in Reference Example 7 and piperidine as the starting materials.

¹H-NMR (DMSO-d₆) δ: 1.29 (6H, d, J=6.1 Hz), 1.32-1.41 (2H, m), 1.49-1.61 (4H, m), 2.92 (4H, t, J=5.4 Hz), 4.53-4.70 (1H, m), 5.77-5.92 (1H, m), 7.76-7.86 (1H, m), 7.90-7.99 (1H, m), 8.25-8.39 (2H, m), 11.08-11.61 (2H, m)

Example 70

N-(3-isopropoxy-1H-pyrazol-5-yl)-3-(pyrrolidin-1-ylsulfonyl)benzamide hydrochloride The entitled compound was produced according to the method of Example 63 but using the compound obtained in Reference Example 7 and pyrrolidine as the starting materials.

¹H-NMR (CDCl₃) δ: 1.36 (6H, d, J=6.1 Hz), 1.74-1.84 (4H, m), 3.27 (4H, t, J=6.8 Hz), 4.50-4.63 (1H, m), 5.99 (1H, s), 7.66 (1H, t, J=7.8 Hz), 7.99 (1H, dt, J=8.0, 1.5 Hz), 8.14 (1H, dt, J=7.8, 1.5 Hz), 8.30 (1H, t, J=1.5 Hz), 10.24 (1H, s)

Example 71

N-(4-fluorophenyl)-3-(piperidin-1-ylsulfonyl)benzamide

4-Fluoroaniline (41 mg), pyridine (0.06 mL) and N-(3-dimethylaminopropyl)-N'-ethylcarbodiimide hydrochloride (107 mg) were added in that order to a DMF (2.0 mL) solution of 3-(piperidin-1-ylsulfonyl)benzoic acid (100 mg), and stirred at room temperature for 14 hours. Ethyl acetate was added to the reaction liquid, washed twice with 2 M hydrochloric acid, and dried with sodium sulfate. The drying agent was removed through filtration, and the solvent was evaporated off. The residue was purified through silica gel column chromatography (ethyl acetate/hexane=from 5% to 50%, gradient) to give the entitled compound (87 mg, 65%) as a white crystal.

¹H-NMR (CDCl₃) δ: 1.37-1.48 (2H, m), 1.54-1.69 (4H, m), 2.93-3.08 (4H, m), 7.09 (2H, t, J=8.7 Hz), 7.61-7.67 (2H, m), 7.68 (1H, t, J=7.8 Hz), 7.86-7.96 (1H, m), 8.15 (2H, d, J=7.8 Hz), 8.19 (1H, s)

Example 72

3-(Piperidin-1-ylsulfonyl)-N-[4-(trifluoromethyl)phenyl]benzamide

The entitled compound was produced according to the method of Example 71 but using 3-(piperidin-1-ylsulfonyl)benzoic acid (100 mg) and 4-aminobenzotrifluoride (59 mg) as the starting materials.

¹H-NMR (CDCl₃) δ: 1.38-1.47 (2H, m), 1.57-1.67 (4H, m), 3.01 (4H, t, J=5.5 Hz), 7.66 (2H, d, J=8.5 Hz), 7.69 (1H, t, J=7.8 Hz), 7.85 (2H, d, J=8.5 Hz), 7.92 (1H, d, J=7.8 Hz), 8.15-8.20 (1H, m), 8.21 (1H, s), 8.35 (1H, s)

Example 73

N-benzyl-3-(piperidin-1-ylsulfonyl)benzamide

Benzylamine (12 mg), triethylamine (0.047 mL) and 25% dichloromethane solution of 2-chloro-1,3-dimethylimidazolinium chloride (0.11 mL) were added in that order to a chloroform (0.30 mL) solution of 3-(piperidin-1-ylsulfonyl)benzoic acid (30 mg), and stirred at room temperature for 1 hour. The reaction liquid was concentrated and purified through reversed-phase HPLC (0.1% TFA acetonitrile/H₂O=from 10% to 95%, gradient) to give the entitled compound (26 mg, 65%) as a white crystal.

¹H-NMR (CDCl₃) δ: 1.37-1.48 (2H, m), 1.52-1.70 (4H, m), 3.00 (4H, t, J=5.5 Hz), 4.66 (2H, d, J=5.5 Hz), 6.54 (1H, br s), 7.28-7.41 (5H, m), 7.62 (1H, t, J=7.8 Hz), 7.85-7.90 (1H, m), 8.06 (1H, d, J=7.8 Hz), 8.10 (1H, s)

Example 74

2-{[3-(Piperidin-1-ylsulfonyl)benzoyl]amino}pyridine trifluoroacetate

The entitled compound was produced according to the method of Example 73 but using 3-(piperidin-1-ylsulfonyl)benzoic acid and 2-aminopyridine as the starting materials.

¹H-NMR (DMSO-d₆) δ: 1.31-1.41 (2H, m), 1.49-1.60 (4H, m), 2.93 (4H, t, J=5.5 Hz), 7.17-7.24 (1H, m), 7.78 (1H, t, J=7.8 Hz), 7.83-7.97 (2H, m), 8.18 (1H, d, J=8.2 Hz), 8.28-8.35 (2H, m), 8.39-8.44 (1H, m), 11.24 (1H, s)

Example 75

6-{[3-(piperidin-1-ylsulfonyl)benzoyl]amino}quinoline trifluoroacetate

The entitled compound was produced according to the method of Example 73 but using 3-(piperidin-1-ylsulfonyl)benzoic acid and 7-aminoquinoline as the starting materials.

¹H-NMR (DMSO-d₆) δ: 1.30-1.44 (2H, m), 1.49-1.61 (4H, m), 2.94 (4H, t, J=5.5 Hz), 7.70-7.78 (1H, m), 7.85 (1H, t, J=7.6 Hz), 7.97 (1H, d, J=7.8 Hz), 8.10-8.25 (2H, m), 8.30-8.38 (2H, m), 8.64-8.76 (2H, m), 8.96-9.03 (1H, m), 10.97 (1H, s)

Example 76

5-{[3-(piperidin-1-ylsulfonyl)benzoyl]amino}isoquinoline trifluoroacetate

The entitled compound was produced according to the method of Example 73 but using 3-(piperidin-1-ylsulfonyl)benzoic acid and 5-aminoisoquinoline hydrochloride as the starting materials.

$^{1}$H-NMR (DMSO-d$_{6}$) δ: 1.33-1.43 (2H, m), 1.51-1.61 (4H, m), 2.95 (4H, t, J=5.1 Hz), 7.83-7.93 (2H, m), 7.99 (1H, d, J=8.2 Hz), 8.03-8.14 (2H, m), 8.21-8.28 (1H, m), 8.36-8.45 (2H, m), 8.60 (1H, dd, J=6.3, 1.2 Hz), 9.61 (1H, d, J=4.7 Hz), 10.93 (1H, s)

Example 77

N-(4-isopropylphenyl)-3-(piperidin-1-ylsulfonyl)benzamide

The entitled compound was produced according to the method of Example 73 but using 3-(piperidin-1-ylsulfonyl)benzoic acid and 4-isopropylaniline as the starting materials.

$^{1}$H-NMR (CDCl$_{3}$) δ: 1.26 (6H, d, J=7.0 Hz), 1.39-1.49 (2H, m), 1.56-1.74 (4H, m), 2.87-2.98 (1H, m), 3.03 (4H, t, J=5.3 Hz), 7.23-7.29 (2H, m), 7.58 (2H, d, J=8.0 Hz), 7.68 (1H, t, J=8.0 Hz), 7.86-7.96 (2H, m), 8.14 (1H, d, J=8.0 Hz), 8.18 (1H, s)

Example 78

N-(2-phenylethyl)-3-(piperidin-1-ylsulfonyl)benzamide

The entitled compound was produced according to the method of Example 73 but using 3-(piperidin-1-ylsulfonyl)benzoic acid and 2-phenylethylamine as the starting materials.

$^{1}$H-NMR (CDCl$_{3}$) δ: 1.38-1.48 (2H, m), 1.61-1.70 (4H, m), 2.93-3.02 (6H, m), 3.74 (2H, q, J=6.5 Hz), 6.23 (1H, br s), 7.21-7.28 (3H, m), 7.30-7.37 (2H, m), 7.57-7.63 (1H, m), 7.86 (1H, d, J=8.2 Hz), 7.94-8.00 (2H, m)

Example 79

N-[4-(methylthio)phenyl]-3-(piperidin-1-ylsulfonyl)benzamide

The entitled compound was produced according to the method of Example 73 but using 3-(piperidin-1-ylsulfonyl)benzoic acid and 4-methylthioaniline as the starting materials.

$^{1}$H-NMR (CDCl$_{3}$) δ: 1.39-1.49 (2H, m), 1.61-1.69 (4H, m), 2.50 (3H, s), 3.02 (4H, t, J=5.5 Hz), 7.30 (2H, d, J=8.6 Hz), 7.61 (2H, d, J=8.6 Hz), 7.68 (1H, t, J=7.8 Hz), 7.89-7.99 (2H, m), 8.14 (1H, d, J=7.8 Hz), 8.17 (1H, s)

Example 80

N-(2-methoxyphenyl)-3-(piperidin-1-ylsulfonyl)benzamide

The entitled compound was produced according to the method of Example 73 but using 3-(piperidin-1-ylsulfonyl)benzoic acid and 2-methoxyaniline as the starting materials.

$^{1}$H-NMR (CDCl$_{3}$) δ: 1.39-1.49 (2H, m), 1.61-1.76 (4H, m), 3.04 (4H, t, J=5.5 Hz), 3.94 (3H, s), 6.94 (1H, d, J=7.8 Hz), 7.04 (1H, t, J=7.6 Hz), 7.09-7.16 (1H, m), 7.68 (1H, t, J=7.8 Hz), 7.94 (1H, d, J=7.8 Hz), 8.11 (1H, d, J=7.8 Hz), 8.23 (1H, s), 8.48 (1H, d, J=8.2 Hz), 8.54 (1H, s)

Example 81

N-(3-methoxyphenyl)-3-(piperidin-1-ylsulfonyl)benzamide

The entitled compound was produced according to the method of Example 73 but using 3-(piperidin-1-ylsulfonyl)benzoic acid and 3-methoxyaniline as the starting materials.

$^{1}$H-NMR (CDCl$_{3}$) δ: 1.39-1.49 (2H, m), 1.60-1.77 (4H, m), 3.02 (4H, t, J=5.5 Hz), 3.85 (3H, s), 6.71-6.78 (1H, m), 7.16 (1H, d, J=8.2 Hz), 7.26-7.33 (1H, m), 7.42 (1H, s), 7.68 (1H, t, J=7.8 Hz), 7.92 (1H, d, J=7.8 Hz), 7.96 (1H, s), 8.14 (1H, d, J=8.2 Hz), 8.18 (1H, s)

Example 82

N-isoxazol-3-yl-3-(piperidin-1-ylsulfonyl)benzamide

The entitled compound was produced according to the method of Example 73 but using 3-(piperidin-1-ylsulfonyl)benzoic acid and 3-aminoisoxazole as the starting materials.

$^{1}$H-NMR (CDCl$_{3}$) δ: 1.39-1.49 (2H, m), 1.62-1.73 (4H, m), 3.04 (4H, t, J=5.5 Hz), 7.23 (1H, d, J=1.6 Hz), 7.72 (1H, t, J=7.8 Hz), 7.99 (1H, d, J=7.8 Hz), 8.18 (1H, d, J=7.8 Hz), 8.28-8.32 (1H, m), 8.38 (1H, d, J=1.6 Hz), 9.25 (1H, s)

Example 83

3-(Piperidin-1-ylsulfonyl)-N-[(1S)-1,2,3,4-tetrahydronaphthalen-1-yl]benzamide The entitled compound was produced according to the method of Example 73 but using 3-(piperidin-1-ylsulfonyl)benzoic acid and (S)-(+)-1,2,3,4-tetrahydro-1-naphthylamine as the starting materials.

$^{1}$H-NMR (CDCl$_{3}$) δ: 1.38-1.50 (2H, m), 1.60-1.70 (4H, m), 1.84-2.05 (3H, m), 2.11-2.23 (1H, m), 2.75-2.95 (2H, m), 3.01 (4H, t, J=5.5 Hz), 5.36-5.46 (1H, m), 6.34-6.43 (1H, m), 7.14-7.25 (3H, m), 7.31-7.35 (1H, m), 7.62 (1H, t, J=7.8 Hz), 7.85-7.90 (1H, m), 8.01-8.06 (1H, m), 8.07-8.11 (1H, m)

Example 84

N-(4-methylphenyl)-3-(piperidin-1-ylsulfonyl)benzamide

The entitled compound was produced according to the method of Example 73 but using 3-(piperidin-1-ylsulfonyl)benzoic acid and 4-methylaniline as the starting materials.

$^{1}$H-NMR (CDCl$_{3}$) δ: 1.39-1.49 (2H, m), 1.61-1.70 (4H, m), 2.36 (3H, s), 3.03 (4H, t, J=5.1 Hz), 7.20 (2H, d, J=8.2 Hz), 7.54 (2H, d, J=8.2 Hz), 7.68 (1H, t, J=7.8 Hz), 7.85 (1H, s), 7.92 (1H, d, J=7.8 Hz), 8.14 (1H, d, J=7.8 Hz), 8.17 (1H, s)

Example 85

N-(2,3-dihydro-1H-inden-1-yl)-3-(piperidin-1-ylsulfonyl)benzamide

The entitled compound was produced according to the method of Example 73 but using 3-(piperidin-1-ylsulfonyl)benzoic acid and 1-aminoindane as the starting materials.

¹H-NMR (CDCl₃) δ: 1.38-1.49 (2H, m), 1.61-1.70 (4H, m), 1.91-2.04 (1H, m), 2.66-2.78 (1H, m), 2.89-3.13 (2H, m), 3.01 (4H, t, J=5.5 Hz), 5.71 (1H, q, J=7.6 Hz), 6.40 (1H, d, J=9.0 Hz), 7.21-7.33 (3H, m), 7.36 (1H, d, J=7.4 Hz), 7.63 (1H, t, J=7.8 Hz), 7.88 (1H, d, J=7.8 Hz), 8.06 (1H, d, J=7.8 Hz), 8.09 (1H, s)

Example 86

N-(3-phenylpropyl)-3-(piperidin-1-ylsulfonyl)benzamide

The entitled compound was produced according to the method of Example 73 but using 3-(piperidin-1-ylsulfonyl)benzoic acid and 3-phenylpropylamine as the starting materials.

¹H-NMR (CDCl₃) δ: 1.36-1.47 (2H, m), 1.61-1.67 (4H, m), 1.96-2.04 (2H, m), 2.74 (2H, t, J=7.4 Hz), 3.00 (4H, t, J=5.5 Hz), 3.53 (2H, q, J=6.6 Hz), 6.17 (1H, br s), 7.16-7.34 (5H, m), 7.60 (1H, t, J=7.8 Hz), 7.86 (1H, d, J=7.8 Hz), 7.92 (1H, d, J=7.8 Hz), 8.02 (1H, s)

Example 87

N-(4-phenoxyphenyl)-3-(piperidin-1-ylsulfonyl)benzamide

The entitled compound was produced according to the method of Example 73 but using 3-(piperidin-1-ylsulfonyl)benzoic acid and 4-phenyloxyaniline as the starting materials.

¹H-NMR (CDCl₃) δ: 1.38-1.49 (2H, m), 1.60-1.71 (4H, m), 3.03 (4H, t, J=5.1 Hz), 6.98-7.08 (4H, m), 7.09-7.14 (1H, m), 7.31-7.38 (2H, m), 7.63 (2H, d, J=8.6 Hz), 7.69 (1H, t, J=7.8 Hz), 7.89-7.99 (2H, m), 8.15 (1H, d, J=7.8 Hz), 8.18 (1H, s)

Example 88

N-phenyl-3-(piperidin-1-ylsulfonyl)benzamide

The entitled compound was produced according to the method of Example 73 but using 3-(piperidin-1-ylsulfonyl)benzoic acid and aniline as the starting materials.

¹H-NMR (CDCl₃) δ: 1.38-1.48 (2H, m), 1.59-1.71 (4H, m), 3.02 (4H, t, J=5.1 Hz), 7.19 (1H, t, J=7.4 Hz), 7.40 (2H, t, J=7.8 Hz), 7.63-7.73 (3H, m), 7.92 (1H, d, J=7.8 Hz), 7.97 (1H, s), 8.15 (1H, d, J=7.8 Hz), 8.19 (1H, s)

Example 89

N-(2-chlorophenyl)-3-(piperidin-1-ylsulfonyl)benzamide

The entitled compound was produced according to the method of Example 73 but using 3-(piperidin-1-ylsulfonyl)benzoic acid and 2-chloroaniline as the starting materials.

¹H-NMR (CDCl₃) δ: 1.40-1.49 (2H, m), 1.62-1.71 (4H, m), 3.05 (4H, t, J=5.4 Hz), 7.13 (1H, td, J=7.8, 1.5 Hz), 7.33-7.39 (1H, m), 7.45 (1H, dd, J=7.8, 1.5 Hz), 7.71 (1H, t, J=7.8 Hz), 7.97 (1H, dt, J=8.0, 1.5 Hz), 8.12 (1H, dt, J=7.8, 1.5 Hz), 8.28 (1H, t, J=1.7 Hz), 8.43 (1H, s), 8.51 (1H, dd, J=8.3, 1.5 Hz)

Example 90

N-(3-chlorophenyl)-3-(piperidin-1-ylsulfonyl)benzamide

The entitled compound was produced according to the method of Example 73 but using 3-(piperidin-1-ylsulfonyl)benzoic acid and 3-chloroaniline as the starting materials.

¹H-NMR (CDCl₃) δ: 1.38-1.48 (2H, m), 1.59-1.69 (4H, m), 3.01 (4H, t, J=5.6 Hz), 7.15-7.19 (1H, m), 7.32 (1H, t, J=8.0 Hz), 7.50-7.55 (1H, m), 7.69 (1H, t, J=7.8 Hz), 7.82-7.85 (1H, m), 7.92 (1H, dt, J=7.8, 1.5 Hz), 8.13-8.17 (2H, m), 8.17-8.20 (1H, m)

Example 91

N-(4-isopropoxyphenyl)-3-(piperidin-1-ylsulfonyl)benzamide

The entitled compound was produced according to the method of Example 73 but using 3-(piperidin-1-ylsulfonyl)benzoic acid and 4-isopropoxyaniline as the starting materials.

¹H-NMR (CDCl₃) δ: 1.34 (6H, d, J=5.9 Hz), 1.38-1.48 (2H, m), 1.59-1.69 (4H, m), 3.01 (4H, t, J=5.1 Hz), 4.48-4.60 (1H, m), 6.91 (2H, d, J=8.8 Hz), 7.55 (2H, d, J=8.8 Hz), 7.67 (1H, t, J=7.8 Hz), 7.90 (1H, d, J=7.8 Hz), 7.98 (1H, s), 8.14 (1H, d, J=7.8 Hz), 8.17 (1H, s)

Example 92

N-(4-acetylphenyl)-3-(piperidin-1-ylsulfonyl)benzamide 1-(4-aminophenyl)ethanone (151 mg), O-(7-azabenzotriazol-1-yl)-1,1,3,3-tetramethyluronium hexafluorophosphate (565 mg) and N,N-diisopropylethylamine (0.39 mL) were added in that order to a DMF (4.0 mL) solution of 3-(piperidin-1-ylsulfonyl)benzoic acid (200 mg), and stirred at room temperature for 2 hours. Ethyl acetate was added to the reaction liquid, washed three times with water, and dried with sodium sulfate. The drying agent was removed through filtration, and the solvent was evaporated off under reduced pressure. The residue was purified through silica gel column chromatography (ethyl acetate/hexane=from 0% to 80%, gradient) to give the entitled compound (117 mg, 41%) as a white crystal.

¹H-NMR (CDCl₃) δ: 1.38-1.47 (2H, m), 1.58-1.67 (4H, m), 2.61 (3H, s), 2.97-3.04 (4H, m), 7.68 (1H, t, J=7.8 Hz), 7.83 (2H, d, J=8.8 Hz), 7.89-7.93 (1H, m), 8.00 (2H, d, J=8.8 Hz), 8.15-8.19 (1H, m), 8.20-8.23 (1H, m), 8.43 (1H, s)

Example 93

N-[4-(1-hydroxyethyl)phenyl]-3-(piperidin-1-ylsulfonyl)benzamide

Sodium borohydride (8.8 mg) was added to an ethanol (2.0 mL) solution of the compound (30.0 mg) obtained in Example 92, and stirred overnight at room temperature. Aqueous saturated ammonium chloride solution was added to the reaction liquid, extracted three times with ethyl acetate, and dried with sodium sulfate. The drying agent was removed through filtration, and the solvent was evaporated off under reduced pressure. The residue was purified through silica gel column chromatography (ethyl acetate/hexane=from 0% to 80%, gradient) to give the entitled compound (29.7 mg, 98%) as a white solid.

$^1$H-NMR (CDCl$_3$) δ: 1.40-1.47 (2H, m), 1.51 (3H, d, J=6.7 Hz), 1.57-1.75 (4H, m), 2.98-3.06 (4H, m), 4.89-4.97 (1H, m), 7.40 (2H, d, J=8.2 Hz), 7.60-7.74 (3H, m), 7.91 (1H, d, J=8.2 Hz), 8.05 (1H, s), 8.15 (1H, d, J=7.8 Hz), 8.18 (1H, s)

Example 94

N-[4-(1-hydroxy-1-methylethyl)phenyl]-3-(piperidin-1-ylsulfonyl)benzamide

With cooling with ice, methyllithium (0.66 mL, 0.98 M diethyl ether solution) was dropwise added to a diethyl ether (1.0 mL) solution of the compound (50.0 mg) obtained in Example 92, and stirred for 1 hour with cooling with ice. After heated up to room temperature, water was added to the reaction liquid, and then extracted three times with ethyl acetate. This was dried with sodium sulfate, then the drying agent was removed through filtration, and the solvent was evaporated off under reduced pressure. The residue was purified through silica gel column chromatography (ethyl acetate/hexane=from 0% to 80%, gradient) to give the entitled compound (51.1 mg, 99%) as a white solid.

$^1$H-NMR (CDCl$_3$) δ: 1.40-1.47 (2H, m), 1.59 (6H, s), 1.59-1.67 (4H, m), 2.98-3.04 (4H, m), 7.49-7.52 (2H, m), 7.60-7.69 (3H, m), 7.90 (1H, d, J=7.6 Hz), 8.14-8.19 (3H, m)

Example 95

N-[5-(difluoromethoxy)pyridin-2-yl]-3-(piperidin-1-ylsulfonyl)benzamide

The entitled compound was produced according to the method of Example 92 but using 3-(piperidin-1-ylsulfonyl)benzoic acid and 5-(difluoromethoxy)pyridine-2-amine as the starting materials.

$^1$H-NMR (CDCl$_3$) δ: 1.37-1.47 (2H, m), 1.57-1.68 (4H, m), 2.97-3.03 (4H, m), 7.48 (2H, d, J=8.8 Hz), 7.65-7.72 (1H, m), 7.69 (2H, d, J=8.8 Hz), 7.88-7.93 (1H, m), 8.12-8.20 (3H, m)

Example 96

N-(2,6-dimethoxypyridin-3-yl)-3-(piperidin-1-ylsulfonyl)benzamide

The entitled compound was produced according to the method of Example 92 but using 3-(piperidin-1-ylsulfonyl)benzoic acid and 2,6-dimethoxypyridine-3-amine as the starting materials.

$^1$H-NMR (CDCl$_3$) δ: 1.39-1.48 (2H, m), 1.59-1.70 (4H, m), 3.04 (4H, t, J=5.6 Hz), 3.92 (3H, s), 4.04 (3H, s), 6.38 (1H, d, J=8.8 Hz), 7.68 (1H, t, J=7.8 Hz), 7.90-7.96 (1H, m), 8.06-8.14 (2H, m), 8.19-8.23 (1H, m), 8.59 (1H, d, J=8.8 Hz)

Example 97

N-(2-methoxypyridin-3-yl)-3-(piperidin-1-ylsulfonyl)benzamide

The entitled compound was produced according to the method of Example 92 but using 3-(piperidin-1-ylsulfonyl)benzoic acid and 2-methoxypyridine-3-amine as the starting materials.

$^1$H-NMR (CDCl$_3$) δ: 1.40-1.49 (2H, m), 1.62-1.71 (4H, m), 3.04 (4H, t, J=5.6 Hz), 4.08 (3H, s), 6.98 (1H, dd, J=7.8, 4.9 Hz), 7.70 (1H, t, J=7.8 Hz), 7.91-7.98 (2H, m), 8.07-8.13 (1H, m), 8.22-8.25 (1H, m), 8.39 (1H, s), 8.72 (1H, dd, J=7.8, 1.5 Hz)

Example 98

N-(3-hydroxypyridin-2-yl)-3-(piperidin-1-ylsulfonyl)benzamide

The entitled compound was produced according to the method of Example 92 but using 3-(piperidin-1-ylsulfonyl)benzoic acid and 2-aminopyridin-3-ol as the starting materials.

$^1$H-NMR (CDCl$_3$) δ: 1.37-1.47 (2H, m), 1.58-1.69 (4H, m), 2.99 (4H, t, J=5.4 Hz), 7.17 (1H, dd, J=8.0, 4.6 Hz), 7.44 (1H, dd, J=8.3, 1.5 Hz), 7.70 (1H, t, J=7.8 Hz), 7.83-7.88 (1H, m), 7.95-8.00 (1H, m), 8.21-8.26 (1H, m), 8.34-8.39 (1H, m)

Example 99

N-(3-methoxypyridin-2-yl)-3-(piperidin-1-ylsulfonyl)benzamide

The entitled compound was produced according to the method of Example 92 but using 3-(piperidin-1-ylsulfonyl)benzoic acid and 3-methoxypyridine-2-amine as the starting materials.

$^1$H-NMR (CDCl$_3$) δ: 1.38-1.48 (2H, m), 1.59-1.69 (4H, m), 3.01 (4H, t, J=5.4 Hz), 3.93 (3H, s), 7.12 (1H, dd, J=8.3, 4.9 Hz), 7.21-7.26 (1H, m), 7.67 (1H, t, J=7.8 Hz), 7.90-7.95 (1H, m), 8.08-8.13 (1H, m), 8.15-8.19 (1H, m), 8.21-8.25 (1H, m)

Example 100

N-(6-isopropoxypyridin-3-yl)-3-(piperidin-1-ylsulfonyl)benzamide

The entitled compound was produced according to the method of Example 92 but using 3-(piperidin-1-ylsulfonyl)benzoic acid and 6-isopropoxypyridine-3-amine as the starting materials.

$^1$H-NMR (CDCl$_3$) δ: 1.35 (6H, d, J=6.3 Hz), 1.39-1.47 (2H, m), 1.58-1.69 (4H, m), 3.02 (4H, t, J=5.4 Hz), 5.22-5.33 (1H, m), 6.73 (1H, d, J=8.8 Hz), 7.68 (1H, t, J=7.8 Hz), 7.88-7.94 (1H, m), 7.95-8.04 (1H, m), 8.16 (1H, d, J=7.8 Hz), 8.20 (1H, s), 8.30-8.35 (1H, m).

Example 101

N-(6-phenoxypyridin-3-yl)-3-(piperidin-1-ylsulfonyl)benzamide

The entitled compound was produced according to the method of Example 92 but using 3-(piperidin-1-ylsulfonyl)benzoic acid and 6-phenoxypyridine-3-amine as the starting materials.

$^1$H-NMR (CDCl$_3$) δ: 1.35-1.45 (2H, m), 1.54-1.64 (4H, m), 2.98 (4H, t, J=5.4 Hz), 6.93 (1H, d, J=8.8 Hz), 7.09-7.14 (2H, m), 7.16-7.22 (1H, m), 7.35-7.42 (2H, m), 7.66 (1H, t, J=7.8 Hz), 7.85-7.90 (1H, m), 8.13-8.24 (3H, m), 8.39 (1H, d, J=2.4 Hz), 8.54 (1H, s)

Example 102

N-(6-methoxypyridin-3-yl)-3-(piperidin-1-ylsulfonyl)benzamide

The entitled compound was produced according to the method of Example 92 but using 3-(piperidin-1-ylsulfonyl)benzoic acid and 6-methoxypyridine-3-amine as the starting materials.

$^1$H-NMR (CDCl$_3$) δ: 1.36-1.46 (2H, m), 1.56-1.65 (4H, m), 2.98 (4H, t, J=5.4 Hz), 3.94 (3H, s), 6.78 (1H, d, J=8.8 Hz), 7.66 (1H, t, J=7.8 Hz), 7.86-7.90 (1H, m), 8.03 (1H, dd, J=8.8, 2.9 Hz), 8.17 (1H, d, J=7.8 Hz), 8.23 (1H, s), 8.39 (1H, d, J=2.9 Hz), 8.44 (1H, s)

Example 103

N-(3-methylpyridin-2-yl)-3-(piperidin-1-ylsulfonyl)benzamide

The entitled compound was produced according to the method of Example 92 but using 3-(piperidin-1-ylsulfonyl)benzoic acid and 3-methylpyridine-2-amine as the starting materials.

$^1$H-NMR (CDCl$_3$) δ: 1.37-1.47 (2H, m), 1.57-1.67 (4H, m), 2.35 (3H, s), 2.95 (4H, t, J=5.6 Hz), 7.11-7.21 (1H, m), 7.61-7.68 (2H, m), 7.91 (1H, dt, J=7.8, 1.5 Hz), 8.14-8.31 (2H, m), 8.34 (1H, s), 9.36 (1H, s)

Example 104

N-(3-methoxypyridin-2-yl)-3-(pyrrolidin-1-ylsulfonyl)benzamide

The entitled compound was produced according to the method of Example 92 but using 3-(pyrrolidin-1-ylsulfonyl)benzoic acid and 3-methylpyridine-2-amine as the starting materials.

$^1$H-NMR (CDCl$_3$) δ: 1.75-1.82 (4H, m), 3.24-3.31 (4H, m), 3.94 (3H, s), 7.13 (1H, dd, J=8.3, 4.9 Hz), 7.25 (1H, dd, J=8.3, 1.0 Hz), 7.68 (1H, t, J=7.8 Hz), 8.02 (1H, d, J=7.8 Hz), 8.12 (1H, dd, J=4.9, 1.0 Hz), 8.18 (1H, d, J=7.8 Hz), 8.30 (1H, s)

Example 105

N-(3-cyclopropyl-1H-pyrazol-5-yl)-3-(piperidin-1-ylsulfonyl)benzamide

The entitled compound was produced according to the method of Example 92 but using 3-(piperidin-1-ylsulfonyl)benzoic acid and 5-cyclopropyl-1H-pyrazole-3-amine as the starting materials.

$^1$H-NMR (CDCl$_3$) δ: 0.72-0.80 (2H, m), 0.94-1.03 (2H, m), 1.38-1.49 (2H, m), 1.60-1.71 (4H, m), 1.83-1.94 (1H, m), 3.03 (4H, t, J=5.6 Hz), 6.43 (1H, s), 7.66 (1H, t, J=7.8 Hz), 7.90 (1H, d, J=7.8 Hz), 8.15 (1H, d, J=7.8 Hz), 8.24 (1H, s)

Example 106

N-(5-bromo-3-methoxypyridin-2-yl)-3-(piperidin-1-ylsulfonyl)benzamide

The entitled compound was produced according to the method of Example 92 but using 3-(piperidin-1-ylsulfonyl)benzoic acid and 5-bromo-3-methoxypyridine-2-amine as the starting materials.

$^1$H-NMR (CDCl$_3$) δ: 1.39-1.49 (2H, m), 1.59-1.74 (4H, m), 3.01 (4H, t, J=5.4 Hz), 3.94 (3H, s), 7.36 (1H, d, J=2.0 Hz), 7.69 (1H, t, J=7.8 Hz), 7.94 (1H, d, J=7.8 Hz), 8.12-8.23 (3H, m), 8.43 (1H, s)

Example 107

N-(3-methoxy-5-vinylpyridin-2-yl)-3-(piperidin-1-ylsulfonyl)benzamide

At room temperature, [1,1'-bis(diphenylphosphino)ferrocene]dichloropalladium(II) (9.7 mg), potassium vinyltrifluoroborate (10.6 mg) and triethylamine (0.010 mL) were added in that order to an n-propanol (1.0 mL) solution of the compound (30.0 mg) obtained in Example 106, and stirred at 80° C. for 10 hours. After left cooled, ethyl acetate was added to the reaction liquid, then washed three times with water, and dried with sodium sulfate. The drying agent was removed through filtration, and the solvent was evaporated off under reduced pressure. The residue was purified through silica gel column chromatography (NH Biotage Column, ethyl acetate/hexane=from 0% to 80%, gradient) to give the entitled compound (11.0 mg, 42%) as a colorless oily substance.

$^1$H-NMR (CDCl$_3$) δ: 1.38-1.48 (2H, m), 1.59-1.69 (4H, m), 3.01 (4H, t, J=5.1 Hz), 3.96 (3H, s), 5.37 (1H, d, J=10.7 Hz), 5.78 (1H, d, J=17.6 Hz), 6.72 (1H, dd, J=17.6, 10.7 Hz), 7.28 (1H, s), 7.68 (1H, t, J=7.8 Hz), 7.93 (1H, d, J=7.8 Hz), 8.09 (1H, s), 8.17 (1H, d, J=7.8 Hz), 8.22 (1H, s)

Example 108

N-(5-ethyl-3-methoxypyridin-2-yl)-3-(piperidin-1-ylsulfonyl)benzamide

10% palladium-carbon (3.0 mg) as a catalyst was added to an ethanol (2.0 mL) solution of the compound (9.0 mg) obtained in Example 107, and stirred overnight in a hydrogen atmosphere at room temperature. The catalyst was removed through filtration, the solvent was evaporated off under reduced pressure, and the resulting residue was purified through silica gel column chromatography (methanol/chloroform=from 0% to 20%, gradient) to give the entitled compound (8.5 mg, 94%) as a colorless oily substance.

$^1$H-NMR (CDCl$_3$) δ: 1.28 (3H, t, J=7.6 Hz), 1.39-1.47 (2H, m), 1.61-1.69 (4H, m), 2.68 (2H, q, J=7.6 Hz), 3.01 (4H, t, J=5.4 Hz), 3.92 (3H, s), 7.09 (1H, d, J=1.5 Hz), 7.67 (1H, t, J=7.8 Hz), 7.93 (1H, d, J=7.8 Hz), 7.96 (1H, d, J=1.5 Hz), 8.18 (1H, d, J=7.8 Hz), 8.22 (1H, s)

Example 109

N-(3-methoxy-5-phenylpyridin-2-yl)-3-(pyrrolidin-1-ylsulfonyl)benzamide (Step 1) Production of N-(5-bromo-3-methoxypyridin-2-yl)-3-(pyrrolidin-1-ylsulfonyl)benzamide The intended substance was produced according to the method of Example 92 but using 3-(pyrrolidin-1-ylsulfonyl)benzoic acid and 5-bromo-3-methoxypyridine-2-amine as the starting materials.

(Step 2) Production of N-(3-methoxy-5-phenylpyridin-2-yl)-3-(pyrrolidin-1-ylsulfonyl)benzamide At room temperature, tetrakistriphenylphosphine palladium (13.1 mg), phenylboronic acid (18.0 mg), and aqueous 2 M sodium carbonate solution (0.2 mL) were added in that order to an ethylene glycol dimethyl ether (1.0 mL) solution of the compound (50 mg) obtained in the step 1, and with irradiation with microwaves, this was stirred at 180° C. for 20 minutes. The reaction liquid was diluted with ethyl acetate, and washed with aqueous saturated sodium hydrogencarbonate solution. The organic layer was dried with sodium sulfate, then filtered, and concentrated under reduced pressure. The residue was purified through reversed-phase HPLC (0.1% TFA acetonitrile/$H_2O$=from 10% to 90%, gradient), and further purified through preparative thin-layer chromatography (NH silica gel, methanol/chloroform=10%) to give the entitled compound (14.0 mg, 28%) as a white solid.

$^1$H-NMR (CDCl$_3$) δ: 1.75-1.82 (4H, m), 3.25-3.32 (4H, m), 4.00 (3H, s), 7.38-7.44 (2H, m), 7.46-7.52 (2H, m), 7.56-7.61 (2H, m), 7.69 (1H, t, J=7.8 Hz), 8.02 (1H, dt, J=8.0, 1.5 Hz), 8.20 (1H, dt, J=7.8, 1.5 Hz), 8.33 (1H, t, J=1.5 Hz), 8.35 (1H, d, J=2.0 Hz)

Example 110

N-(3-methoxy-5-phenoxypyridin-2-yl)-3-(pyrrolidin-1-ylsulfonyl)benzamide

Phenol (21.4 mg), cesium carbonate (74.0 mg), copper(I) chloride (11.2 mg) and 2,2,6,6-tetramethylheptane-3,5-dione (2.1 mg) were added to an N-methylpyrrolidine (1.0 mL) solution of the compound (50.0 mg) obtained in Example 109 (Step 1), and with irradiation with microwaves, this was stirred at 180° C. for 20 minutes. The reaction liquid was diluted with ethyl acetate, and washed with water. The organic layer was dried with sodium sulfate, then filtered, and concentrated under reduced pressure. The residue was purified through reversed-phase HPLC (0.1% TFA acetonitrile/$H_2O$=from 10% to 90%, gradient), and further purified through preparative thin-layer chromatography (NH silica gel, methanol/chloroform=10%) to give the entitled compound (4.0 mg, 8%) as a colorless oily substance.

$^1$H-NMR (CDCl$_3$) δ: 1.70-1.83 (4H, m), 3.27-3.33 (4H, m), 3.88 (3H, s), 7.00-7.06 (3H, m), 7.16-7.19 (1H, m), 7.37-7.41 (2H, m), 7.69 (1H, t, J=7.4 Hz), 7.87 (1H, s), 8.02 (1H, d, J=7.4 Hz), 8.17 (1H, d, J=7.4 Hz), 8.30 (1H, s), 8.45 (1H, br s)

Example 111

N-[3-methoxy-5-(phenylthio)pyridin-2-yl]-3-(pyrrolidin-1-ylsulfonyl)benzamide

The entitled compound was produced according to the method of Reference Example 8 (step 1) but using the compound obtained in Example 109 (step 1) and benzenethiol as the starting materials.

$^1$H-NMR (CDCl$_3$) δ: 1.70-1.83 (4H, m), 3.20-3.33 (4H, m), 3.87 (3H, s), 7.18-7.37 (6H, m), 7.69 (1H, t, J=7.8 Hz), 8.02 (1H, d, J=7.8 Hz), 8.10 (1H, d, J=2.0 Hz), 8.17 (1H, d, J=7.8 Hz), 8.29 (1H, s), 8.55 (1H, br s)

Example 112

N-[3-methoxy-5-(phenylsulfonyl)pyridin-2-yl]-3-(pyrrolidin-1-ylsulfonyl)benzamide m-chloroperbenzoic acid (28.0 mg) was added to a chloroform (1.0 mL) solution of the compound (51.0 mg) obtained in Example 111, and stirred overnight at room temperature. The reaction solvent was concentrated under reduced pressure, and the residue was purified through preparative thin-layer chromatography (NH silica gel, ethyl acetate 100%) to give the entitled compound (14.0 mg, 28%) as a white solid.

$^1$H-NMR (CDCl$_3$) δ: 1.74-1.84 (4H, m), 3.21-3.32 (4H, m), 4.02 (3H, s), 7.51-8.00 (7H, m), 8.02-8.07 (1H, m), 8.14 (1H, d, J=7.8 Hz), 8.26 (1H, d, J=1.5 Hz), 8.62 (1H, d, J=2.0 Hz), 8.67 (1H, s)

Example 113

N-(3-ethoxypyridin-2-yl)-3-(pyrrolidin-1-ylsulfonyl)benzamide

The entitled compound was produced according to the method of Example 92 but using 3-(pyrrolidin-1-ylsulfonyl)benzoic acid and 3-ethoxypyridine-2-amine as the starting materials.

$^1$H-NMR (CDCl$_3$) δ: 1.49 (3H, t, J=7.0 Hz), 1.75-1.83 (4H, m), 3.25-3.31 (4H, m), 4.17 (2H, q, J=7.0 Hz), 7.10 (1H, dd, J=7.8, 4.9 Hz), 7.22 (1H, dd, J=8.3, 1.5 Hz), 7.69 (1H, t, J=7.8 Hz), 8.02 (1H, dt, J=7.8, 1.5 Hz), 8.10 (1H, dd, J=4.9, 1.5 Hz), 8.18 (1H, dt, J=7.8, 1.5 Hz), 8.30 (1H, t, J=1.5 Hz)

Example 114

N-(4-cyano-1H-imidazol-5-yl)-3-(piperidin-1-ylsulfonyl)benzamide

The entitled compound was produced according to the method of Example 92 but using 3-(piperidin-1-ylsulfonyl)benzoic acid and 5-amino-1H-imidazole-4-carbonitrile as the starting materials.

$^1$H-NMR (CDCl$_3$) δ: 1.38-1.47 (2H, m), 1.59-1.68 (4H, m), 3.03 (4H, t, J=5.4 Hz), 7.61 (1H, s), 7.70 (1H, t, J=7.8 Hz), 7.95 (1H, d, J=7.8 Hz), 8.23 (1H, d, J=7.8 Hz), 8.37 (1H, s), 10.42 (1H, s)

Example 115

N-(3-cyclopropyl-1H-pyrazol-5-yl)-3-(pyrrolidin-1-ylsulfonyl)benzamide

The entitled compound was produced according to the method of Example 92 but using 3-(pyrrolidin-1-ylsulfonyl)benzoic acid and 5-cyclopropyl-1H-pyrazole-3-amine as the starting materials.

$^1$H-NMR (CDCl$_3$) δ: 0.72-0.80 (2H, m), 0.94-1.03 (2H, m), 1.74-1.84 (4H, m), 1.85-1.95 (1H, m), 3.20-3.34 (4H, m), 6.41 (1H, s), 7.64 (1H, t, J=7.8 Hz), 7.97 (1H, d, J=7.8 Hz), 8.12 (1H, d, J=7.8 Hz), 8.30 (1H, s), 11.36 (1H, s)

Example 116

N-(3-isopropoxy-1H-pyrazol-5-yl)-3-(pyridin-2-ylsulfonyl)benzamide (Step 1) Production of N-(5-isopropoxy-1-{[2-(trimethylsilyl)ethoxy]methyl}-1H-pyrazol-3-yl)-3-(pyridin-2-ylsulfonyl)benzamide Oxalyl dichloride (0.88 mL) and DMF (0.20 mL) were added in that order to a chloroform (50 mL) solution of the compound (2.43 g) obtained in Reference Example 8, and stirred at room temperature for 2 hours. The reaction solvent was evaporated off under reduced pressure, and the residue was dissolved in chloroform (50 mL). Triethylamine (4.68 mL) and 5-isopropoxy-1-{[2-(trimethylsilyl)ethoxy]methyl}-1H-pyrazole-3-amine (2.28 g) obtained in Reference Example 9 were added thereto in that order, and stirred at room temperature for 10 minutes. Aqueous saturated ammonium chloride solution was added to the reaction liquid, then extracted with chloroform and dried with sodium sulfate. The drying agent was removed through filtration, and the solvent was evaporated off under reduced pressure. The residue was purified through silica gel column chromatography (ethyl acetate/hexane=from 0% to 60%, gradient) to give the entitled compound (3.38 g, 78%) as a pale yellow oily substance.

(Step 2) Production of N-(3-isopropoxy-1H-pyrazol-5-yl)-3-(pyridin-2-ylsulfonyl)benzamide The compound (3.38 g) obtained in the step 1 was dissolved in a mixed solvent of trifluoroacetic acid (27 mL)/distilled water (3.0 mL), and stirred at room temperature for 4 hours. Aqueous saturated sodium hydrogencarbonate solution was added to the reaction liquid, then extracted with ethyl acetate, and dried with sodium sulfate. The drying agent was removed through filtration, and the solvent was evaporated off under reduced pressure. The residue was purified through silica gel column chromatography (methanol/chloroform=from 0% to 20%, gradient), and the resulting compound was further purified through recrystallization (heptane/ethanol) to give the entitled compound (1.42 g, 56%) as a white crystal.
$^1$H-NMR (CDCl$_3$) δ: 1.36 (6H, d, J=6.3 Hz), 4.54-4.66 (1H, m), 5.94 (1H, s), 7.48-7.52 (1H, m), 7.67 (1H, t, J=7.8 Hz), 7.97 (1H, td, J=7.8, 1.5 Hz), 8.18-8.27 (3H, m), 8.56-8.60 (1H, m), 8.66-8.69 (1H, m), 9.91 (1H, s)

Example 117

N-(3-ethoxy-1H-pyrazol-5-yl)-3-(pyridin-2-ylsulfonyl)benzamide

The entitled compound was produced according to the method of Example 116 (step 1) but using 5-ethoxy-1-{[2-(trimethylsilyl)ethoxy]methyl}-1H-pyrazole-3-amine,
which had been produced according to the method of Reference Example 9 (step 1) using ethanol and 3-amino-5-hydroxypyrazoleamine as the starting materials, and the compound obtained in Reference Example 8 as the starting materials.
$^1$H-NMR (CDCl$_3$) δ: 1.40 (3H, t, J=7.2 Hz), 4.19 (2H, q, J=7.2 Hz), 5.87 (1H, s), 7.48-7.54 (1H, m), 7.69 (1H, t, J=7.8 Hz), 7.98 (1H, td, J=7.8, 1.6 Hz), 8.18-8.28 (3H, m), 8.53-8.57 (1H, m), 8.65-8.70 (1H, m), 9.54 (1H, s)

Example 118

N-(3-propoxy-1H-pyrazol-5-yl)-3-(pyridin-2-ylsulfonyl)benzamide

The entitled compound was produced according to the method of Example 116 (step 1) but using 5-propoxy-1-{[2-(trimethylsilyl)ethoxy]methyl}-1H-pyrazole-3-amine,
which had been produced according to the method of Reference Example 9 (step 1) using 1-propanol and 3-amino-5-hydroxypyrazoleamine as the starting materials, and the compound obtained in Reference Example 8 as the starting materials.
$^1$H-NMR (CDCl$_3$) δ: 0.99 (3H, t, J=7.6 Hz), 1.72-1.82 (2H, m), 4.06 (2H, t, J=6.6 Hz), 5.93 (1H, s), 7.46-7.54 (1H, m), 7.66 (1H, t, J=7.8 Hz), 7.97 (1H, td, J=7.8, 2.0 Hz), 8.16-8.27 (3H, m), 8.58 (1H, s), 8.64-8.70 (1H, m), 10.10 (1H, s).

Example 119

N-(3-butoxy-1H-pyrazol-5-yl)-3-(pyridin-2-ylsulfonyl)benzamide

The entitled compound was produced according to the method of Example 116 (step 1) but using 5-butoxy-1-{[2-(trimethylsilyl)ethoxy]methyl}-1H-pyrazole-3-amine,
which had been produced according to the method of Reference Example 9 (step 1) using 1-butanol and 3-amino-5-hydroxypyrazoleamine as the starting materials, and the compound obtained in Reference Example 8 as the starting materials.
$^1$H-NMR (DMSO-d$_6$) δ: 0.91 (3H, t, J=7.3 Hz), 1.32-1.47 (2H, m), 1.59-1.71 (2H, m), 4.04 (2H, t, J=6.6 Hz), 5.50-6.11 (1H, m), 7.70 (1H, ddd, J=7.7, 4.8, 1.1 Hz), 7.80 (1H, br s), 8.12-8.20 (2H, m), 8.24-8.31 (2H, m), 8.51 (1H, s), 8.69-8.72 (1H, m)

Example 120

N-(3-methoxypyridin-2-yl)-3-(pyridin-2-ylsulfonyl)benzamide

The entitled compound was produced according to the method of Example 92 but using the compound obtained in Reference Example 8 and 3-methoxypyridine-2-amine as the starting materials.
$^1$H-NMR (CDCl$_3$) δ: 3.93 (3H, s), 7.12 (1H, dd, J=8.3, 4.9 Hz), 7.23 (1H, dd, J=8.3, 1.5 Hz), 7.47-7.51 (1H, m), 7.69 (1H, t, J=7.8 Hz), 7.96 (1H, td, J=7.8, 2.0 Hz), 8.10 (1H, d, J=4.4 Hz), 8.19-8.28 (3H, m), 8.49-8.58 (2H, m), 8.66-8.70 (1H, m)

Example 121

N-(4-isopropylphenyl)-3-(pyridin-2-ylsulfonyl)benzamide

The entitled compound was produced according to the method of Example 92 but using the compound obtained in Reference Example 8 and 4-isopropylaniline as the starting materials.
$^1$H-NMR (CDCl$_3$) δ: 1.24 (6H, d, J=6.8 Hz), 2.83-2.95 (1H, m), 7.21 (2H, d, J=8.8 Hz), 7.45-7.49 (1H, m), 7.56 (2H, d, J=8.8 Hz), 7.63 (1H, t, J=7.8 Hz), 7.93 (1H, td, J=7.8, 1.8 Hz), 8.15-8.21 (3H, m), 8.32 (1H, s), 8.49-8.53 (1H, m), 8.62-8.67 (1H, m)

Example 122

N-(5-isopropoxypyridin-2-yl)-3-(pyridin-2-ylsulfonyl)benzamide

The entitled compound was produced according to the method of Example 92 but using the compound obtained in Reference Example 8 and 5-isopropoxypyridine-2-amine as the starting materials.
$^1$H-NMR (CDCl$_3$) δ: 1.36 (6H, d, J=5.9 Hz), 4.48-4.61 (1H, m), 7.30 (1H, dd, J=9.3, 2.9 Hz), 7.46-7.52 (1H, m), 7.70 (1H, t, J=7.8 Hz), 7.93-8.00 (2H, m), 8.21 (1H, d, J=7.8 Hz), 8.23-8.31 (3H, m), 8.53-8.56 (1H, m), 8.60 (1H, s), 8.66-8.70 (1H, m)

Example 123

N-[2-fluoro-4-(2-methoxy-1-methylethoxy)phenyl]-3-(pyridin-2-ylsulfonyl)benzamide At room temperature, triethylamine (0.045 mL) and methanesulfonyl chloride (0.025 mL) were added in that order to an ethyl acetate (1 mL) solution of 1-methoxypropan-2-ol (29.0 mg). After this was stirred at room temperature for 15 minutes, the precipitated solid was collected through filtration. The filtrate was concentrated, the resulting residue was dissolved in DMF (1.0 mL), and the compound (80.0 mg) obtained in Reference Example 11 and potassium carbonate (89.0 mg) were added thereto in that order. The reaction liquid was stirred overnight at 60° C., and water was added to the reaction liquid and extracted with ethyl acetate. The organic layer was dried with sodium sulfate, the drying agent was removed through filtration, and the solvent was evaporated off under reduced pressure. The residue was purified through preparative thin layer chromatography (NH silica gel, ethyl acetate/hexane=20%) to give the entitled compound (37.0 mg, 39%) as a pale red oily substance.

$^1$H-NMR (CDCl$_3$) δ: 1.31 (3H, d, J=6.3 Hz), 3.41 (3H, s), 3.49 (1H, dd, J=10.2, 4.4 Hz), 3.58 (1H, dd, J=10.2, 6.3 Hz), 4.46-4.55 (1H, m), 6.72-6.79 (2H, m), 7.46-7.52 (1H, m), 7.68 (1H, t, J=7.8 Hz), 7.92-8.01 (2H, m), 8.07 (1H, t, J=8.8 Hz), 8.16 (1H, d, J=7.8 Hz), 8.21-8.28 (2H, m), 8.49-8.54 (1H, m), 8.65-8.70 (1H, m)

Example 124

N-{2-fluoro-4-[2-fluoro-1-(fluoromethyl)ethoxy]phenyl}-3-(pyridin-2-ylsulfonyl)benzamide The entitled compound was produced according to the method of Example 123 but using the compound obtained in Reference Example 11 and 1,3-difluoropropan-2-ol as the starting materials.

$^1$H-NMR (CDCl$_3$) δ: 4.57-4.78 (5H, m), 6.79-6.87 (2H, m), 7.47-7.53 (1H, m), 7.69 (1H, t, J=7.8 Hz), 7.96 (1H, td, J=7.8, 2.0 Hz), 8.03 (1H, s), 8.12-8.20 (2H, m), 8.22-8.29 (2H, m), 8.51-8.55 (1H, m), 8.65-8.70 (1H, m)

Example 125

N-[4-(cyclopentyloxy)-2-fluorophenyl]-3-(pyridin-2-ylsulfonyl)benzamide

At room temperature, bromocyclopentane (40.0 mg) and potassium carbonate (55.7 mg) were added in that order to a DMF (1.0 mL) solution of the compound (50.0 mg) obtained in Example 11, and stirred at 60° C. for 5 hours. The reaction liquid was diluted with ethyl acetate, and washed with saturated sodium bicarbonate water. The organic layer was dried with sodium sulfate, then the drying agent was removed through filtration, and the solvent was evaporated off under reduced pressure. The residue was purified through preparative thin-layer chromatography (methanol/chloroform=1%) to give the entitled compound (37.5 mg, 63%) as a pale red oily substance.

$^1$H-NMR (CDCl$_3$) δ: 1.58-1.69 (2H, m), 1.74-1.96 (6H, m), 4.68-4.77 (1H, m), 6.65-6.72 (2H, m), 7.47-7.52 (1H, m), 7.68 (1H, t, J=7.8 Hz), 7.92-7.99 (2H, m), 8.06 (1H, t, J=8.8 Hz), 8.16 (1H, d, J=7.8 Hz), 8.22-8.28 (2H, m), 8.51 (1H, s), 8.68 (1H, d, J=4.9 Hz)

Example 126

N-(2-fluoro-4-isopropoxyphenyl)-3-(pyridin-2-ylsulfonyl)benzamide

The entitled compound was produced according to the method of Example 125 but using the compound obtained in Reference Example 11 and 2-bromopropane as the starting materials.

$^1$H-NMR (CDCl$_3$) δ: 1.34 (6H, d, J=6.3 Hz), 4.45-4.57 (1H, m), 6.68-6.74 (2H, m), 7.47-7.52 (1H, m), 7.70 (1H, t, J=7.8 Hz), 7.91 (1H, s), 7.96 (1H, td, J=7.8, 2.0 Hz), 8.10 (1H, t, J=9.0 Hz), 8.16 (1H, d, J=7.8 Hz), 8.23-8.29 (2H, m), 8.51 (1H, s), 8.66-8.70 (1H, m)

Example 127

N-(2-fluoro-4-isobutoxyphenyl)-3-(pyridin-2-ylsulfonyl)benzamide

The entitled compound was produced according to the method of Example 125 but using the compound obtained in Reference Example 11 and 1-bromo-2-methylpropane as the starting materials.

$^1$H-NMR (CDCl$_3$) δ: 1.03 (6H, d, J=6.8 Hz), 2.04-2.15 (1H, m), 3.71 (2H, d, J=6.8 Hz), 6.68-6.75 (2H, m), 7.46-7.52 (1H, m), 7.68 (1H, t, J=7.8 Hz), 7.92-8.01 (2H, m), 8.07 (1H, t, J=8.8 Hz), 8.16 (1H, d, J=7.8 Hz), 8.21-8.27 (2H, m), 8.52 (1H, s), 8.65-8.70 (1H, m)

Example 128

N-(4-sec-butoxy-2-fluorophenyl)-3-(pyridin-2-ylsulfonyl)benzamide

The entitled compound was produced according to the method of Example 125 but using the compound obtained in Reference Example 11 and 2-chlorobutane as the starting materials.

$^1$H-NMR (CDCl$_3$) δ: 0.98 (3H, t, J=7.3 Hz), 1.30 (3H, d, J=6.3 Hz), 1.58-1.81 (2H, m), 4.21-4.31 (1H, m), 6.67-6.75 (2H, m), 7.46-7.54 (1H, m), 7.69 (1H, t, J=7.8 Hz), 7.90 (1H, s), 7.96 (1H, td, J=7.8, 1.5 Hz), 8.09 (1H, t, J=9.3 Hz), 8.16 (1H, d, J=7.8 Hz), 8.23-8.29 (2H, m), 8.49-8.53 (1H, m), 8.66-8.70 (1H, m)

Example 129

N-(6-bromo-5-isopropoxypyridin-2-yl)-3-(pyridin-2-ylsulfonyl)benzamide

The entitled compound was produced according to the method of Example 125 but using the compound obtained in Reference Example 13 and 2-iodopropane as the starting materials.

$^1$H-NMR (CDCl$_3$) δ: 1.41 (6H, d, J=5.9 Hz), 4.50-4.60 (1H, m), 7.29 (1H, d, J=8.8 Hz), 7.47-7.52 (1H, m), 7.71 (1H, t, J=7.8 Hz), 7.97 (1H, td, J=7.8, 1.5 Hz), 8.19 (1H, d, J=7.8 Hz), 8.23-8.33 (3H, m), 8.51-8.55 (1H, m), 8.62 (1H, s), 8.68 (1H, d, J=4.9 Hz)

Example 130

N-(4-isopropoxyphenyl)-3-(pyridin-3-ylsulfonyl)benzamide

The entitled compound was produced according to the method of Reference Example 8 (step 1) and Example 112 but using the compound obtained in Reference Example 14 and 3-iodopyridine as the starting materials.
¹H-NMR (CDCl₃) δ: 1.34 (6H, d, J=6.1 Hz), 4.49-4.59 (1H, m), 6.91 (2H, d, J=8.8 Hz), 7.45-7.56 (3H, m), 7.65-7.73 (1H, m), 7.81 (1H, s), 8.09-8.17 (2H, m), 8.24 (1H, d, J=8.0 Hz), 8.40 (1H, s), 8.82 (1H, dd, J=4.9, 1.7 Hz), 9.17 (1H, d, J=2.0 Hz)

Example 131

N-(4-isopropoxyphenyl)-3-[(4-methylpyridin-2-yl)sulfonyl]benzamide

The entitled compound was produced according to the method of Reference Example 8 (step 1) and Example 112 but using the compound obtained in Reference Example 14 and 2-bromo-4-methylpyridine as the starting materials.
¹H-NMR (CDCl₃) δ: 1.34 (6H, d, J=6.1 Hz), 2.49 (3H, s), 4.48-4.59 (1H, m), 6.90 (2H, d, J=8.8 Hz), 7.27-7.31 (1H, m), 7.53 (2H, d, J=8.8 Hz), 7.67 (1H, t, J=7.8 Hz), 7.96-8.04 (1H, m), 8.05 (1H, s), 8.20 (2H, d, J=7.8 Hz), 8.49 (1H, s), 8.51 (1H, d, J=4.9 Hz)

Example 132

N-(4-isopropoxyphenyl)-3-[(6-methylpyridin-2-yl)sulfonyl]benzamide

The entitled compound was produced according to the method of Reference Example 8 (step 1) and Example 112 but using the compound obtained in Reference Example 14 and 2-bromo-6-methylpyridine as the starting materials.
¹H-NMR (CDCl₃) δ: 1.34 (6H, d, J=6.1 Hz), 2.57 (3H, s), 4.48-4.59 (1H, m), 6.86-6.95 (2H, m), 7.30-7.36 (1H, m), 7.54 (2H, d, J=9.0 Hz), 7.67 (1H, t, J=7.8 Hz), 7.81 (1H, t, J=7.8 Hz), 7.98 (1H, s), 8.03 (1H, d, J=7.8 Hz), 8.17-8.24 (2H, m), 8.49 (1H, s)

Example 133

N-(4-methoxyphenyl)-3-(phenylsulfonyl)benzamide

The entitled compound was produced according to the method of Example 92 but using 3-(phenylsulfonyl)benzoic acid and 4-methoxyaniline as the starting materials.
¹H-NMR (CDCl₃) δ: 3.83 (3H, s), 6.93 (2H, d, J=8.8 Hz), 7.50-7.68 (6H, m), 7.78 (1H, s), 7.94-8.01 (2H, m), 8.07-8.14 (2H, m), 8.38 (1H, s)

Example 134

N-(2-methoxyphenyl)-3-(phenylsulfonyl)benzamide

The entitled compound was produced according to the method of Example 92 but using 3-(phenylsulfonyl)benzoic acid and 2-methoxyaniline as the starting materials.
¹H-NMR (CDCl₃) δ: 3.93 (3H, s), 6.93 (1H, d, J=8.0 Hz), 7.00-7.03 (1H, m), 7.11 (1H, dt, J=7.8, 1.4 Hz), 7.51-7.55 (2H, m), 7.63 (1H, d, J=7.8 Hz), 7.64 (1H, d, J=7.8 Hz), 7.98 (2H, d, J=7.2 Hz), 8.06-8.11 (2H, m), 8.43-8.52 (3H, m)

Example 135

N-(3-methoxypyridin-2-yl)-3-(phenylsulfonyl)benzamide

The entitled compound was produced according to the method of Example 92 but using 3-(phenylsulfonyl)benzoic acid and 3-methoxypyridine-2-amine as the starting materials.
¹H-NMR (CDCl₃) δ: 3.93 (3H, s), 7.12 (1H, dd, J=8.3, 4.9 Hz), 7.23 (1H, dd, J=8.3, 1.5 Hz), 7.50-7.68 (4H, m), 7.94-8.00 (2H, m), 8.07-8.17 (3H, m), 8.41 (1H, s), 8.44 (1H, s)

Example 136

N-(4-isopropylphenyl)-3-(phenylsulfonyl)benzamide

The entitled compound was produced according to the method of Example 92 but using 3-(phenylsulfonyl)benzoic acid and 4-isopropylaniline as the starting materials.
¹H-NMR (CDCl₃) δ: 1.25 (6H, d, J=7.0 Hz), 2.86-2.97 (1H, m), 7.22 (2H, d, J=8.4 Hz), 7.49-7.63 (6H, m), 7.95 (2H, d, J=8.4 Hz), 8.06-8.11 (3H, m), 8.40 (1H, s)

Example 137

3-[(4-fluorophenyl)sulfonyl]-N-(4-isopropylphenyl)benzamide

The entitled compound was produced according to the method of Example 92 but using the compound obtained in Reference Example 15 and 4-isopropylaniline as the starting materials.
¹H-NMR (CDCl₃) δ: 1.25 (6H, d, J=6.8 Hz), 2.84-2.97 (1H, m), 7.15-7.23 (4H, m), 7.55 (2H, d, J=8.4 Hz), 7.62 (1H, t, J=7.8 Hz), 7.94-7.98 (2H, m), 8.04 (1H, d, J=7.8 Hz), 8.09-8.10 (2H, m), 8.39 (1H, s)

Example 138

N-(5-isopropoxypyridin-2-yl)-3-(pyrimidin-2-ylsulfonyl)benzamide

The entitled compound was produced according to the method of Example 116 (step 1) but using the compound obtained in Reference Example 16 and 5-isopropoxypyridine-2-amine as the starting materials.
¹H-NMR (CDCl₃) δ: 1.36 (6H, d, J=5.9 Hz), 4.50-4.60 (1H, m), 7.31 (1H, dd, J=9.3, 2.9 Hz), 7.50 (1H, t, J=4.9 Hz), 7.74 (1H, t, J=7.8 Hz), 7.98 (1H, d, J=2.9 Hz), 8.24-8.29 (2H, m), 8.30-8.35 (1H, m), 8.59 (1H, s), 8.61-8.64 (1H, m), 8.92 (2H, d, J=4.9 Hz)

Example 139

N-(4-isopropoxyphenyl)-3-(pyrimidin-2-ylsulfonyl)benzamide

The entitled compound was produced according to the method of Example 116 (step 1) but using the compound obtained in Reference Example 16 and 4-isopropoxyaniline as the starting materials.
¹H-NMR (CDCl₃) δ: 1.34 (6H, d, J=5.9 Hz), 4.46-4.59 (1H, m), 6.86-6.93 (2H, m), 7.47-7.56 (3H, m), 7.72 (1H, t, J=7.8 Hz), 7.98 (1H, s), 8.24-8.31 (2H, m), 8.53 (1H, s), 8.89 (2H, t, J=5.4 Hz)

Example 140

N-(3-cyclopropyl-1H-pyrazol-5-yl)-3-(pyrimidin-2-ylsulfonyl)benzamide

The entitled compound was produced according to the method of Example 116 (step 1) but using the compound obtained in Reference Example 16 and 5-cyclopropyl-1H-pyrazole-3-amine as the starting materials.

¹H-NMR (CDCl₃) δ: 0.71-0.80 (2H, m), 0.92-1.01 (2H, m), 1.85-1.96 (1H, m), 6.38 (1H, s), 7.52 (1H, t, J=4.9 Hz), 7.70 (1H, t, J=7.8 Hz), 8.22 (1H, d, J=7.8 Hz), 8.27 (1H, d, J=7.8 Hz), 8.62 (1H, s), 8.91 (2H, d, J=4.9 Hz), 11.12 (1H, s).

Example 141

N-(4-isopropoxyphenyl)-3-(pyrazin-2-ylsulfonyl)benzamide

The entitled compound was produced according to the method of Example 116 (step 1) but using the compound obtained in Reference Example 17 and 4-isopropoxyaniline as the starting materials.
¹H-NMR (CDCl₃) δ: 1.34 (6H, d, J=5.9 Hz), 4.48-4.59 (1H, m), 6.91 (2H, d, J=8.8 Hz), 7.52 (2H, d, J=8.8 Hz), 7.72 (1H, t, J=7.8 Hz), 7.89 (1H, s), 8.21-8.26 (2H, m), 8.49 (1H, s), 8.63-8.66 (1H, m), 8.80 (1H, d, J=2.4 Hz), 9.43 (1H, d, J=1.5 Hz)

Example 142

N-(4-isopropoxyphenyl)-3-(1H-1,2,4-triazol-3-ylsulfonyl)benzamide

The entitled compound was produced according to the method of Reference Example 8 (step 1) and Example 112 but using the compound obtained in Reference Example 18 and 1H-1,2,4-triazole-3-thiol as the starting materials.
¹H-NMR (DMSO-d₆) δ: 1.25 (6H, d, J=6.1 Hz), 4.51-4.62 (1H, m), 6.91 (2H, d, J=8.8 Hz), 7.62 (2H, d, J=8.8 Hz), 7.82 (1H, t, J=8.0 Hz), 8.12-8.18 (1H, m), 8.28-8.34 (1H, m), 8.49 (1H, s), 8.84 (1H, s), 10.43 (1H, s)

Example 143

N-(4-isopropoxyphenyl)-3-(1H-pyrazol-4-ylsulfonyl)benzamide

The entitled compound was produced according to the method of Reference
Example 8 (step 1) and Example 112 but using the compound obtained in Reference Example 14 and 4-iodo-1H-pyrazole as the starting materials.
¹H-NMR (DMSO-d₆) δ: 1.25 (6H, d, J=6.1 Hz), 4.50-4.64 (1H, m), 6.91 (2H, d, J=9.0 Hz), 7.62 (2H, d, J=9.0 Hz), 7.75 (1H, t, J=7.8 Hz), 8.02 (1H, s), 8.09-8.13 (1H, m), 8.19 (1H, dt, J=7.8, 1.3 Hz), 8.43 (1H, t, J=1.6 Hz), 8.58 (1H, s), 10.36 (1H, s), 13.82 (1H, s)

Example 144

3-(Cyclohexylsulfonyl)-N-(4-isopropoxyphenyl)benzamide

The entitled compound was produced according to the method of Example 73 but using the compound obtained in Reference Example 19 and 4-isopropoxyaniline as the starting materials.
¹H-NMR (CDCl₃) δ: 1.04-1.30 (3H, m), 1.34 (6H, d, J=5.9 Hz), 1.36-1.48 (2H, m), 1.63-1.72 (1H, m), 1.80-1.92 (2H, m), 1.98-2.12 (2H, m), 2.87-3.02 (1H, m), 4.47-4.61 (1H, m), 6.91 (2H, d, J=8.8 Hz), 7.54 (2H, d, J=8.8 Hz), 7.70 (1H, t, J=7.8 Hz), 7.94 (1H, s), 8.01 (1H, d, J=7.8 Hz), 8.21 (1H, d, J=7.8 Hz), 8.27 (1H, s)

Example 145

3-(Cyclohexylsulfonyl)-N-(2-methoxyphenyl)benzamide

The entitled compound was produced according to the method of Example 73 but using the compound obtained in Reference Example 19 and 2-methoxyaniline as the starting materials.
¹H-NMR (CDCl₃) δ: 1.07-1.32 (3H, m), 1.37-1.51 (2H, m), 1.63-1.73 (1H, m), 1.83-1.93 (2H, m), 2.03-2.13 (2H, m), 2.96 (1H, tt, J=12.2, 3.4 Hz), 3.94 (3H, s), 6.95 (1H, dd, J=8.0, 1.5 Hz), 7.04 (1H, td, J=7.8, 1.5 Hz), 7.13 (1H, td, J=7.8, 1.8 Hz), 7.72 (1H, t, J=7.8 Hz), 8.05 (1H, dt, J=8.0, 1.5 Hz), 8.19 (1H, dt, J=7.8, 1.5 Hz), 8.34 (1H, t, J=1.5 Hz), 8.48 (1H, dd, J=7.8, 1.5 Hz), 8.54 (1H, s)

Example 146

3-(Cyclohexylsulfonyl)-N-(4-methoxyphenyl)benzamide

The entitled compound was produced according to the method of Reference Example 8 (step 1) and Example 112 but using 3-iodo-N-(4-methoxyphenyl)benzamide and cyclohexanethiol as the starting materials.
¹H-NMR (CDCl₃) δ: 1.05-1.29 (3H, m), 1.33-1.49 (2H, m), 1.64-1.72 (1H, m), 1.81-1.91 (2H, m), 1.99-2.11 (2H, m), 2.90-3.00 (1H, m), 3.83 (3H, s), 6.93 (2H, d, J=9.0 Hz), 7.57 (2H, d, J=9.0 Hz), 7.70 (1H, t, J=7.8 Hz), 8.01 (1H, d, J=7.8 Hz), 8.01-8.07 (1H, m), 8.22 (1H, d, J=8.0 Hz), 8.28 (1H, s)

Example 147

3-(Cyclohexylsulfonyl)-N-(3-methoxypyridin-2-yl)benzamide (Step 1) Production of 3-(cyclohexylsulfonyl)-N-[3-(cyclohexylsulfonyl)benzoyl]-N-(3-methoxypyridin-2-yl)benzamide The compound (100 mg) obtained in Reference Example 19 was dissolved in chloroform (2.0 mL), then 2-amino-3-methoxypyridine (46 mg), triethylamine (0.156 mL) and 25% dichloromethane solution of 2-chloro-1,3-dimethylimidazolinium chloride (0.200 mL) were added thereto in that order, and stirred at room temperature for 30 minutes. The reaction liquid was concentrated, and purified through reversed-phase HPLC (0.1% TFA acetonitrile/H₂O=from 10% to 95%, gradient) to give the intended compound (44 mg, 19%) as a white crystal.

(Step 2) Production of 3-(cyclohexylsulfonyl)-N-(3-methoxypyridin-2-yl)benzamide The compound (25 mg) obtained in the step 1 was dissolved in methanol (2.0 mL), then aqueous 2 M sodium hydroxide solution (0.20 mL) was added thereto, and stirred at room temperature for 4 hours. Ethyl acetate was added thereto, then washed with water and saturated brine in that order, and dried with sodium sulfate. The drying agent was removed through filtration, and the solvent was evaporated off under reduced pressure to give the entitled compound (15 mg, 100%) as a colorless solid.
¹H-NMR (CDCl₃) δ: 1.06-1.34 (3H, m), 1.36-1.50 (2H, m), 1.61-1.74 (1H, m), 1.82-1.92 (2H, m), 2.01-2.11 (2H, m), 2.89-3.00 (1H, m), 3.94 (3H, s), 7.13 (1H, dd, J=8.0, 4.9 Hz), 7.24 (1H, dd, J=8.2, 1.3 Hz), 7.72 (1H, t, J=7.8 Hz), 8.05 (1H, dt, J=7.8, 1.5 Hz), 8.12 (1H, d, J=4.9 Hz), 8.25 (1H, d, J=7.8 Hz), 8.32 (1H, s), 8.48 (1H, s)

Example 148

3-(Butylsulfonyl)-N-(3-methoxypyridin-2-yl)benzamide

The entitled compound was produced according to the method of Reference Example 8 (step 1) and Example 112 but using the compound obtained in Reference Example 20 and butane-1-thiol as the starting materials.
$^1$H-NMR (CDCl$_3$) δ: 0.94 (3H, t, J=7.3 Hz), 1.41-1.52 (2H, m), 1.62-1.71 (2H, m), 2.98 (2H, t, J=7.4 Hz), 3.93 (3H, s), 7.08 (1H, dd, J=8.3, 4.9 Hz), 7.20 (1H, dd, J=8.0, 1.5 Hz), 7.39 (1H, t, J=7.6 Hz), 7.45-7.50 (1H, m), 7.66 (1H, dt, J=7.6, 1.3 Hz), 7.85 (1H, t, J=1.7 Hz), 8.13 (1H, dd, J=4.9, 1.5 Hz), 8.45 (1H, s)

Example 149

2-Methoxy-N-(4-methoxyphenyl)-5-(piperidin-1-ylsulfonyl)benzamide

The entitled compound was produced according to the method of Example 92 but using 2-methoxy-5-(piperidin-1-ylsulfonyl)benzoic acid and 4-methoxyaniline as the starting materials.
$^1$H-NMR (CDCl$_3$) δ: 1.37-1.46 (2H, m), 1.57-1.68 (4H, m), 2.96-3.06 (4H, m), 3.82 (3H, s), 4.14 (3H, s), 6.91 (2H, d, J=8.9 Hz), 7.14 (1H, d, J=8.8 Hz), 7.57 (2H, d, J=8.9 Hz), 7.87-7.89 (1H, m), 8.62-8.63 (1H, m), 9.45 (1H, s)

Example 150

N-(4-isopropylphenyl)-2-methoxy-5-(piperidin-1-ylsulfonyl)benzamide

The entitled compound was produced according to the method of Example 92 but using 2-methoxy-5-(piperidin-1-ylsulfonyl)benzoic acid and 4-isopropylaniline as the starting materials.
$^1$H-NMR (CDCl$_3$) δ: 1.25 (6H, d, J=6.8 Hz), 1.39-1.46 (2H, m), 1.62-1.72 (4H, m), 2.89-2.98 (1H, m), 3.00-3.07 (4H, m), 4.13 (3H, s), 7.14 (1H, d, J=8.8 Hz), 7.23 (2H, d, J=8.5 Hz), 7.58 (2H, d, J=8.5 Hz), 7.88 (1H, dd, J=8.8, 2.4 Hz), 8.63 (1H, d, J=2.4 Hz), 9.49 (1H, s)

Example 151

2-Hydroxy-N-(4-isopropoxyphenyl)-5-(piperidin-1-ylsulfonyl)benzamide

Chlorobenzene (2.0 mL) was added to 2-hydroxy-5-(piperidin-1-ylsulfonyl)benzoic acid (470 mg), and under stirring, phosphorus trichloride (0.072 mL) was added thereto and kept stirred at 130° C. for 1 hour. 4-Isopropylaniline (249 mg) was added to it, and stirred at 130° C. for 16 hours. The solvent was evaporated off under reduced pressure, then ethyl acetate was added thereto, washed with water and saturated brine in that order, and dried with sodium sulfate. The drying agent was removed through filtration, and the solvent was evaporated off under reduced pressure. The residue was purified through silica gel column chromatography (ethyl acetate/hexane=from 0% to 50%, gradient) to give the intended product (515 mg, 75%) as a colorless solid.
$^1$H-NMR (CDCl$_3$) δ: 1.35 (6H, d, J=6.1 Hz), 1.38-1.47 (2H, m), 1.53-1.65 (4H, m), 2.98 (4H, t, J=5.4 Hz), 4.50-4.61 (1H, m), 6.93 (2H, d, J=8.8 Hz), 7.13 (1H, d, J=8.8 Hz), 7.51 (2H, d, J=8.8 Hz), 7.76 (1H, dd, J=8.8, 2.0 Hz), 8.11 (1H, d, J=2.2 Hz), 8.49 (1H, s), 12.91 (1H, s)

Example 152

2-Ethoxy-N-(4-isopropoxyphenyl)-5-(piperidin-1-ylsulfonyl)benzamide

The compound (30 mg) obtained in Example 151 was dissolved in DMF (0.50 mL), then potassium carbonate (30 mg) and iodoethane (0.030 mL) were added thereto in that order, and stirred at room temperature for 18 hours. This was purified through reversed-phase HPLC (0.1% TFA acetonitrile/H$_2$O=from 10% to 95%, gradient) to give the entitled compound (25 mg, 78%) as a colorless solid.
$^1$H-NMR (CDCl$_3$) δ: 1.34 (6H, d, J=6.1 Hz), 1.37-1.45 (2H, m), 1.60-1.73 (7H, m), 3.01 (4H, t, J=5.5 Hz), 4.36 (2H, q, J=7.0 Hz), 4.48-4.60 (1H, m), 6.90 (2H, d, J=9.0 Hz), 7.11 (1H, d, J=8.5 Hz), 7.56 (2H, d, J=9.0 Hz), 7.87 (1H, dd, J=8.5, 2.4 Hz), 8.66 (1H, d, J=2.4 Hz), 9.76 (1H, s)

Example 153

2-(Cyanoethoxy)-N-(4-isopropoxyphenyl)-5-(piperidin-1-ylsulfonyl)benzamide

The entitled compound was produced according to the method of Example 152 but using the compound obtained in Example 151 and bromoacetonitrile as the starting materials.
$^1$H-NMR (CDCl$_3$) δ: 1.34 (6H, d, J=6.1 Hz), 1.38-1.48 (2H, m), 1.60-1.71 (4H, m), 3.00 (4H, t, J=5.5 Hz), 4.48-4.60 (1H, m), 5.06 (2H, s), 6.90 (2H, d, J=9.0 Hz), 7.13 (1H, d, J=8.8 Hz), 7.55 (2H, d, J=9.0 Hz), 7.81 (1H, dd, J=8.8, 2.4 Hz), 8.39 (1H, d, J=2.2 Hz), 8.74 (1H, s)

Example 154

[2-{[(4-Isopropoxyphenyl)amino]carbonyl}-4-(piperidin-1-ylsulfonyl)phenoxy]acetic acid The compound (100 mg) obtained in Example 151 was dissolved in DMF (2.0 mL), then potassium carbonate (50 mg) and tert-butyl bromoacetate (0.047 mL) were added thereto in that order, and stirred at room temperature for 21 hours. Ethyl acetate was added to the reaction liquid, then washed with water and saturated brine in that order, and dried with sodium sulfate. The drying agent was removed through filtration, and the solvent was evaporated off under reduced pressure. The residue was purified through silica gel column chromatography (ethyl acetate/hexane=from 0% to 100%, gradient), to give a colorless oily compound (125 mg). Trifluoroacetic acid (2.0 mL) was added to the obtained compound (100 mg) and stirred at room temperature for 3 hours. The solvent was evaporated off under reduced pressure to give the entitled compound (100 mg, 100%) as a colorless solid.
$^1$H-NMR (DMSO-d$_6$) δ: 1.25 (6H, d, J=5.9 Hz), 1.30-1.39 (2H, m), 1.49-1.60 (4H, m), 2.88 (4H, t, J=5.2 Hz), 4.51-4.64 (1H, m), 5.03 (2H, s), 6.91 (2H, d, J=9.0 Hz), 7.40 (1H, d, J=8.8 Hz), 7.72 (2H, d, J=9.0 Hz), 7.85 (1H, dd, J=8.8, 2.4 Hz), 8.16-8.20 (1H, m), 10.44 (1H, s)

Example 155

N-(4-isopropylphenyl)-4-methoxy-3-(piperidin-1-ylsulfonyl)benzamide

The entitled compound was produced according to the method of Example 92 but using 4-methoxy-3-(piperidin-1-ylsulfonyl)benzoic acid and 4-isopropylaniline as the starting materials.

$^1$H-NMR (CDCl$_3$) δ: 1.25 (6H, d, J=6.8 Hz), 1.46-1.71 (6H, m), 2.86-2.95 (1H, m), 3.17-3.25 (4H, m), 3.95 (3H, s), 7.05 (1H, d, J=8.8 Hz), 7.23 (2H, d, J=8.8 Hz), 7.58 (2H, d, J=8.8 Hz), 8.10 (1H, s), 8.14 (1H, dd, J=8.8, 2.4 Hz), 8.31 (1H, d, J=2.4 Hz)

Example 156

2-Methoxy-N-(3-methoxypyridin-2-yl)-5-(piperidin-1-ylsulfonyl)benzamide

The entitled compound was produced according to the method of Example 92 but using 2-methoxy-5-(piperidin-1-ylsulfonyl)benzoic acid and 3-methoxypyridine-2-amine as the starting materials.

$^1$H-NMR (CDCl$_3$) δ: 1.37-1.46 (2H, m), 1.58-1.69 (4H, m), 2.98-3.03 (4H, m), 3.97 (3H, s), 4.14 (3H, s), 7.09 (1H, dd, J=7.8, 4.9 Hz), 7.15 (1H, d, J=8.8 Hz), 7.22 (1H, d, J=7.8 Hz), 7.89 (1H, dd, J=8.8, 2.4 Hz), 8.16 (1H, d, J=4.9 Hz), 8.68 (1H, d, J=2.4 Hz)

Example 157

N-(4-isopropylphenyl)-6-(phenylsulfonyl)pyridine-2-carboxamide (Step 1) Production of 6-chloro-N-(4-isopropylphenyl)pyridine-2-carboxamide The intended compound was produced according to the method of Example 92 but using 6-chloropyridine-2-carboxylic acid and 4-isopropylaniline as the starting materials.

(Step 2) Production of N-(4-isopropylphenyl)-6-(phenylthio)pyridine-2-carboxamide Benzenethiol (221 mg) and cesium carbonate (889 mg) were added in that order to an NMP (4.0 mL) solution of the compound (500 mg) obtained in the step 1, and stirred at 200° C. for 1 hour. After left cooled, ethyl acetate was added to the reaction solution, then washed three times with aqueous saturated sodium hydrogencarbonate solution, and dried with sodium sulfate. The drying agent was removed through filtration, and the solvent was evaporated off under reduced pressure. The residue was purified through silica gel column chromatography (ethyl acetate/hexane=from 0% to 80%, gradient) to give the intended product (639 mg, 100%) as a white solid.

(Step 3) Production of N-(4-isopropylphenyl)-6-(phenylsulfonyl)pyridine-2-carboxamide M-chloroperbenzoic acid (99.0 mg) was added to a chloroform (3.0 mL) solution of the compound (100 mg) obtained in the step 2, and stirred at room temperature for 3 hours. Ethyl acetate was added to the reaction solution, then washed three times with aqueous saturated sodium hydrogencarbonate solution, and dried with sodium sulfate. The drying agent was removed through filtration, and the solvent was evaporated off under reduced pressure. The residue was purified through silica gel column chromatography (NH Biotage Column, ethyl acetate/hexane=from 0% to 100%, gradient) to give the entitled compound (47.0 mg, 86%) as a white solid.

$^1$H-NMR (CDCl$_3$) δ: 1.26 (6H, d, J=6.8 Hz), 2.87-2.98 (1H, m), 7.23-7.28 (2H, m), 7.55-7.59 (2H, m), 7.59-7.65 (2H, m), 7.67-7.73 (1H, m), 8.10-8.13 (2H, m), 8.17 (1H, t, J=7.8 Hz), 8.35 (1H, dd, J=7.8, 1.5 Hz), 8.43 (1H, dd, J=7.8, 1.0 Hz), 9.40 (1H, s)

Example 158

N-(4-isopropylphenyl)-5-(phenylsulfonyl)nicotinamide (Step 1) Production of 5-bromo-N-(4-isopropylphenyl)nicotinamide The intended compound was produced according to the method of Example 92 but using 5-bromonicotinic acid and 4-isopropylaniline as the starting materials.

(Step 2) Production of N-(4-isopropylphenyl)-5-(phenylthio)nicotinamide

The intended compound was produced according to the method of Reference Example 8 (step 1) but using the compound obtained in the step 1 and benzenethiol as the starting materials.

(Step 3) Production of N-(4-isopropylphenyl)-5-(phenylsulfonyl)nicotinamide

The entitled compound was produced according to the method of Example 112 but using the compound obtained in the step 2 as the starting material.

$^1$H-NMR (CDCl$_3$) δ: 1.25 (6H, d, J=6.5 Hz), 2.85-3.00 (1H, m), 7.20-7.30 (3H, m), 7.50-7.68 (3H, m), 7.97 (2H, d, J=7.0 Hz), 8.19 (1H, s), 8.66 (1H, s), 9.22 (1H, s), 9.26 (1H, s)

Example 159

4-Isopropoxy-N-[3-(piperidin-1-ylsulfonyl)benzyl]benzamide

The compound (200 mg) obtained in Reference Example 22 was dissolved in DMF (2.0 mL), then sodium azide (200 mg) was added thereto and stirred at room temperature for 22 hours. Ethyl acetate was added to it, then washed with water and saturated brine in that order, and dried with sodium sulfate. The drying agent was removed through filtration, and the solvent was evaporated off under reduced pressure. The residue was purified through silica gel column chromatography (ethyl acetate/hexane=from 0% to 50%, gradient) to give a colorless oily compound (205 mg). The obtained colorless oily compound (200 mg) was dissolved in methanol (4.0 mL), then 10% palladium-carbon (60 mg) was added thereto, and stirred in a hydrogen atmosphere at room temperature for 23 hours. The reaction liquid was filtered through Celite, and the solvent was evaporated off under reduced pressure to give a colorless oily compound (181 mg). Using the obtained colorless oily compound (181 mg) and 4-isopropoxybenzoic acid (128 mg), and according to the method of Example 92, the intended compound (172 mg, 57%) was produced as a colorless solid.

¹H-NMR (CDCl₃) δ: 1.36 (6H, d, J=6.3 Hz), 1.37-1.46 (2H, m), 1.55-1.68 (4H, m), 2.97 (4H, t, J=5.4 Hz), 4.57-4.67 (1H, m), 4.71 (2H, d, J=6.3 Hz), 6.52 (1H, br s), 6.90 (2H, d, J=8.8 Hz), 7.46-7.53 (1H, m), 7.59 (1H, d, J=8.3 Hz), 7.63-7.71 (2H, m), 7.75 (2H, d, J=8.8 Hz)

Example 160

N-(4-isopropoxyphenyl)-2-[3-(piperidin-1-ylsulfonyl)phenyl]acetamide

Aqueous 30% sulfuric acid solution (3.0 mL) was added to the compound (100 mg) obtained in Reference Example 23, and stirred at 80° C. for 4 days. At 0° C., this was made to have a pH of 10 with aqueous 5 M sodium hydroxide solution added thereto, and then this was made to have a pH of 3 with 5 M hydrochloric acid, and thereafter this was extracted with ethyl acetate. The organic layer was washed with saturated brine, and dried with sodium sulfate. The drying agent was removed through filtration, and the solvent was evaporated off under reduced pressure to give a colorless oily compound (101 mg). Using the obtained colorless oily compound (100 mg) and 4-isopropoxyaniline (53 mg), and according to the method of Example 92, the intended compound (124 mg, 79%) was produced as a colorless solid.

¹H-NMR (CDCl₃) δ: 1.30 (6H, d, J=6.3 Hz), 1.34-1.48 (2H, m), 1.59-1.69 (4H, m), 3.00 (4H, t, J=5.4 Hz), 3.76 (2H, s), 4.43-4.54 (1H, m), 6.82 (2H, d, J=8.8 Hz), 7.07-7.21 (1H, m), 7.33 (2H, d, J=8.8 Hz), 7.50-7.57 (1H, m), 7.61 (1H, d, J=7.8 Hz), 7.69 (1H, d, J=7.8 Hz), 7.72 (1H, s)

Example 161

4-Isopropoxy-N-{2-[3-(piperidin-1-ylsulfonyl)phenyl]ethyl}benzamide

The compound (100 mg) obtained in Reference Example 23 was dissolved in methanol (2.0 mL), then hydrochloric acid/methanol solution (0.50 mL) and 10% palladium-carbon (50 mg) were added thereto, and stirred in a hydrogen atmosphere at room temperature for 22 hours. The reaction liquid was filtered through Celite, and the solvent was evaporated off under reduced pressure to give a yellow oily compound (120 mg). Using the obtained yellow oily compound (120 mg) and 4-isopropoxybenzoic acid (68 mg), and according to the method of Example 92, the entitled compound (111 mg, 68%) was produced as a colorless solid.

¹H-NMR (CDCl₃) δ: 1.34 (6H, d, J=6.3 Hz), 1.35-1.44 (2H, m), 1.55-1.69 (4H, m), 2.94 (4H, t, J=5.6 Hz), 3.02 (2H, t, J=7.1 Hz), 3.68-3.78 (2H, m), 4.54-4.67 (1H, m), 6.10 (1H, br s), 6.88 (2H, d, J=8.8 Hz), 7.45-7.50 (2H, m), 7.58-7.69 (4H, m)

Example 162

N-(4-isopropoxyphenyl)-3-[3-(piperidin-1-ylsulfonyl)phenyl]propanamide (Step 1) Production of 3-(piperidin-1-ylsulfonyl)benzaldehyde The compound (1.00 g) obtained in Reference Example 21 was dissolved in acetone (10 mL), then manganese dioxide (500 mg) was added thereto and stirred at 55° C. for 5 days. After left cooled, the reaction liquid was filtered through Celite, and the solvent was evaporated off under reduced pressure. The residue was purified through silica gel column chromatography (ethyl acetate/hexane=from 0% to 50%, gradient) to give the intended compound (572 mg, 58%) as a colorless solid.

(Step 2) Production of ethyl (2E)-3-[3-(piperidin-1-ylsulfonyl)phenyl]acrylate

Triethyl phosphonoacetate (398 mg) was dissolved in THF (3.0 mL), and at 0° C., sodium hydride (62 mg) was added thereto and stirred at 0° C. for 10 minutes. A solution prepared by dissolving the compound (300 mg) obtained in the step 1 in THF (3.0 mL) was added to it, and stirred at room temperature for 90 minutes. Water was added thereto, and extracted with ethyl acetate. The organic layer was washed with saturated brine, and dried with sodium sulfate. The drying agent was removed through filtration, and the solvent was evaporated off under reduced pressure. The residue was purified through silica gel column chromatography (ethyl acetate/hexane=from 0% to 50%, gradient) to give the intended compound (380 mg, 99%) as a colorless solid.

(Step 3) Production of (2E)-3-[3-(piperidin-1-ylsulfonyl)phenyl]acrylic acid

The compound (380 mg) obtained in the step 2 was dissolved in methanol (6.0 mL), then aqueous 2 M sodium hydroxide solution (1.10 mL) was added thereto and stirred at room temperature for 1 day. At 0° C., this was made to have a pH of 3 with 2 M hydrochloric acid added thereto, then water was added, and extracted with ethyl acetate. The organic layer was washed with saturated brine, and dried with sodium sulfate. The drying agent was removed through filtration, and the solvent was evaporated off under reduced pressure to give the intended compound (339 mg, 98%) as a colorless solid.

(Step 4) Production of (2E)-N-(4-isopropoxyphenyl)-3-[3-(piperidin-1-ylsulfonyl)phenyl]acrylamide The compound (150 mg) obtained in the step 3 and 4-isopropoxyaniline (77 mg) were reacted according to the method of Example 92 to give the intended compound (193 mg, 89%) as a colorless solid.

(Step 5) Production of N-(4-isopropoxyphenyl)-3-[3-(piperidin-1-ylsulfonyl)phenyl]propanamide The compound (64 mg) obtained in the step 4 was dissolved in methanol (2.0 mL), then 10% palladium-carbon (30 mg) was added thereto, and stirred in a hydrogen atmosphere at room temperature for 21 hours. The reaction liquid was filtered through Celite, and the solvent was evaporated off under reduced pressure. The residue was purified through silica gel column chromatography (ethyl acetate/hexane=from 0% to 100%, gradient) to give the entitled compound (55 mg, 86%) as a colorless solid.

¹H-NMR (CDCl₃) δ: 1.31 (6H, d, J=6.1 Hz), 1.32-1.40 (2H, m), 1.53-1.62 (4H, m), 2.66 (2H, t, J=7.4 Hz), 2.93 (4H, t, J=5.5 Hz), 3.13 (2H, t, J=7.4 Hz), 4.42-4.55 (1H, m), 6.82

(2H, d, J=9.0 Hz), 7.17 (1H, s), 7.34 (2H, d, J=9.0 Hz), 7.41-7.51 (2H, m), 7.59 (1H, dt, J=7.4, 1.6 Hz), 7.62 (1H, s)

Reference Example 1

3-{[(4-Isopropoxyphenyl)amino]carbonyl}benzenesulfonyl chloride 3-(Chlorosulfonyl)benzoyl chloride (5.00 g) was added to a toluene (50 mL) solution of 4-isopropoxyaniline (3.17 g), and stirred overnight at room temperature. The solid in the reaction system was removed through filtration, and the filtrate was evaporated under reduced pressure. The residue was purified through silica gel column chromatography (ethyl acetate/hexane=from 0% to 100%, gradient), then the resulting compound was suspended in diisopropyl ether added thereto, and the solid was collected through filtration to give the entitled compound (2.27 g, 35%) as a pale blue solid.

Reference Example 2

3-{[(4-Isopropylphenyl)amino]carbonyl}benzenesulfonyl chloride

The entitled compound was produced according to the method of Reference Example 1 but using 4-isopropylaniline and 3-(chlorosulfonyl)benzoyl chloride as the starting materials.

Reference Example 3

3-{[(2-Methoxyphenyl)amino]carbonyl}benzenesulfonyl chloride

The entitled compound was produced according to the method of Reference Example 1 but using 2-methoxyaniline and 3-(chlorosulfonyl)benzoyl chloride as the starting materials.

Reference Example 4

3-{[(4-Methoxyphenyl)amino]carbonyl}benzenesulfonyl chloride

The entitled compound was produced according to the method of Reference Example 1 but using 4-methoxyaniline and 3-(chlorosulfonyl)benzoyl chloride as the starting materials.

Reference Example 5

3,3'-{[(3-Methoxypyridin-2-yl)imino]dicarbonyl}dibenzenesulfonyl chloride

3-Methoxypyridine-2-amine (780 mg) was added to a toluene (50 mL) solution of 3-(chlorosulfonyl)benzoyl chloride (3.00 g), and stirred overnight at room temperature. Ethyl acetate was added to the reaction liquid, then washed twice with water and once with saturated brine, and dried with sodium sulfate. The drying agent was removed through filtration, and the solvent was evaporated off under reduced pressure. The residue was purified through silica gel column chromatography (ethyl acetate/hexane=form 0% to 80%, gradient) to give the entitled compound (608 mg, 18%) as a white solid.

Reference Example 6

3,3'-{[(5-Isopropoxypyridin-2-yl)imino]dicarbonyl}dibenzenesulfonyl chloride

The entitled compound was produced according to the method of Reference Example 5 but using 2-amino-5-isopropoxypyridine and 3-(chlorosulfonyl)benzoyl chloride as the starting materials.

Reference Example 7

Tert-butyl 5-{[3-(chlorosulfonyl)benzoyl]amino}-3-isopropoxy-1H-pyrazole-1-carboxylate (Step 1) Production of tert-butyl 5-amino-3-isopropoxy-1H-pyrazole-1-carboxylate The compound (5.35 g) obtained in Reference Example 9 (step 1) was dissolved in dichloromethane (100 mL), then aqueous 5 M sodium hydroxide solution (300 mL) and di-tert-butyl dicarbonate (8.68 g) were added thereto and stirred at room temperature for 3 days. The reaction liquid was extracted with ethyl acetate, the organic layer was washed with water and saturated brine in that order, and dried with sodium sulfate. The drying agent was removed through filtration, and the solvent was evaporated off under reduced pressure. The residue was purified through silica gel column chromatography (ethyl acetate/hexane=from 0% to 50%, gradient) to give the intended compound (6.28 g, 69%) as a pale yellow solid.

(Step 2) Production of tert-butyl 5-{[3-(chlorosulfonyl)benzoyl]amino}-3-isopropoxy-1H-pyrazole-1-carboxylate The entitled compound was produced according to the method of Reference Example 1 but using the compound obtained in the step 1 and m-chlorosulfonylbenzoyl chloride.

Reference Example 8

3-(Pyridin-2-ylsulfonyl)benzoic acid (Step 1) Production of 3-(pyridin-2-ylthio)benzoic acid Xantphos (3.75 g) and $Pd_2(dba)_3$ (2.97 g) were added in that order to a dioxane (150 mL) solution of 2-iodopyridine (7.31 g), 3-mercaptobenzoic acid (5.0 g) and N,N-diisopropylethylamine (11.30 mL), and stirred overnight in a nitrogen atmosphere at 100° C. After left cooled, the reaction solution was evaporated under reduced pressure, then ethyl acetate was added to the residue, washed three times with aqueous saturated ammonium chloride solution, and dried with sodium sulfate. The drying agent was removed through filtration, and the solvent was evaporated off under reduced pressure. The residue was purified through silica gel column chromatography (methanol/chloroform=from 0% to 20%, gradient) to give the intended product (4.95 g, 66%) as a brown solid.

(Step 2) Production of methyl 3-(pyridin-2-ylthio)benzoate

Thionyl chloride (2.34 mL) was dropwise added to a methanol (100 mL) solution of the compound (4.95 g)

obtained in the step 1, and stirred at 60° C. for 3 hours. After left cooled, the reaction solution was evaporated under reduced pressure, and ethyl acetate was added to the residue. This was washed twice with water, then with saturated brine, and dried with sodium sulfate. The drying agent was removed through filtration, and the solvent was evaporated off under reduced pressure. The residue was purified through silica gel column chromatography (ethyl acetate/hexane=from 0% to 80%, gradient) to give the intended product (3.64 g, 69%) as a colorless oily substance.

(Step 3) Production of methyl 3-(pyridin-2-ylsulfonyl)benzoate

Acetic acid (4.25 mL) and potassium permanganate (7.04 g) were added to a mixed solution of the compound (3.64 g) obtained in the step 2, in acetone (50 mL)/distilled water (50 mL), and stirred overnight at room temperature. Aqueous sodium sulfite solution was added to the reaction liquid, and stirred for 1 hour, and then the reaction solution was almost completely concentrated under reduced pressure. Chloroform and aqueous saturated sodium hydrogencarbonate solution were added to the residue, and extracted three times with chloroform. The organic layers were collected, dried with magnesium sulfate and concentrated under reduced pressure. The resulting residue was purified through silica gel column chromatography (ethyl acetate/hexane=from 0% to 100%, gradient) to give the intended product (3.44 g, 84%) as a white solid.

(Step 4) Production of 3-(pyridine-2-ylsulfonyl)benzoic acid

Aqueous 5 M sodium hydroxide solution (12.4 mL) was added to a methanol (50 mL) solution of the compound (3.44 g) obtained in the step 3, and stirred overnight at room temperature. The reaction liquid was neutralized with 5 M hydrochloric acid, and the solvent was evaporated off under reduced pressure. Methanol was added to the residue, stirred, then the solid was collected through filtration, and the solvent was evaporated off under reduced pressure to give the entitled compound (2.83 g, 87%) as a white solid.

Reference Example 9

5-Isopropoxy-1-{[2-(trimethylsilyl)ethoxy]methyl}-1H-pyrazole-3-amine (Step 1) Production of 5-isopropoxy-1H-pyrazole-3-amine Methanesulfonic acid (25 mL) was added to a 2-propanol (250 mL) solution of 3-amino-5-hydroxypyrazolamine (25 g), and stirred at 120° C. for 2 days. The reaction liquid was left cooled, and the solvent was evaporated off under reduced pressure. Aqueous saturated sodium hydrogencarbonate solution was added to the residue, then extracted with ethyl acetate, and dried with sodium sulfate. The drying agent was removed through filtration, and the solvent was evaporated off under reduced pressure to give the intended product (5.35 g, 15%).

(Step 2) Production of 5-isopropoxy-1-{[2-(trimethylsilyl)ethoxy]methyl}-1H-pyrazole-3-amine With cooling with ice, sodium hydride (1.44 g) was added to a DMF (100 mL) solution of the compound (4.84 g) obtained in the step 1, and stirred for 2 hours with cooling with ice. The reaction liquid was cooled to −18° C., and 2-(trimethylsilyl)ethoxymethyl chloride (6.38 mL) was dropwise added thereto. After stirred at −18° C. for 2 hours, this was heated up to room temperature, and further stirred for 1 hour. Aqueous saturated ammonium chloride solution was added to the reaction liquid, then extracted with ethyl acetate, and dried with sodium sulfate. The drying agent was removed through filtration, and the solvent was evaporated off under reduced pressure. The residue was purified through silica gel column chromatography (ethyl acetate/hexane=from 0% to 40%, gradient, and then methanol/chloroform=from 0% to 20%, gradient) to give the entitled compound (2.28 g, 25%).

Reference Example 10

2-Fluoro-4-(methoxymethoxy)aniline

10% Palladium-carbon (390 mg) as a catalyst was added to an ethanol (100 mL) solution of 2-fluoro-4-(methoxymethoxy)-1-nitrobenzene (3.86 g), and stirred overnight in a hydrogen atmosphere at room temperature. The catalyst was removed through filtration, the solvent was evaporated off under reduced pressure, and the resulting residue was purified through silica gel column chromatography (methanol/chloroform=from 0% to 20%, gradient) to give the entitled compound (2.40 g, 73%) as a brown oily substance.

Reference Example 11

N-(2-fluoro-4-hydroxyphenyl)-3-(pyridin-2-ylsulfonyl)benzamide (Step 1) Production of N-[2-fluoro-4-(methoxymethoxy)phenyl]-3-(pyridin-2-ylsulfonyl)benzamide The intended product was produced according to the method of Example 116 (step 1) but using the compound obtained in Reference Example 8 and the compound obtained in Reference Example 10 as the starting materials.

(Step 2) Production of N-(2-fluoro-4-hydroxyphenyl)-3-(pyridin-2-ylsulfonyl)benzamide 5 M hydrochloric acid was added to a THF (40 mL) solution of the compound (1.58 g) obtained in the step 1, and stirred at 60° C. for 5 hours. After left cooled, aqueous saturated sodium hydrogencarbonate solution was added to the reaction liquid, and extracted with ethyl acetate. The organic layer was dried with sodium sulfate, the drying agent was removed through filtration, and the solvent was evaporated off under reduced pressure. The residue was purified through silica gel column chromatography (methanol/chloroform=from 0% to 20%, gradient) to give the entitled compound (800 mg, 57%) as a white solid.

Reference Example 12

6-Bromo-5-(methoxymethoxy)pyridine-2-amine (Step 1) Production of 2-bromo-3-(methoxymethoxy)-6-nitropyridine With cooling with ice, chloromethyl methyl ether (1.04 mL) and potassium carbonate (3.16 g) were added to an acetone (30 mL) solution of 2-bromo-6-nitropyridin-3-ol (1.0 g), and stirred overnight at room temperature. The reaction liquid was concentrated under reduced pressure, ethyl acetate was added to the residue and washed with water and saturated brine. The organic layer was dried with sodium sulfate, then filtered and concentrated under reduced pressure. The residue was purified through silica gel column chromatography (ethyl acetate/hexane=from 0% to 50%, gradient) to give the intended product (1.16 g, 97%) as a brown solid.

(Step 2) Production of
6-bromo-5-(methoxymethoxy)pyridine-2-amine

Aqueous saturated ammonium chloride solution (2.0 mL) and iron powder (4.0 g) were added to an ethanol (20 mL) solution of the compound (482 mg) obtained in the step 1, and stirred with heating under reflux for 12 hours. After left cooled, water was added to the reaction liquid, and extracted with ethyl acetate. The organic layer was dried with sodium sulfate, filtered and concentrated under reduced pressure. The residue was purified through silica gel column chromatography (methanol/chloroform=from 0% to 20%, gradient) to give the entitled compound (294 mg, 69%) as a brown solid.

Reference Example 13

N-(6-bromo-5-hydroxypyridin-2-yl)-3-(pyridin-2-ylsulfonyl)benzamide

The entitled compound was produced according to the method of Example 116 (step 2) but using the compound obtained in Reference Example 8 and 6-bromo-5-(methoxymethoxy)pyridine-2-amine obtained in Reference Example 12 as the starting materials.

Reference Example 14

N-(4-isopropoxyphenyl)-3-mercaptobenzamide

The entitled compound was obtained according to the method of Example 92 but using 4-isopropoxyaniline and 3-mercaptobenzoic acid as the starting materials.

Reference Example 15

3-[(4-Fluorophenyl)sulfonyl]benzoic acid (Step 1) Production of
3-[(4-fluorophenyl)thio]benzoic acid Copper(II) oxide (4.01 g) and cesium carbonate (19.7 g) were added in that order to an N-methylpyrrolidinone (100 mL) solution of 4-fluorobenzenethiol (3.10 g) and 3-iodobenzoic acid (5.00 g), and stirred overnight at 160° C. After left cooled, the solid in the reaction solution was removed through filtration. 1 M hydrochloric acid was added to the filtrate, extracted three times with ethyl acetate and dried with sodium sulfate. The drying agent was removed through filtration, and the solvent was evaporated off under reduced pressure. The residue was suspended in a mixed solvent of chloroform/hexane, and the solid was collected through filtration to give the intended product (4.08 g, 82%) as a white solid.

(Step 2) Production of
3-[(4-fluorophenyl)sulfonyl]benzoic acid

Manganese sulfate 5-hydrate (20.0 mg) was added to an acetonitrile (46 mL) solution of the compound (1.00 g) obtained in the step 1, and a mixed solution of aqueous 30% hydrogen peroxide (34 mL)/aqueous 0.2 M sodium hydrogencarbonate solution was dropwise added thereto, and stirred overnight at room temperature. 0.1 M hydrochloric acid was added to the reaction liquid, and then extracted twice with ethyl acetate. The organic layers were collected, dried with sodium sulfate, and concentrated under reduced pressure. The resulting residue was suspended in a mixed solvent of chloroform/hexane, and the solid was collected through filtration to give the entitled compound (921 mg, 82%) as a white solid.

Reference Example 16

3-(Pyrimidin-2-ylsulfonyl)benzoic acid

The entitled compound was produced according to the method of Reference Example 8 but using 2-bromopyrimidine and 3-mercaptobenzoic acid as the starting materials.

Reference Example 17

3-(Pyrazin-2-ylsulfonyl)benzoic acid

The entitled compound was produced according to the method of Reference Example 8 but using 2-iodopyrazine and 3-mercaptobenzoic acid as the starting materials.

Reference Example 18

3-Iodo-N-(4-isopropoxyphenyl)benzamide

The entitled compound was produced according to the method of Example 92 but using 3-iodobenzoic acid and 4-isopropoxyaniline as the starting materials.

Reference Example 19

3-(Cyclohexylsulfonyl)benzoic acid (Step 1) Production of ethyl
3-(cyclohexylthio)benzoate Ethyl 3-iodobenzoate (5.00 g) was dissolve din dioxane (100 mL), and cyclohexanethiol (2.32 mL), N,N-diisopropylethylamine (6.29 mL), Xantphos (2.09 g) and Pd$_2$(dba)$_3$ (1.66 g) were added thereto in that order, and stirred in a nitrogen atmosphere at 100° C. for 7 hours. After left cooled, ethyl acetate was added to it, then washed with water ad saturated brine in that order, and dried with sodium sulfate. The drying agent was removed through filtration, the solvent was evaporated off under reduced pressure, and the residue was purified through silica gel column chromatography (ethyl acetate/hexane=from 0% to 25%, gradient) to give the intended compound (5.11 g) as an orange oil.

(Step 2) Production of ethyl
3-(cyclohexylsulfonyl)benzoate

The compound (5.11 g) obtained in the step 1 was dissolved in chloroform (100 mL), and at 0° C., m-chloroperbenzoic acid (15.0 g) was added thereto, and stirred for 2 hours at 0° C. Aqueous 10% sodium thiosulfate solution was added to the reaction liquid, then aqueous 10% potassium carbonate solution was added, and extracted with ethyl acetate. The organic layer was washed with aqueous 10% potassium carbonate solution and saturated brine in that order, and dried with sodium sulfate. The drying agent was removed through filtration, and the solvent was evaporated off under reduced pressure. The residue was purified through silica gel column chromatography (ethyl acetate/hexane=from 0% to 50%, gradient) to give the intended product (5.30 g, 99%) as a pale yellow oil.

(Step 3) Production of
3-(cyclohexylsulfonyl)benzoic acid

The compound (5.30 g) obtained in the step 2 was dissolved in methanol (80 mL), then aqueous 2 M sodium hydroxide solution (17.9 mL) was added thereto and stirred at room temperature for 5 hours. This was made to have a pH of about 2 with 2 M hydrochloric acid added thereto, and then methanol was evaporated off under reduced pressure. The residue was extracted with ethyl acetate, and the organic layer was washed with saturated brine, and dried with sodium sulfate. The drying agent was removed through filtration, and the solvent was evaporated off under reduced pressure. The residue was suspended in diethyl ether added thereto, and the solid was collected through filtration to give the entitled compound (3.78 g, 79%) as a colorless solid.

Reference Example 20

3-Iodo-N-(3-methoxypyridin-2-yl)benzamide

2-Amino-3-methoxypyridine (1.50 g) was dissolved in THF (20 mL), and at 0° C., triethylamine (3.37 mL) and 3-iodobenzoyl chloride (3.23 g) were added thereto and stirred at room temperature for 30 minutes. Triethylamine (3.37 mL) and 3-iodobenzoyl chloride (3.23 g) were further added and stirred at room temperature for 18 hours. Chloroform was added to the reaction liquid, then washed with aqueous saturated sodium hydrogencarbonate solution, and dried with sodium sulfate. The drying agent was removed through filtration, and the solvent was evaporated off under reduced pressure. The residue was suspended in ethyl acetate (about 50 mL) added thereto, then the solid was collected through filtration as a colorless solid (5.96 g). Methanol (50 mL) and aqueous 2 M sodium hydrogencarbonate solution (3.42 mL) were added to the obtained solid (2.00 g), and stirred at room temperature for 18 hours. Methanol was evaporated off under reduced pressure, then ethyl acetate was added to the residue, washed with water and saturated brine in that order, and dried with sodium sulfate. The drying agent was removed through filtration, and the solvent was evaporated off under reduced pressure. The residue was purified through silica gel column chromatography (ethyl acetate/hexane=from 0% to 100%, gradient) to give the entitled compound (1.15 g, 80%) as an orange oil.

Reference Example 21

[3-(Piperidin-1-ylsulfonyl)phenyl]methanol 3-(Piperidin-1-ylsulfonyl)benzoic acid (7.00 g) was dissolved in THF (70 mL), and at 0° C., N,N'-carbodiimidazole (6.32 g) was added thereto and stirred at 0° C. for 4 hours. A solution prepared by dissolving sodium borohydride (1.97 g) in water (10 mL) was dropwise added to the reaction liquid, and then stirred at 0° C. for 1 hour. Water was added thereto, and extracted with ethyl acetate. The organic layer was washed with saturated brine, and dried with sodium sulfate. The drying agent was removed through filtration, and the solvent was evaporated off under reduced pressure. The residue was purified through silica gel column chromatography (ethyl acetate/hexane=from 0% to 100%, gradient) to give the entitled compound (7.01 g, 100%) as a colorless oil.

Reference Example 22

1-{[3-(chloromethyl)phenyl]sulfonyl}piperidine

Phosphorus oxychloride (1.00 mL) was added to DMF (5.0 mL), and stirred at 80° C. for 30 minutes. A solution prepared by dissolving [3-(piperidin-1-ylsulfonyl)phenyl]methanol (2.00 g) obtained in Reference Example 21 in DMF (5.0 mL) was added to it, and stirred at 80° C. for 30 minutes. At 0° C., aqueous saturated sodium carbonate solution was added thereto, and extracted with ethyl acetate. The organic layer was washed with water and saturated brine in that order, and dried with sodium sulfate. The drying agent was removed through filtration, and the solvent was evaporated off under reduced pressure. The residue was purified through silica gel column chromatography (ethyl acetate/hexane=from 0% to 50%, gradient) to give the entitled compound (1.26 g, 59%) as a colorless solid.

Reference Example 23

[3-(Piperidin-1-ylsulfonyl)phenyl]acetonitrile

The compound (500 mg) obtained in Reference Example 22 was dissolved in DMF (5.0 mL), and tetraethylammonium cyanide (500 mg) was added thereto and stirred at room temperature for 18 hours. Ethyl acetate was added to it, washed with water and saturated brine in that order, and dried with sodium sulfate. The drying agent was removed through filtration, and the solvent was evaporated off under reduced pressure. The residue was purified through silica gel column chromatography (ethyl acetate/hexane=from 0% to 50%, gradient) to give the entitled compound (342 mg, 71%) as a colorless solid.

The usefulness of the compounds of the invention as medicines is proved, for example, by the following Pharmacological Test Example.

Pharmacological Test Example 1 (LCE Enzyme Activity-inhibitory Test)

A test compound was dissolved in dimethyl sulfoxide (DMSO to be 10 mM), and then diluted with DMSO to prepare a 1000-fold concentrated solution of the test concentration. An improved Moon et al's method (J. Biol. Chem., Vol. 276, pp. 45358-45366, 2001) was employed for the LCE enzyme activity-inhibitor test. Concretely, the diluted compound was applied to a 96-well assay plate (Corning, 96-well assay block) in an amount of 1.0 µL/well; 50 µL of a phosphate buffer solution (100 mM potassium phosphate buffer, pH 6.5), and 25 µL of a substrate solution (100 mM potassium phosphate buffer (pH 6.5), 4.0 µM rotenone, 80 µM fatty acid-free bovine serum albumin, 160 µM palmitoyl CoA, 80 µM malonyl CoA, 3.5 µM [$^{14}$C]-malonyl CoA (1.92 GBq/mmol, by Amersham)) were added to each well; 25 µL of an enzyme solution (100 mM potassium phosphate buffer (pH 6.5), 100 µg/mL human LCE) was added thereto; the top of the plate was airtightly sealed up; and this was incubated with gently shaking and stirring at 37° C. for 90 minutes. Next, 100 µL of 5 M hydrochloric acid was added to each well, and the assay plate was stirred at room temperature for 5 minutes to stop the enzyme reaction with hydrolyzing the acyl CoA. Next, the enzyme reaction solution in each well was adsorbed by each well of a 96-well GF/C filter plate (Perkin Elmer Unifilter 96 GF/C); the individual wells were washed with water to remove the non-adsorbed malonyl CoA; and the GF/C filter plate was dried at 50° C. for 60 minutes. Next, 30 μL of a scintillator (Perkin Elmer Microscinti 0) was added to each well; then the top of the plate was sealed up; and the fixed [$^{14}$C] radioactivity was measured with a microplate scintillation counter (Perkin Elmer TopCount) to be the enzyme activity. The human LCE enzyme-inhibitory activity of the test compound was calculated, based on the radioactivity of the DMSO-added well with no test compound therein as a control. The activity of the compounds of the invention was analyzed according to the present assay, and the compounds inhibited the human LCE activity. The results are shown in Table 1.

TABLE 1

| Example No. | Activity Value IC50 (μM) |
| --- | --- |
| 1 | 2.2 |
| 2 | 0.036 |
| 3 | 7.4 |
| 4 | 5.1 |
| 5 | 0.030 |
| 6 | 1.1 |
| 7 | 0.051 |
| 8 | 9.6 |
| 9 | 0.15 |
| 10 | 0.76 |
| 11 | 1.0 |
| 12 | 6.8 |
| 13 | 5.2 |
| 14 | 1.2 |
| 15 | 0.12 |
| 16 | 0.11 |
| 17 | 0.34 |
| 18 | 0.51 |
| 19 | 1.5 |
| 20 | 0.53 |
| 21 | 0.20 |
| 22 | 5.1 |
| 23 | 0.13 |
| 24 | 0.67 |
| 25 | 0.28 |
| 26 | 3.5 |
| 27 | 0.19 |
| 28 | 0.17 |
| 29 | 0.18 |
| 30 | 0.10 |
| 31 | 2.8 |
| 32 | 0.10 |
| 33 | 2.6 |
| 34 | 0.053 |
| 35 | 5.2 |
| 36 | 0.081 |
| 37 | 0.066 |
| 38 | 1.0 |
| 39 | 5.2 |
| 40 | 8.0 |
| 41 | 5.1 |
| 42 | 0.50 |
| 43 | 0.53 |
| 44 | 15 |
| 45 | 10 |
| 46 | 0.79 |
| 47 | 1.4 |
| 48 | 0.21 |
| 49 | 0.067 |
| 50 | 0.053 |
| 51 | 0.33 |
| 52 | 0.93 |
| 53 | 7.6 |
| 54 | 1.6 |
| 55 | 0.31 |
| 56 | 3.2 |
| 57 | 0.83 |
| 58 | 0.16 |
| 59 | 0.11 |
| 59' | 3.0 |
| 60 | 1.1 |
| 61 | 0.054 |
| 62 | 0.093 |

TABLE 1-continued

| Example No. | Activity Value IC50 (μM) |
| --- | --- |
| 63 | 0.018 |
| 64 | 0.0050 |
| 65 | 0.0059 |
| 66 | 0.028 |
| 67 | 0.010 |
| 68 | 0.013 |
| 69 | 0.0023 |
| 70 | 0.0068 |
| 71 | 14 |
| 72 | 1.2 |
| 73 | 5.5 |
| 74 | 4.9 |
| 75 | 6.9 |
| 76 | 2.6 |
| 77 | 0.034 |
| 78 | 7.9 |
| 79 | 2.2 |
| 80 | 0.044 |
| 81 | 1.9 |
| 82 | 7.3 |
| 83 | 5.0 |
| 84 | 2.6 |
| 85 | 6.0 |
| 86 | 3.0 |
| 87 | 0.21 |
| 88 | 2.2 |
| 89 | 1.5 |
| 90 | 9.6 |
| 91 | 0.031 |
| 92 | 9.1 |
| 93 | 1.3 |
| 94 | 5.1 |
| 95 | 4.3 |
| 96 | 0.32 |
| 97 | 2.5 |
| 98 | 0.26 |
| 99 | 0.036 |
| 100 | 0.039 |
| 101 | 0.91 |

TABLE 2

| Example No. | Activity Value IC50 (μM) |
| --- | --- |
| 102 | 3.4 |
| 102 | 1.9 |
| 104 | 0.16 |
| 105 | 0.084 |
| 106 | 1.8 |
| 107 | 0.52 |
| 108 | 0.10 |
| 109 | 3.2 |
| 110 | 0.21 |
| 111 | 0.25 |
| 112 | 9.5 |
| 113 | 0.40 |
| 114 | 2.8 |
| 115 | 0.31 |
| 116 | 0.012 |
| 117 | 0.28 |
| 118 | 0.024 |
| 119 | 0.0060 |
| 120 | 0.39 |
| 121 | 0.18 |
| 122 | 0.26 |
| 123 | 2.7 |
| 124 | 0.35 |
| 125 | 0.24 |
| 126 | 0.15 |
| 127 | 1.0 |
| 128 | 0.19 |
| 129 | 4.5 |
| 130 | 1.5 |
| 131 | 1.6 |
| 132 | 0.68 |

TABLE 2-continued

| Example No. | Activity Value IC50 (μM) |
|---|---|
| 133 | 3.7 |
| 134 | 0.42 |
| 135 | 0.51 |
| 136 | 0.16 |
| 137 | 0.69 |
| 138 | 0.24 |
| 139 | 0.13 |
| 140 | 0.38 |
| 141 | 1.5 |
| 142 | 5.1 |
| 143 | 4.5 |
| 144 | 0.074 |
| 145 | 0.21 |
| 146 | 1.1 |
| 147 | 0.19 |
| 148 | 1.1 |
| 149 | 1.0 |
| 150 | 0.031 |
| 151 | 3.6 |
| 152 | 0.18 |
| 153 | 0.42 |
| 154 | 0.30 |
| 155 | 5.7 |
| 156 | 0.15 |
| 157 | 1.4 |
| 158 | 3.4 |
| 159 | 0.23 |
| 160 | 0.13 |
| 161 | 4.8 |
| 162 | 1.5 |

INDUSTRIAL APPLICABILITY

The compounds of the invention have an excellent LCE-inhibitory effect, and are useful as preventives or remedies for LCE-related various diseases, for example, circular system disorders, nervous system disorders, metabolic disorders, reproduction system disorders, digestive system disorders, neoplasm, infectious diseases, etc., or as herbicides.

The invention claimed is:

1. A compound or pharmaceutically acceptable salt thereof, selected from the group consisting of:

3-(2-Azabicyclo[2.2.1]hept-2-ylsulfonyl)-N-(3-methoxypyridin-2-yl)benzamide;

3-Isopropoxy-5-{[3-(piperidin-1-ylsulfonyl)benzoyl]amino}-1H-pyrazole hydrochloride;

N-(3-ethoxypyridin-2-yl)-3-(pyrrolidin-1-ylsulfonyl)benzamide;

N-(3-isopropoxy-1H-pyrazol-5-yl)-3-(pyridin-2-ylsulfonyl)benzamide;

N-(3-butoxy-1H-pyrazol-5-yl)-3-(pyridin-2-ylsulfonyl)benzamide;

N-(4-isopropylphenyl)-3-(phenylsulfonyl)benzamide;

N-(5-isopropoxypyridin-2-yl)-3-(pyrimidin-2-ylsulfonyl)benzamide; and

[2-{[(4-Isopropoxyphenyl)amino]carbonyl}-4-(piperidin-1-ylsulfonyl)phenoxy]acetic acid.

* * * * *